US006162640A

United States Patent [19]
Wohlstadter

[11] Patent Number: 6,162,640
[45] Date of Patent: Dec. 19, 2000

[54] SELECTION METHODS

[76] Inventor: Jacob Nathaniel Wohlstadter, 31 Sunset Rock Rd., Andover, Mass. 01810

[21] Appl. No.: 08/447,515

[22] Filed: May 23, 1995

Related U.S. Application Data

[62] Division of application No. 08/235,437, Apr. 29, 1994, which is a continuation of application No. 07/852,412, Mar. 16, 1992, abandoned.

[51] Int. Cl.[7] ............................... C12N 5/00; C12N 1/00; C12N 15/01; C12Q 1/68
[52] U.S. Cl. .............................. 435/325; 435/6; 435/243; 435/440
[58] Field of Search ................................. 435/6, 23, 69.1, 435/172.1, 243, 325, 440; 935/82

[56] References Cited

U.S. PATENT DOCUMENTS 5,258,289  11/1993  Davis et al. ........................... 435/69.6

OTHER PUBLICATIONS

Sambrook et al., *Molecular Cloning a Laboratory Manual* 2ed., (Cold Spring Harbor Laboratory), (1989).
Neidhardt et al., *Physiology of the Bacterial Cell* (Sinauer Associates Inc. Publishers) pp. 73 and 315 (1990).
Reich, *Proteases and Biological Control*, vol. 2, pp. 1–64 (1975).
Hyde et al., *J. of Biol. Chem.*, vol. 263, No. 33, pp. 17857–17871 (1988).
Kohl et al., *Proc. Natl. Acad. Sci. USA*, vol. 85, pp. 4686–4690 (1988).
Fersht, *Enzyme Structure and Mechanism*, 2ed., (Freeman & Co. Publishers) pp. 248–262 (1984).
Kantrowitz et al., *TIBS 15*, pp. 55–59 (1990).
Skerra et al., *Science*, vol. 240, pp. 1038–1040 (1988).
Pluckthun et al., *Methods in Enzymology*, vol. 178, pp. 497–515 (1989).
Better et al., *Science*, vol. 240, pp. 1041–1043 (1988).
W. Paul, *Fundamental Immunology* 2ed., (Raven Press) pp. 679–701 (1989).
Schlessinger et al., *Proc. Nat. Acad. Sci. USA*, vol. 72, No. 7, pp. 2775–2779 (1975).
Jaton et al., *J. of Immunology*, vol. 116, No. 5, pp. 1363–1366 (1976).
Givol et al., "Conformational changes in the Fab and Fc of the antibody as a consequence of antigen binding." *Proceedings of the Second International Congress of Immunology*, vol. 1, Edited by Brent and Holbrow. North Holland Publishers, Amsterdam, p. 39 (1974).
Jaton et al., "Conformational changes induced in a homogeneous anti-type III pneumococcal antibody by oligosaccharides of increasing size," *Biochemistry*, 14:5312 (1975).
Rini et al., *Science*, vol. 255, pp. 959–965 (1992).
Cantor et al., *Biophysical Chemistry Part I: The Conformation of Biological Molecules*, p. 127–145 (1990).
Buell et al., *Optimizing the expression in E. coli of a synthetic gene encoding somatomedin–C (IGF–I). Nucleic Acids Res.* 13:1923 (1985).
Dunn et al., *J. Mol. Biol.*, vol. 166, pp. 477–535 (1983).

Studier, F.W., *Virology*, 39, 562–568 (1969).
Studier, F.W., *Virology*, 95, 70–84 (1979).
Silhavy et al., *Microbiol. Rev.*, vol. 49, pp. 400–405 (1985).
Kutter et al., *Bacteriophage T4*, Structure, Organization, and Manipulation of the Genome, pp. 277–290 (1983).
Leonard et al., *J. of Biol. Chem.*, vol. 265, No. 18, pp. 10373–10382 (1990).
Starich et al., *Cell*, vol. 45, pp. 637–648 (1986).
Masker et al., *J. of Virology*, vol. 27, No. 1, pp. 149–163 (1978).
Baum et al., *Proc. Natl. Acad. Sci. USA*, vol. 87, pp. 10023–10027 (1990.
Carter et al., *Science*, vol. 237, pp. 394–398 (1987).
Husimi, *Advances in Biophysics*, 25:1–43 (1989).
Wiley et al., *Nature*, vol. 289, No. 29, pp. 373–378 (1981).
Nagai et al., *Nature*, vol. 309, No. 28, pp. 810–812 (1984).
Jia et al., *Gene*, 60, pp. 197–204 (1987).
Lehniger, *Principles of Biochemistry*, (Worth Publishers) p. 504 (1982).
Harlow et al., *Antibodies, a Laboratory Manual*, (Cold Spring Harbor Laboratory) pp. 139–281 (1989).
Rabkin et al., *J. Mol. Biol.*, vol. 204, pp. 903–916 (1988).
Kornberg et al., "Bacterial DNA Viruses," Chapter 17, from *DNA Replication*, pp. 586–597 (Freeman & Co. Publishers), (1992).
Stafford, K.,. "Continuous Fermentation," Chapter 11, from *maunal of Industrial Microbiology*, Edited by Deamin and Solomon, pp. 137–151 (1986).
Dykhuzien et al., *Microbiology Reviews*, vol. 47, No. 2, pp. 150–168 (1983).
Tsen, S., *Biochem. and Biophys. Res. Comm.*, vol. 166, No. 3, pp. 1245–1250 (1990).
Baum et al., *Proc. Natl. Acad. Sci. USA*, vol. 87, pp. 5573–5577 (1990).
Queener et al., "Screening and Selection for Strain Improvement," Chapter 12, from *Manual of Industrial Microbiology*, Edited by Deamin & Solomon, pp. 155–169 (1986).
Krausslich et al., *Proc. Natl. Acad. Sci. USA*, vol. 86, pp. 807–811 (1989).
Kotler et al., *Proc. Natl. Acad. Sci. USA*, vol. 85, pp. 4185–4189 (1988).

(List continued on next page.)

*Primary Examiner*—John S. Brusca
*Attorney, Agent, or Firm*—Whitman Breed Abbott & Morgan LLP

[57] ABSTRACT

A rational method for obtaining a novel molecule capable of a desired interaction with a substrate of interest comprising selecting hosts or replicators which incode said novel molecules based upon cell or replicator growth caused by the desired interaction of the novel molecule and a selection molecule expressed by said host.

78 Claims, 9 Drawing Sheets

OTHER PUBLICATIONS

Laskowski, "Deoxyribonuclease I," from *The Enzymes,* Third Edition, vol. 4, pp. 289–311, edited by Boyer (1971).

Oliphant et al., *Proc. Natl. Acad. Sci. USA,* (1989), vol. 86, pp. 9094–9098.

Lee et al., *EMBO Journal* (1992), vol. 11, No. 1, pp. 305–313.

Abelson, *Science* (1990), vol. 249, pp. 488–489.

Moore, "Pancreatic DNase," from *The Enzymes,* Third Edition, vol. 14, pp. 281–296, edited by Boyer (1981).

Kain, *Biotehcniques,* vol. 10, No. 3, pp. 366–73 (1991).

Ratner et al. Complete nucleotide sequence of the AIDS virus, HTLV–III Nature vol. 313 277–284, 1985.

Olshevsky et al. Identification of individual human imminodeficiency virus type 1 gp120 amino acids important for CD4 receptor binding J. Virology vol. 64 5701–5707, 1990.

Gething et al. Cloning and DNA sequence of double–stranded copies of haemagglutinin genes from H2 and H3 strains elucidates antigenic shift and drift in human influenza virus. Nature vol. 287 301–306, 1980.

SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
       (A) LENGTH: 7 amino acids
       (B) TYPE: amino acid
       (C) STRANDEDNESS: single
       (D) TOPOLOGY: linear (xi) SEQUENCE DESCRIPTION: SEQ ID NO:1:

Lys Arg Gly Pro Gly Ser Gly
1               5

(2) INFORMATION FOR SEQ ID NO:2:

(i) SEQUENCE CHARACTERISTICS:
       (A) LENGTH: 7 amino acids
       (B) TYPE: amino acid
       (C) STRANDEDNESS: single
       (D) TOPOLOGY: linear (xi) SEQUENCE DESCRIPTION: SEQ ID NO:2:

Lys Arg Gly Pro Asp Ser Gly
1               5

(2) INFORMATION FOR SEQ ID NO:3:

(i) SEQUENCE CHARACTERISTICS:
       (A) LENGTH: 7 amino acids
       (B) TYPE: amino acid
       (C) STRANDEDNESS: single
       (D) TOPOLOGY: linear (xi) SEQUENCE DESCRIPTION: SEQ ID NO:3:

Lys Arg Gly Pro Asp Asn Gly
1               5

(2) INFORMATION FOR SEQ ID NO:4:

(i) SEQUENCE CHARACTERISTICS:
       (A) LENGTH: 10 amino acids
       (B) TYPE: amino acid
       (C) STRANDEDNESS: single
       (D) TOPOLOGY: linear (xi) SEQUENCE DESCRIPTION: SEQ ID NO:4:

Thr Asp Gln Glu Gln Thr Ser Leu Tyr Val
1               5                   10

(2) INFORMATION FOR SEQ ID NO:5:

(i) SEQUENCE CHARACTERISTICS:
       (A) LENGTH: 10 amino acids
       (B) TYPE: amino acid
       (C) STRANDEDNESS: single
       (D) TOPOLOGY: linear (xi) SEQUENCE DESCRIPTION: SEQ ID NO:5:

Thr Asn Gln Glu Gln Thr Ser Leu Tyr Val
1               5                   10

(2) INFORMATION FOR SEQ ID NO:6:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:6:

Thr Asn Lys Glu Gln Thr Asn Leu Tyr Val
1               5                   10

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:7:

Pro Ile Asp Thr Cys Ile Ser
1               5

(2) INFORMATION FOR SEQ ID NO:8:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:8:

Pro Ile Gly Thr Cys Ile Ser
1               5

(2) INFORMATION FOR SEQ ID NO:9:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:9:

Pro Ile Asp Thr Cys Ser Ser
1               5

(2) INFORMATION FOR SEQ ID NO:10:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:10:

Cys Asn Asn
1

(2) INFORMATION FOR SEQ ID NO:11:

(i) SEQUENCE CHARACTERISTICS:
        (A) LENGTH: 3 amino acids
        (B) TYPE: amino acid
        (C) STRANDEDNESS: single
        (D) TOPOLOGY: linear (xi) SEQUENCE DESCRIPTION: SEQ ID NO:11:

```
Cys Asp Asn
  1

(2) INFORMATION FOR SEQ ID NO:12:

(i) SEQUENCE CHARACTERISTICS:
         (A) LENGTH: 3 amino acids
         (B) TYPE: amino acid
         (C) STRANDEDNESS: single
         (D) TOPOLOGY: linear (xi) SEQUENCE DESCRIPTION: SEQ ID NO:12:

Cys Asn Lys
  1

(2) INFORMATION FOR SEQ ID NO:13:

(i) SEQUENCE CHARACTERISTICS:
         (A) LENGTH: 25 amino acids
         (B) TYPE: amino acid
         (C) STRANDEDNESS: single
         (D) TOPOLOGY: linear (xi) SEQUENCE DESCRIPTION: SEQ ID NO:13:

Asn Asn Thr Arg Lys Ser Ile Arg Ile Gln Arg Gly Pro Gly Arg Ala
  1               5                  10                  15

Phe Val Thr Ile Gly Lys Ile Gly Asn
             20                  25

(2) INFORMATION FOR SEQ ID NO:14:

(i) SEQUENCE CHARACTERISTICS:
         (A) LENGTH: 11 amino acids
         (B) TYPE: amino acid
         (C) STRANDEDNESS: single
         (D) TOPOLOGY: linear (xi) SEQUENCE DESCRIPTION: SEQ ID NO:14:

Gln Phe Ile Asn Met Trp Gln Glu Val Gly Lys
  1               5                  10

(2) INFORMATION FOR SEQ ID NO:15:

(i) SEQUENCE CHARACTERISTICS:
         (A) LENGTH: 23 amino acids
         (B) TYPE: amino acid
         (C) STRANDEDNESS: single
         (D) TOPOLOGY: linear (xi) SEQUENCE DESCRIPTION: SEQ ID NO:15:

Glu Leu Tyr Lys Tyr Lys Val Val Lys Ile Glu Pro Leu Gly Val Ala
  1               5                  10                  15

Pro Thr Lys Ala Lys Arg Arg
             20

(2) INFORMATION FOR SEQ ID NO:16:

(i) SEQUENCE CHARACTERISTICS:
         (A) LENGTH: 10 amino acids
         (B) TYPE: amino acid
         (C) STRANDEDNESS: single
         (D) TOPOLOGY: linear (xi) SEQUENCE DESCRIPTION: SEQ ID NO:16:

Phe Ile Asn Met Trp Gln Glu Val Gly Lys
  1               5                  10
```

(2) INFORMATION FOR SEQ ID NO:17:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:17:

Lys Arg Gly Pro Gly Ser Gly
1           5

(2) INFORMATION FOR SEQ ID NO:18:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:18:

Thr Ala Thr Ile Met
1           5

(2) INFORMATION FOR SEQ ID NO:19:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:19:

Met Gln Arg Gly Asn
1           5

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:20:

Val Ser Gln Asn Tyr
1           5

(2) INFORMATION FOR SEQ ID NO:21:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:21:

Pro Ile Val Gln Asn
1           5

(2) INFORMATION FOR SEQ ID NO:22:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:22:

Lys Ala Arg Val Leu
1               5

(2) INFORMATION FOR SEQ ID NO:23:

(i) SEQUENCE CHARACTERISTICS:
             (A) LENGTH: 5 amino acids
             (B) TYPE: amino acid
             (C) STRANDEDNESS: single
             (D) TOPOLOGY: linear (xi) SEQUENCE DESCRIPTION: SEQ ID NO:23:

Ala Glu Ala Met Ser
1               5

(2) INFORMATION FOR SEQ ID NO:24:

(i) SEQUENCE CHARACTERISTICS:
             (A) LENGTH: 5 amino acids
             (B) TYPE: amino acid
             (C) STRANDEDNESS: single
             (D) TOPOLOGY: linear (xi) SEQUENCE DESCRIPTION: SEQ ID NO:24:

Cys Thr Leu Asn Phe
1               5

(2) INFORMATION FOR SEQ ID NO:25:

(i) SEQUENCE CHARACTERISTICS:
             (A) LENGTH: 5 amino acids
             (B) TYPE: amino acid
             (C) STRANDEDNESS: single
             (D) TOPOLOGY: linear (xi) SEQUENCE DESCRIPTION: SEQ ID NO:25:

Pro Ile Ser Pro Ile
1               5

(2) INFORMATION FOR SEQ ID NO:26:

(i) SEQUENCE CHARACTERISTICS:
             (A) LENGTH: 5 amino acids
             (B) TYPE: amino acid
             (C) STRANDEDNESS: single
             (D) TOPOLOGY: linear (xi) SEQUENCE DESCRIPTION: SEQ ID NO:26:

Thr Phe Gln Ala Tyr
1               5

(2) INFORMATION FOR SEQ ID NO:27:

(i) SEQUENCE CHARACTERISTICS:
             (A) LENGTH: 5 amino acids
             (B) TYPE: amino acid
             (C) STRANDEDNESS: single
             (D) TOPOLOGY: linear (xi) SEQUENCE DESCRIPTION: SEQ ID NO:27:

Pro Leu Arg Glu Ala
1               5

(2) INFORMATION FOR SEQ ID NO:28:

(i) SEQUENCE CHARACTERISTICS:

```
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:28:

Val Ser Phe Asn Phe
1               5

(2) INFORMATION FOR SEQ ID NO:29:

(i) SEQUENCE CHARACTERISTICS:
            (A) LENGTH: 5 amino acids
            (B) TYPE: amino acid
            (C) STRANDEDNESS: single
            (D) TOPOLOGY: linear (xi) SEQUENCE DESCRIPTION: SEQ ID NO:29:

Pro Gln Ile Thr Leu
1               5

(2) INFORMATION FOR SEQ ID NO:30:

(i) SEQUENCE CHARACTERISTICS:
            (A) LENGTH: 10 amino acids
            (B) TYPE: amino acid
            (C) STRANDEDNESS: single
            (D) TOPOLOGY: linear (xi) SEQUENCE DESCRIPTION: SEQ ID NO:30:

Thr Asp Gln Glu Gln Thr Ser Leu Tyr Val
1               5                   10

(2) INFORMATION FOR SEQ ID NO:31:

(i) SEQUENCE CHARACTERISTICS:
            (A) LENGTH: 25 amino acids
            (B) TYPE: amino acid
            (C) STRANDEDNESS: single
            (D) TOPOLOGY: linear (xi) SEQUENCE DESCRIPTION: SEQ ID NO:31:

Asn Asn Thr Arg Lys Ser Ile Arg Ile Gln Arg Gly Pro Gly Arg Ala
1               5                   10                  15

Phe Val Thr Ile Gly Lys Ile Gly Asn
            20                  25
```

SELECTION METHODS

This application is a division of copending U.S. application Ser. No. 08/235,437, filed Apr. 29, 1994, which in turn is a continuation of U.S. application Ser. No. 07/852,412, filed Mar. 16, 1992 and now abandoned.

TECHNICAL FIELD

The invention relates broadly to rational methods using recombinant genetic techniques and selection to isolate, create or direct the evolution of genes which express novel molecules having a desired interaction with substrates of interest.

More specifically, the invention relates to methods for isolating, creating or evolving novel molecules including organic, inorganic and biomolecules such as proteins, peptides, nucleic acids, oligonucleotides, lipids and polysaccharides for use as reactants, catalysts, enzymatic cofactors, repressors, enhancers, hormones and binders for a wide variety of substrates in industrial and therapeutic products.

Even more specifically, the invention relates to methods wherein host cells and/or viruses, which express a modulated growth factor for the host or for the virus functionally associated with a substrate of interest or analog thereof, and multiple copies of a putative novel molecule or a multiplicity of putative novel molecules which may interact with the substrate of interest or analog to alter the activity of the growth factor, are subjected to selection conditions or volutionary selection conditions to select for hosts or viruses, or mutations thereof carrying the gene which expresses the novel molecule of interest.

The methods of the invention can be used to rationally create molecules having a wide range of interesting properties including catalysts, e.g., proteases, binding peptides, enzymatic cofactors, enhancers, repressors, and hormones, among others, for a variety of industrial, research or therapeutic uses.

Several publications are referenced in this application by Arabic numerals within parentheses. Full citation for these references are found at the end of the specification immediately preceding the claims. The references more fully describe the state of the art to which this invention pertains as well as certain aspects of the invention itself.

BACKGROUND OF THE INVENTION

In general, there are three ways in which a molecule with novel properties may be obtained. A first method, e.g., protein engineering, relies on known properties of a general type of molecule and upon theoretical models which attempt to define the conformation of molecules most likely to have the desired properties. No models have proved general enough or exact enough to reproducibly design appropriate molecules.

A second method is screening. Screening requires that multiple permutations of molecules be tested for a given property. The current status of screening technology and the vast number of different permutations limits the usefulness of this technique. For example, a peptide sequence of twenty amino acids has $20^{20}$ different permutations. To screen bacteria producing different permutations of peptides of significant length, billions upon billions of petri dishes, each on the order of a thousand colonies, would be needed. To screen such large populations to find those few members, if any, which have the desired characteristics is extremely inefficient. Screening techniques are not adequate for the realistic performance of such tasks.

A third method employs natural selection in specific non-generalizable ways. For example, if a unicellular organism is missing an enzyme in a critical metabolic pathway, one can try to select for a molecule with the same function as that lost by the mutant. This technique is limited, however, by the reactions that are encoded in the genome of the organism and that may be complemented within the cell. Moreover, for each different complementation experiment, a new mutant strain is needed.

THE PRIOR ART

Methods for selecting organisms are well known in the art. These methods include growing host cells in the absence of an essential nutrient, on organic compounds which cannot be utilized by parental strains or in the presence of toxic analogs in order to select for organisms which, for example, express molecules essential for cell growth. Such techniques are primitive because growth in the absence of an essential nutrient does not permit the researcher to rationally design procedures for the selection of molecules for any specific type of reaction or for any particular targeted region within the substrate. Selection pressure based on growth in the absence of an essential nutrient is crude in that no rationally defined selection pressure through which a growth advantage or disadvantage is conferred is imposed and therefore hosts may be selected which achieve survival by expressing molecules having a range of functions. This limits the usefulness of such methods since it reduces the ability of the hosts to isolate or create molecules with specific desired capabilities.

For example, growth on organic compounds which cannot be utilized by parental strains is limited because the hosts are selected only on the basis of their capability of utilizing the organic compound. Use of the organic compound may be accomplished through any of a number of different reactions. There is no rational method to isolate, create or direct the evolution of a molecule capable of a specific reaction with a targeted region within a specific substrate.

Dube et al., *Biochemistry*, Vol. 28, No. 14, Jul. 11, 1989, disclose the remodeling of genes coding for β-lactamase, by replacing DNA at the active site with random nucleotide sequences. The oligonucleotide replacement preserves certain codons critical for activity but contains base pairs of chemically synthesized random sequences that code for more than a million amino acid substitutions. A population of *E. coli* were infected with plasmids containing these random inserts and the populations were incubated in the presence of carbenicillin and certain related analogs of carbenicillin. Seven new active-site mutants that rendered the *E. coli* host resistant to carbenicillin were selected, each containing multinucleotide substitutions that code for different amino acids. Each of the mutants exhibited a temperature-sensitive, β-lactamase activity. Dube et al. is thus limited to enhancing the already known function of a class of enzymes.

A process for producing novel molecules and DNA and RNA sequences through recombinant techniques and selection is disclosed in Kauffman et al., U.K, Patent Application No. GB 2183661A, filed Jun. 17, 1985. Mutated genes are introduced into host cells, the modified hosts are grown so that the mutated genes are cloned, thereby promoting production of the proteins expressed by said genes, the modified host cells are screened and/or selected so as to identify the strains of host cells producing novel proteins with a desired property, and the identified strains are grown so as to produce a novel molecule having the desired property. The techniques taught in Kauffman et al. like those in Dube et al. are limited to methods for modifying the known function of certain classes of molecules.

Schatz et al., *Cell*, Vol. 53, pp. 107–115 (1988) describe a method for the identification of a fibroblast cell line capable of expressing a gene which encodes an enzyme having known recombinase activity. The method is based upon a process of somatic recombination in which widely separated gene segments are ligated together to form a complete variable region (the variable region being assembled from V(variable), J(joining) and in some cases D(diversity) gene segments in an ordered and highly regulated fashion). Gene transfer is used to stably confer on a fibroblast the ability to carry out V(D)J rearrangements.

Retrovirus-based DNA recombination substrates that comprise a library of genes, some of which encode the recombinase gene, i.e., the gene which expresses the enzyme (s) which play a role in V(D)J recombination, were transfected into host cells which contain a gene expressing a growth factor flanked by the recombinase recognition sequences. Initially, the gene expressing the growth factor was not transcribed or translated. However, transcription and translation of the growth factor was activated when recombinase activity was expressed through the interaction of recombinase with the recombinase recognition sequences.

Bock et al., *Nature*, Vol. 355, pp. 564–567 (1992), report efforts to select DNA molecules with novel functions. Aptamers, stochastically generated oligonucleotides capable of binding specific molecular targets, were selected in cell-free selection procedures. Single-stranded DNA can be screened for aptamers that bind human thrombin, a protein with no known nucleic acid-binding function. These processes, which actually constitute cell-free screening procedures, include the screening and the amplification of some members of a sub-population. The other members are discarded.

Curtiss, PCT Application No. WO089/03427, discloses methods and techniques for expressing recombinant genes in host cells. Curtiss discloses genetically engineered host cells which express desired gene products because they are maintained in a genetically stable population. The genetically engineered cells are characterized by: (1) the lack of a gene encoding an enzyme essential for cell wall growth, i.e., the inability to catalyze a step in the biosynthesis of an essential cell wall structural component; (2) a first recombinant gene encoding an enzyme which is the functional replacement of the enzyme essential for cell wall growth; and, (3) a second recombinant gene encoding a desired polypeptide which is physically linked to the first recombinant gene. Loss of the first recombinant gene causes the cells to lyse when the cells are in an environment where a product expressed by the first recombinant gene is absent, and where the cells are grown in an environment such that the absence of the first recombinant gene causes the cells to lyse.

Baum et al., *Proc. Natl. Acad. Sci.*, (*USA*), Vol. 87, pp. 10023–10027 (1990), relates to a method for monitoring cleavage interactions by a variety of proteases. A fusion construct is created by inserting a protease cleavage site e.g., decapeptide human immunodeficiency virus ("HIV") protease recognition sequence, into specific locations of β-galactosidase in *E. coli*. Those construct genes, which retain their enzymic activity despite insertion of the cleavage site, are subcloned into plasmids which encode wild type and mutant HIV protease, respectively. The fusion construct was found to be cleaved by wild type HIV protease and not mutant HIV protease in both in vivo and in vitro experiments.

Upon cleavage by HIV protease, the altered β-galactosidase is inactivated. The cleavage reaction is inhibited by pepstatin A, a known inhibitor of HIV protease. An analogous construct was developed using a polio protease cleavage site, which was cleaved by polio protease.

Paoletti et al., U.S. Pat. No. 4,769,330, disclose methods for modifying the genome of vaccinia virus in order to produce vaccinia mutants, particularly by the introduction into the vaccinia genome of exogenous DNA. DNA sequences and unmodified and genetically modified microorganisms involved as intermediates are disclosed as are methods for infecting cells and host animals with the vaccinia mutants in order to amplify the exogenous DNA and proteins encoded by the exogenous DNA. This reference is representative of art-known recombinant techniques used to modify both viruses and host cell microorganisms.

Murphy, U.S. Pat. No. 5,080,898, relates to the use of recombinant DNA techniques to make analogs of toxin molecules and to the use of such molecules to treat medical disorders. The toxin molecules can be linked to any specific-binding ligand, whether or not it is a peptide, at a position which is predeterminedly the same for every toxin molecule.

Anderson et al., U.S. Pat. No. 4,403,035, disclose a method for delivery and transfer of genetic information by packaging a hybrid DNA-protein complex into a viral vector, and then transferring this genetic information from the hybrid virus into susceptible microorganisms. An organism having a function or capability desired to be transferred is selected and the DNA thereof is isolated/purified and cleaved to separate the exogenous genes controlling the function desired to be transferred or cloned. These exogenous genes are inserted into the DNA of a virus. The resulting hybrid DNA-protein is introduced into a cell-free in vitro medium, along with a source of viral capsid precursor structure, i.e., proheads, and required accessory viral structural and packaging proteins in order to assemble an infectious hybrid virus encapsidating the hybrid DNA.

The viral capsid precursor structure, and accessory viral structural and packaging proteins, are produced by infecting capable microorganisms with a first viral mutant capable of producing capsid precursor structures without producing at least one packaging protein and infecting compatible microorganisms with a second viral mutant capable of producing accessory viral structural and packaging proteins without producing capsid precursor structures. These infected cells are then mixed and lysed to provide the source of virus components for in vitro packaging for hybrid DNA-protein.

The hybrid virus is then used to infect microorganisms compatible with the virus to program the infected cells to serially reproduce the desired function of the exogenous genes and the genes themselves as nucleic acids.

Dulbecco, U.S. Pat. No. 4,593,002, discloses a method for incorporating DNA fragments into the DNA gene of a virus. The DNA fragments encode for proteins which have specific medical or commercial use. Small segments of an original protein exhibiting desired functions are identified and a DNA fragment, having a nucleotide base sequence encoding that segment of the protein, is isolated/purified from an organism or synthesized chemically. The isolated/purified DNA fragment is inserted into the DNA genome of the virus so that the inserted DNA fragment expresses itself as the foreign segment of a surface viral protein and so that neither the function of the protein segment nor the function of any viral protein critical for viral replication is impaired.

None of the prior art methods offers a rational approach employing selection procedures to the isolation, creation, or creation by directed evolution of novel molecules having a specific function with respect to a chosen substrate of interest. The screening methods are inherently inefficient, wasteful and time consuming. The primitive methods of selection disclosed in the art do not permit the creation, for example, of molecules having high specificity, either as a binder or as catalyst, for a particular recognition sequence. They produce limited numbers of molecules with limited properties. Moreover, none of the prior art references teach methods which are universal in their applicability. There are no prior art methods for the isolation, creation or directed evolution of genes which express different molecules each having a rationally designed activity with respect to a substrate of interest.

OBJECTS OF THE INVENTION

It is thus a primary object of the invention to create novel molecules, capable of interacting with substrates of interest.

It is a related object of the invention to create novel molecules for use as reactants, catalysts, enzymatic cofactors, repressors, enhancers, hormones and binders for substrates, while avoiding the time, effort and failure relatively associated with prior art protein engineering, screening and selection methods.

It is still a further object of the invention to harness the power of selection processes and recombinant genetic techniques to produce molecules not heretofore known and having new functions or improved known functions with respect to a wide array of substrates of interest.

It is still a further and related object of this invention to isolate the genes which express novel molecules from existing gene pools by matching the interactive specificity of these novel molecules to the substrates of interest for which they are specific.

It is still a further and related object of this invention to create novel molecules for interaction with the substrate of interest by rational design of selection based methods which employ specific expressible molecules incorporating the recognition sequences of the substrate of interest.

It is still a further and related object of this invention to harness the rapid replication of cellular and viral genomes in the selection of genes which express novel molecules of interest.

It is still another object of this invention to control and direct evolutionary pressures on cellular and viral systems so as to create and evolve genes which express novel molecules of interest having heretofore unknown physical and/or chemical interactions with substrates of interest.

SUMMARY OF THE INVENTION

The invention is broadly in rational methods for the isolation, creation or directed evolution of a gene which encodes a novel molecule capable of desired interaction with a substrate of interest. The method involves selecting hosts, or replicators in hosts, which encode novel molecules based upon cell or replicator growth caused by the desired interaction of the novel molecule and a selection molecule expressed by the host. The method is performed by expressing multiple copies of a putative novel molecule or a multiplicity of different putative novel molecules in a population of host cells containing a cell growth factor and/or a replicator (e.g., a virus) growth factor, and a substrate of interest or analog thereof functionally associated with said growth factor, and imposing selection conditions on the population of host cells to select for those hosts or those replicators which express a novel molecule which interacts with the substrate of interest or analog to alter the activity of the growth factor.

The invention is also in the modified host cells for use in the invention, in the modified replicators, in certain selection molecules used in carrying out the methods, in the genes and novel molecules produced by the methods of the invention and in systems and kits useful for practicing the invention.

Selection for Host Methods

The isolation, creation or directed evolution of a gene which encodes a novel molecule capable of a desired interaction with a substrate of interest may be performed by the steps of expressing in a population of host cells
multiple copies of a putative novel molecule or a multiplicity of putative novel molecules, and
adding or expressing a cell growth factor,
a substrate of interest or analog thereof having a recognition sequence which represents the substrate of interest and which is functionally associated with the growth factor, and optionally
a growth factor modulation moiety, and
imposing selection conditions on the population of host cells to select for those hosts containing genes capable of expressing a novel molecule which interacts with the recognition sequence to alter the activity of the growth factor.

The order of expression of the putative novel molecules and the order of expression and/or addition of the growth factor, substrate of interest or analog thereof and modulation moiety relative to one another and to the expression of the putative novel molecules, and the timing of the selection process with respect to any of such steps is a matter of choice. In some embodiments it may be advantageous to impose selection conditions on a population of hosts or replicators prior to modifying the host or replicators to express growth factors, recognition sequences or modulation moieties, or selection molecules incorporating same, so as to develop a desired host or replicator strain for subsequent selection.

The method may be performed by introducing a homogeneous population of genes which may express multiple copies of a putative novel molecule or a heterogeneous population of genes which may express a multiplicity of different putative novel molecules or molecules with evolutionary potential into a population of host cells whose genome has been artificially altered to express a cell growth factor and a recognition sequence which represents the substrate of interest and which is functionally associated with the growth factor, imposing selection conditions, e.g., cultivating or incubating the population of host cells under selection conditions to select for those hosts containing genes capable of expressing a novel molecule which interacts with the sequence to alter the activity of the growth factor and isolating/purifying the gene of interest from the selected cell population. The gene of interest may then be used to express additional quantities of the novel molecule.

The growth factor and recognition sequence may be present as individual molecules or groups of molecules, or, may be associated together in molecules which incorporate both of them. The host cells, e.g., *E. coli*, may be modified by exogenous addition of the growth factor and/or recognition sequence, or, the growth factor and/or recognition sequence may be expressed by the host. By imposing selection conditions on the population of host cells it is possible to select for those hosts containing genes, or mutations thereof, capable of expressing a novel molecule which has the desired interaction with the recognition sequence and which thereby affects the activity of the growth factor.

Selection for Replicator Methods

The isolation, creation or directed evolution of a gene which encodes a novel molecule capable of a desired interaction with a substrate of interest may also be performed by expressing multiple copies of a putative novel molecule or multiplicity of different putative novel molecules encoded by a replicator, e.g., a virus, in a population of host cells which contain or express a growth factor for the replicator, a substrate of interest or analog thereof which incorporates a recognition sequence which represents the substrate of interest and which is functionally associated with the growth factor, and optionally a growth factor modulation moiety, and imposing selection conditions on the population of host cells to select for the replicator, e.g., virus, capable of expressing a novel molecule which interacts with the recognition sequence so as to alter the activity of the growth factor.

These methods may be performed, for example, by introducing a replicator, e.g., a virus, into a population of host cells whose genome has been artificially altered to express a growth factor for the virus and a recognition sequence representing the substrate of interest which is functionally associated with the growth factor, cultivating or incubating that population of host cells to select for the viruses capable of expressing the novel molecule which interacts with the recognition sequence so as to alter the activity of the growth factor, and isolating/purifying the gene of interest. As in the host methods, the order of expression and/or addition of the several components of the process and the order of expression and/or addition relative to imposition of selection conditions is a matter of choice.

In such methods, a homogeneous population of viruses which expresses multiple copies of a putative novel molecule or a heterogeneous population of viruses containing a multiplicity of mutant genes, each of which may express a different putative novel molecule, is introduced into a population of modified host cells which contain a functionally down-modulated growth factor necessary for the growth and/or replication of the viruses and a recognition sequence as described above. Those viruses which express novel molecules which interact with the recognition sequence and thereby up-modulate the activity of the growth factor will replicate within the host. Those viruses which express novel molecules which do not have the desired interaction will not be replicated. The host cells can then be incubated or cultivated under selection conditions to select for the population of the viruses which express the novel molecules of interest.

In a preferred method, the genome of the host cells are artificially altered to express a molecule or molecules which include the growth factor and the recognition sequence which represents the substrate of interest and which is functionally associated with the growth factor. The population of cells is then infected by a replicator, e.g., a virus, whose genome is capable of expressing multiple copies of a molecule or a multiplicity of different molecules which may interact with the selection molecule expressed by the recombinant genome of the host cell. Those novel molecules which interact with the recognition sequence so as to alter the function of the growth factor will confer a selective growth advantage on the virus which expresses the novel molecule of choice. The population of host cells can then be cultivated or incubated to create an amplified population of the desired virus.

As in host selection, the genome of the host cells are artificially altered to express a growth factor and a recognition sequence, as individual molecules or as physical or chemical associations or combinations thereof. The recognition sequence represents the substrate of interest and is functionally associated with the replicator growth factor. Desirably the genome is modified by recombinant methods to express a selection molecule e.g., a fusion or deletion protein, which includes both the growth factor and the recognition sequence. The growth factor and recognition sequence may be associated with a selection moiety which modulates the activity of the growth factor. The selection moiety may be an individual molecule(s) or may be part of a selection molecule(s), e.g., fusion or deletion protein, which also includes the growth factor and the recognition sequence.

The novel molecule to be obtained may act through a cascade of events, i.e., it may interact with the recognition sequence to cause the desired effect or that interaction may start a cascade of events with any number of intermediate steps which ultimately affects the activity of the growth factor. Each molecule in the cascade can be a natural or engineered substrate within the host cell or an exogenously supplied substrate or can be, itself, a novel molecule.

The host selection and replicator selection methods of the invention can be used to create a wide range of novel molecules, e.g., novel proteases capable of a desired interaction with a protease recognition sequence. Molecules other than proteases can be produced, e.g., enzymes capable of site specific glycosylation (or phosphorylation, etc.) around an important cellular protein for growth which is particularly sensitive to glycosylation (or phosphorylation, etc.) and is permissive to the insertion of recognition sequences.

The universal selection method links the formation of virtually any product to the growth of a cell. For example, in the reaction A+B→C (catalyzed by X), linking the production of C to the growth ability of a cell, even though C may have no effect on the growth of the cell directly or indirectly, one can select for that member of a population of putative novel molecules which is capable of catalyzing the reaction (whatever the reaction type may be) or is capable of acting as a substrate or is capable of acting as the product C itself—in short—capable of acting in any way so as to contribute to the production of C.

The invention offers significant advantages over the prior art techniques. It offers an inherent efficiency increase over screening and places the burdens on the experimental system rather than on the experimenters. In selection, the environmental conditions determine which members of a population are viable. By properly defining the selection procedures and conditions, those clones with the desired properties can be obtained from a huge population. The selection procedures of the invention have the advantage that they may be used to obtain a vast array of novel molecules each of which is highly specific for a given recognition sequence and interaction. In contrast, the primitive selection methods of the prior art are crude and empirical.

DETAILED DESCRIPTION OF THE INVENTION

Definitions

Certain terms used herein are defined as follows.

The term "isolation" means bringing forth a gene which exists in nature from an existing gene pool.

The term "creation" means bringing forth a gene not found in nature which encodes a novel molecule.

The terms "directed evolution" and "creation by directed evolution" mean bringing forth a gene not found in nature which encodes a novel molecule by mutating genes under rationally designed selection conditions and pressures.

The term "novel molecules of new function" embraces any molecule having a previously unknown structure and/or sequence and/or physical/chemical properties and having a previously unknown or unrealized reaction type, e.g., phosphorylation, proteolysis, binding, etc., and/or specificity.

The term "functionally enhanced novel molecule" embraces molecules having a previously unknown structure and/or sequence and/or physical/chemical properties whose function, i.e., combination of reaction type, e.g., phosphorylation, proteolysis, binding, etc. and specificity is known or realized, but which differ in their degree of known function.

The term "novel molecule" includes any molecule having a previously unknown structure and/or sequence and/or physical/chemical properties or a novel molecule of new function or a functionally enhanced novel molecule and includes organic, inorganic and biomolecules such as nucleic acids, proteins, oligonucleotides, sugars, lipids, peptides and any substituted or modified versions thereof.

The terms "putative novel molecule", "putative functionally enhanced novel molecule" or "putative novel molecule of new function" mean any molecule, known or otherwise, which one skilled in the art considers to be a candidate for isolation, creation or directed evolution according to the methods of the invention.

The term "substrate of interest" includes any naturally occurring molecule or synthetic molecule, whether known or unknown, upon which a chemical and/or physical interaction is desired. The substrate of interest may comprise organic or inorganic molecules or biomolecules, e.g., proteins, oligonucleotides, lipids and polysaccharides. Substrates of interest include, for example, compounds which are known substrates for enzymatic action, peptides, polypeptides and proteins of various descriptions, which are to be reacted, cleaved, linked, modified or substituted, or bound by a novel molecule.

The term "analog of the substrate of interest" means a molecule or a portion thereof which contains a recognition sequence which renders it a functional analog of the substrate of interest.

The term "gene" is used in its broadest commonly understood meaning and includes any nucleic acid, e.g., oligonucleotides (DNA, RNA, etc.) capable of expression and further includes combinations or sets of genes.

The term "genome" refers to the entire complement of genes capable of being expressed, including chromosomal genes, plasmids, transposons and viral DNA.

The term "expression" has its generally understood scientific meaning and includes replication of oligonucleotides, transcription, translation and reverse transcription.

The term "expression by the host" means expression by any part of the host genome.

The terms "interaction" and "capable of interaction" broadly encompass any intermolecular and/or intramolecular operations including chemical reactions, catalysis or physical binding. The novel molecules sought to be created by the methods of the invention may be capable of reaction with the recognition sequence in any kind of reaction including, for example, isomerizations, additions, substitutions, syntheses and fragmentations, etc. Other "interactions" of interest may include (de)phosphorylation, (de)glycosylation, (de)hydroxylation, (de)adenylation, (de)acylation, (de)acetylation and stereo-isomerization. Such reactions may be limited to interactions between the novel molecules and the recognition sequence or may include the addition or deletion of atoms or molecules from the novel molecule and/or recognition sequence, respectively, and/or from the host cell or medium, respectively. Interactions may also include catalyses in which the novel molecule acts catalytically on the recognition sequence to effect, inter alia, proteolysis, esterolysis, hydrolysis, stereoisomerization, or to effect any of the reactions referred to above. The term interaction also includes binding interactions, e.g., as between antibodies and antigens or binding induced allosteric effects.

The term "host cell" includes a living organism which is unicellular, multicellular, procaryotic or eucaryotic, e.g., yeast, COS cells, CHO cells or hybridoma cells.

The term "growth factor" as used herein is a molecule(s) which confers a growth advantage or disadvantage upon a host cell or upon a replicator. Typical growth factors include nutrients, enzymes necessary for metabolism of nutrients, and binding and structural proteins, and proteins involved in replication, metabolism, formation and maintenance of essential structural components, or cellular and subcellular growth.

The term "recognition sequence" is used in its most universal chemical sense and means any chemical atom(s), bond(s), molecule(s), submolecular group(s), combination of any of the foregoing, or any physical or electrical state or configuration thereof, e.g., an amino acid sequence. The recognition sequence may be a discrete molecule or may be a submolecular portion of a complex molecule which includes the growth factor and/or the selection moiety.

It is essential that the recognition sequence has some functional interaction either directly or indirectly, with the growth factor and/or the selection moiety such that when the desired interaction of the novel molecule and the recognition sequence takes place, the function of the growth factor will be affected and has an impact (positive or negative) on cell or replicator growth. The function and/or the structure of the selection moiety and/or the recognition sequence may be combined and the function and/or structure of the recognition sequence and the growth factor may also be combined. As further described below, fusion or deletion proteins are particularly useful in the selection methods of the invention and represent an embodiment in which all three functions are combined in a single molecule.

Modifications to the recognition sequence enable selection of multiple novel molecules. For example, a large protein that is a substrate of interest may be able to tolerate insertion or replacement of a stretch of amino acids without losing its function, (29). It is possible to insert in such a protein a variety of different potential proteolytic recognition sequences in order to obtain multiple proteases of desired specificity.

It is also essential that the recognition sequence represent the substrate of interest. For example, the recognition sequence may be an amino acid sequence from a protein for which no known or satisfactory proteolytic enzyme exists. Incorporating that amino acid sequence or certain analogs thereof as recognition sequences in the methods of the invention, will lead to the creation of novel molecules having specificity and/or high turnover for the proteolysis of that amino acid sequence.

The term "selection moiety" or "modulation moiety" refers to any molecule which, in physical or chemical association with a growth factor, either directly or indirectly, either increases or decreases the function of that growth factor. The selection moiety may be for example a bulky protein which, because of steric hindrance and conformational changes, inactivates or functionally impairs the action of an enzyme necessary for cell or viral growth.

The terms "selection molecule" or "universal selection molecule" refer to a molecule which incorporates a growth factor and a recognition sequence and optionally a modulation moiety.

The term "artificial selection molecule" means a contrived selection molecule containing a recognition sequence which is not an inherent part of a natural or synthetic growth factor.

The term "replicator" refers to subcellular entities capable of replication, e.g., plasmids, viruses, bacteriophage, self-replicating oligonucleotides such as RNA molecules which have recognition sequences for a replicase(s), mycoplasma, etc. Replicator expression refers to expression directed by a replicator through the use of host and/or replicator components.

The terms "selection", "selection conditions" and "selection pressure" refer to generally known as well as novel procedures for growing a population of host cells in the absence of an essential nutrient, on compounds which cannot be utilized by parental strains, in the presence of toxins, in various peculiar environmental conditions, e.g., temperature, light, pH, or in the presence of mixed cultures, as may cause some but not all members of the population to survive and replicate.

A "nucleotide" is one of the five bases: adenine, cytosine, guanine, thymine and uracil, plus a sugar, deoxyribose or ribose, plus a phosphate.

An "oligonucleotide" is a sequence formed of at least two nucleotides, and a "polynucleotidell" is a long oligonucleotide and may be either RNA or DNA with or without modified bases. While the term oligonucleotide is generally used in the art to denote smaller nucleic acid chains, and "polynucleotide" is generally used in the art to denote larger nucleic acid chains including DNA or RNA chromosomes or fragments thereof, the use of one or the other term herein is not a limitation or description of size unless expressly stated to be.

The term "nucleic acid" refers to a polynucleotide of any length, including DNA or RNA genomes or fragments thereof, with or without modified bases as described above.

The term "isolation/purification" refers to techniques for isolating, purifying or extracting, as these terms are conventionally used, to describe methods for recovering a gene or a molecule from a cell and/or replicator and/or a medium.

The term "mutagenesis" refers to techniques for the creation of heterogeneous population of genes, e.g., by irradiation, chemical treatment, low fidelity replication, etc.

IN THE DRAWINGS

Figure 1A:
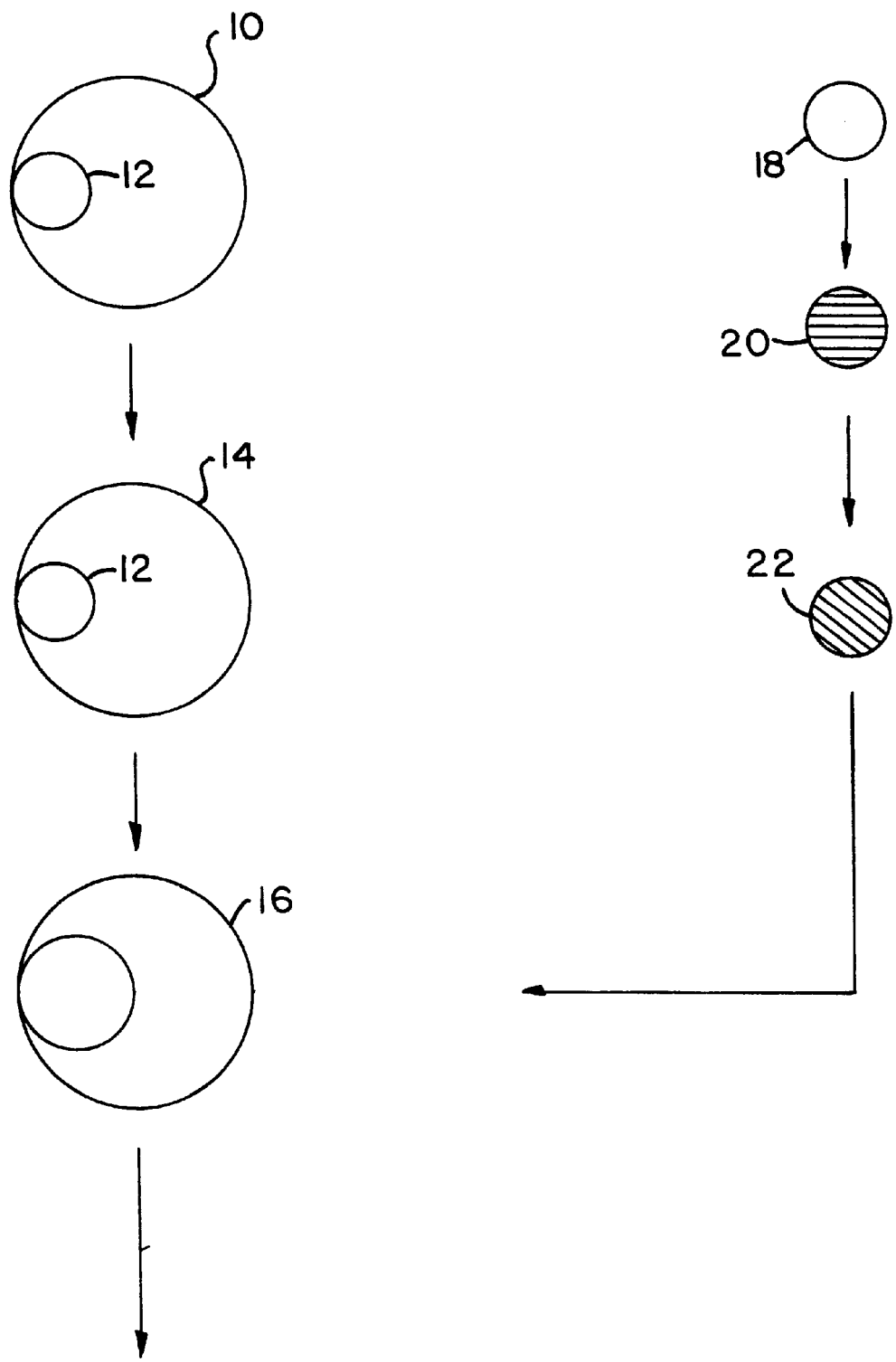
FIGS. 1A and 1B are schematic representations of a host-selection method embodiment of the invention for the creation or directed evolution of a gene which encodes a novel molecule.
Figure 1B:
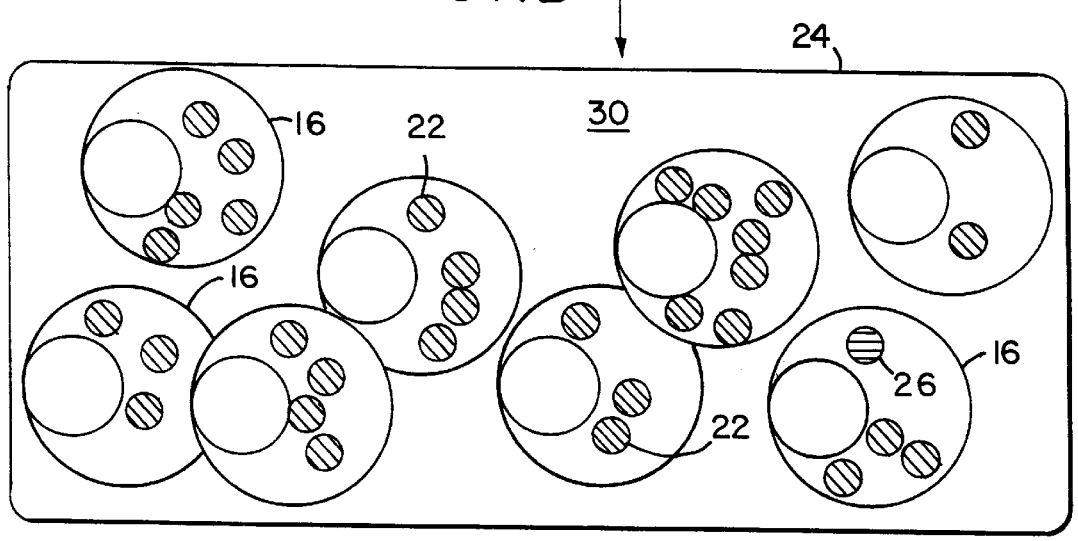
Figure 1B:
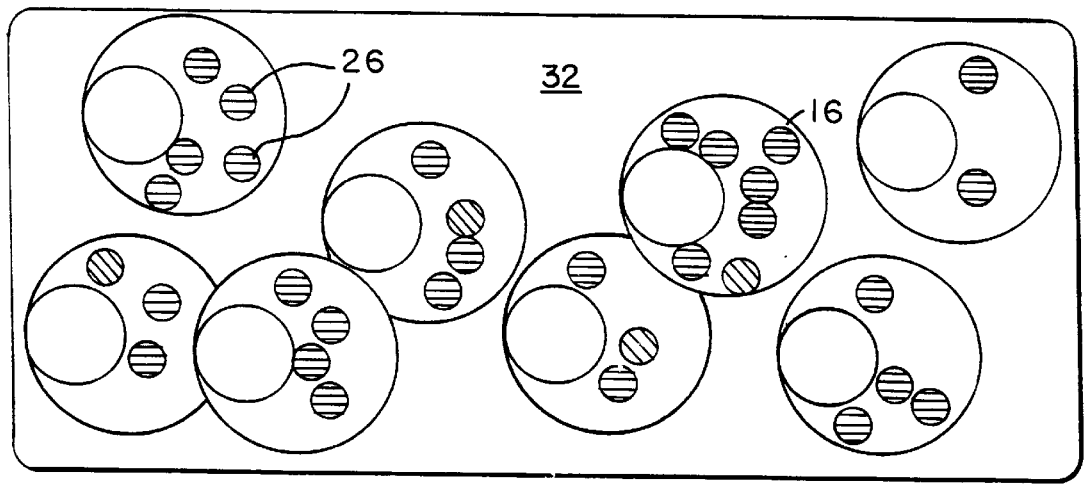

With reference to FIGS. 1A and 1B, reference numeral 10 refers to a host cell (E. coli) having chromosome 12. The cell is engineered, as described elsewhere, to be a deletion mutant, 14, lacking the ability to express an essential growth factor. E. coli deletion mutant 14 is further engineered as shown at reference numeral 16 to encode a selection molecule which incorporates the essential growth factor for the host cell in a down-modulated form and a recognition sequence.

Reference numeral 18 refers to a plasmid which is engineered as shown at reference numeral 20 to encode T7 bacteriophage origin of replication and low fidelity T7 replication machinery. Plasmid 20 is further engineered to encode a heterogeneous population of genes which express putative novel molecules. The so engineered plasmid is shown at reference numeral 22.

Plasmid 22 is introduced into transformed deletion mutant host 16 and cultivated in a suitable environment in a nutrient-rich, non-limiting medium as shown at reference numeral 24. Plasmids which express a novel molecule having the desired functional interaction with a selection molecule expressed by deletion mutant host 16 are shown at reference numeral 26.

Incubation in the nutrient-rich, non-limiting medium in incubator 24 results in the growth of a population of host cells 16 containing plasmids 22 and plasmid 26. The population of transformed host cells are shown at reference numeral 30.

The population of incubated host cells is then selected in a chemostat in nutrient-limiting medium. This confers a growth advantage upon those transformed host cells 16 harboring plasmids 26 which encode novel molecules having the desired function of interacting with the selection molecule and up-modulating the growth factor. The selected population of host cells is shown at reference numeral 32. As can be seen, those cells which harbor a plasmid which encodes a novel molecule having the desired function have had a preferential growth advantage.

The plasmids 26 are then isolated/purified from the selected population of cells 32. The novel molecule genes are cloned, sequenced and functionally characterized.

Figure 2A:
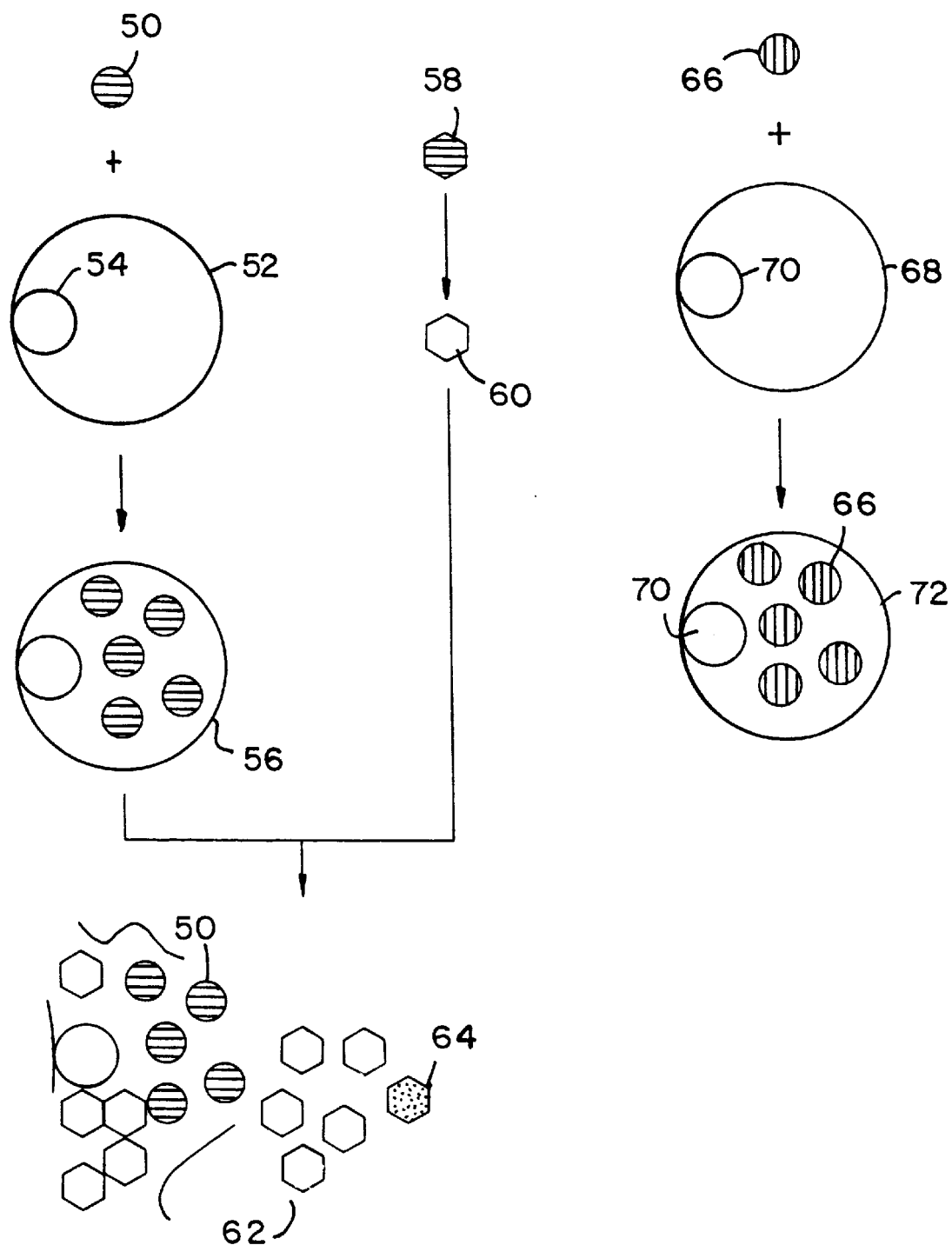
FIGS. 2A, 2B and 2C are schematic representations of a viral replicator embodiment of the invention for the creation or directed evolution of a gene which encodes a novel molecule.
Figure 2B:
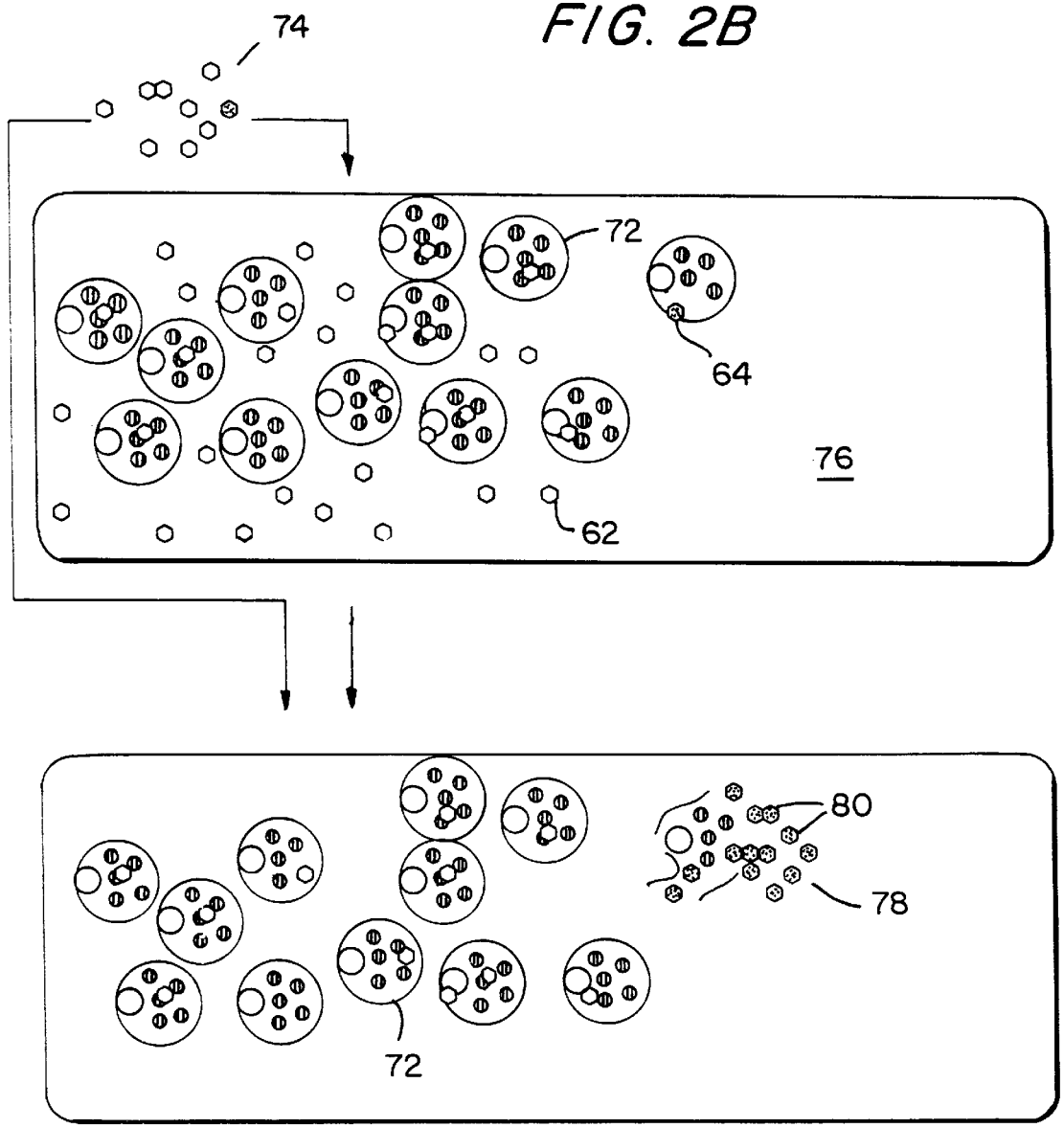
Figure 2C:
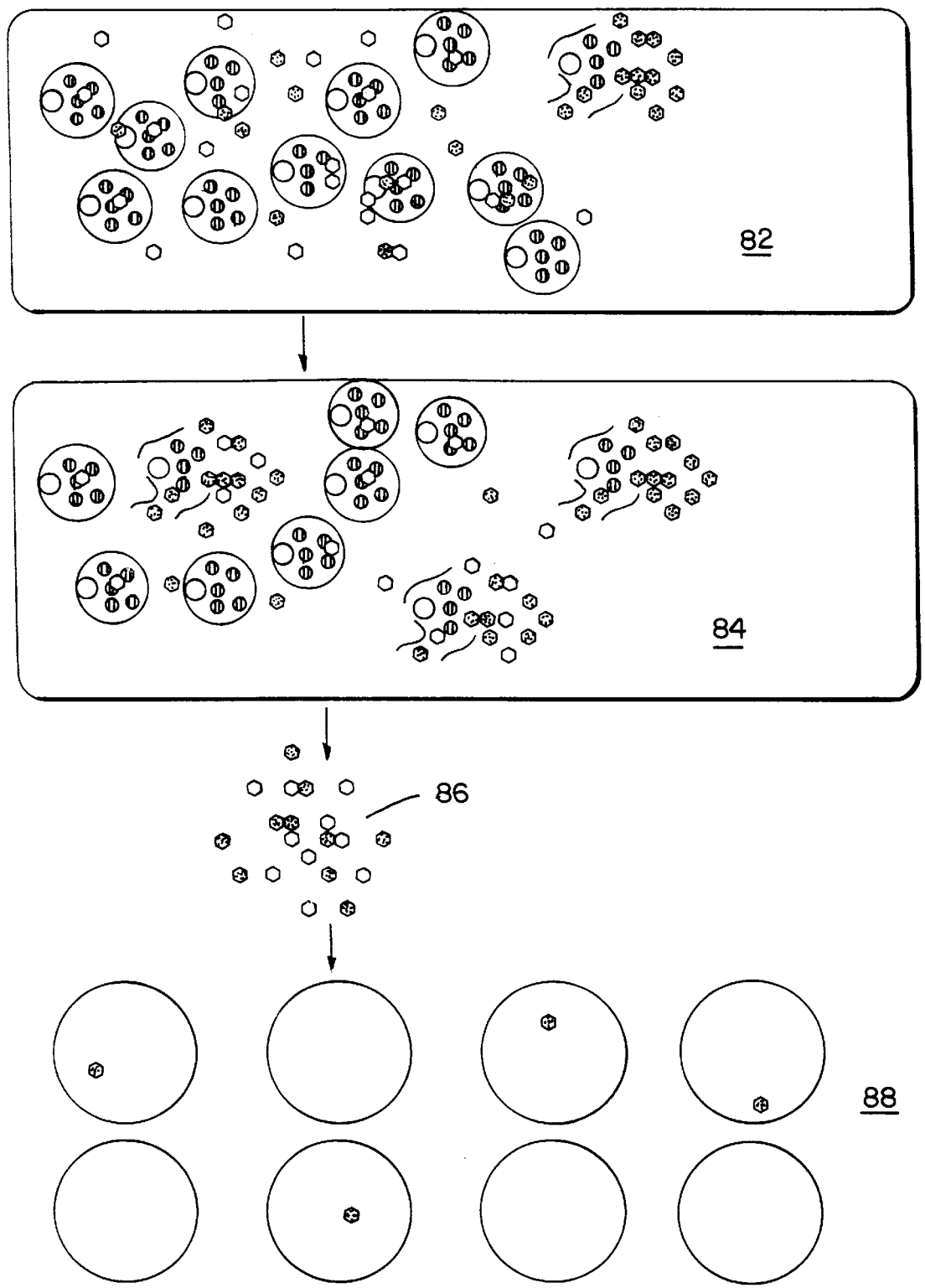

Referring to FIGS. 2A, 2B and 2C, reference numeral 50 refers to a plasmid carrying functional T7 bacteriophage genes. Plasmids 50 are introduced into E. coli host cell 52 having chromosome 54. The transformed host is shown at reference numeral 56.

Wild type T7 bacteriophage, is shown at reference numeral 58. A population, 60, of deletion mutant bacteriophage which do not encode a growth factor essential for replicator growth or replication, are engineered to encode putative novel molecules.

The heterogeneous population of T7 deletion mutants is introduced into transformed host cell 56 which complements the function of the T7 deletion mutants and a population of those deletion mutants are incubated. The population of deletion mutants is shown at reference numeral 62. The one T7 mutant within the population which carries the gene which expresses a novel molecule which is capable of the desired interaction is shown at reference numeral 64.

Reference numeral 66 refers to a plasmid carrying the genes which express a selection molecule containing the growth factor deleted from phage 60 and 64, a recognition sequence and a modulation moiety. Plasmid 66 is introduced into E. coli host cell 68 containing chromosome 70 thereby forming a second population of transformed E. coli hosts as shown at reference numeral 72.

The T7 deletion mutant population grown up in the first population of transformed host cells which complement their deletions, are then allowed to infect cells in the second population which expresses the selection molecules. The infection step is shown at reference numeral 74 and the incubation of the infected second population of host cells is shown at reference numeral 76. Viral replication occurs only in those host cells in which the novel molecule of desired function is expressed. The process can be carried out batchwise or additional amounts of mutant T7 bacteriophage can be added to the second population of transformed host cells in a continuous fashion, as shown, until cell lysis is monitored. The lysis of a cell in the incubated second population of transformed host cells is shown at reference numeral 78. As can be seen the population of T7 deletion mutants 64 which encodes the novel molecule of desired function has been substantially amplified as shown at reference numeral 80.

The viral population expressing the desired novel molecule expands and infects other cells upon cell lysis. No new T7 is added to the culture. The expansion and infection of other cells is shown at reference numeral 82. The multiple infections give rise to more virions which carry the desired novel molecule as well as those that do not carry the novel molecule. This is shown at reference numeral 84.

The selected and amplified viral population encoding the novel molecule of desired function shown at reference numeral 86 is isolated/purified from the cultivated host cells and then grown up on cells at low dilution which express the selection molecule. This separates out single viral clones carrying the genes which encode the novel molecule with desired function. This isolation/purification is shown at reference numeral 88.

Figure 3A:
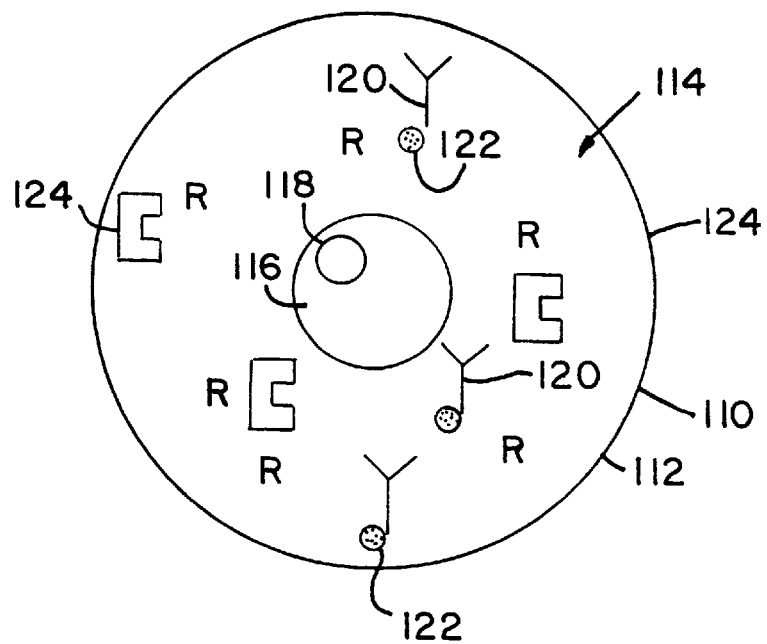
FIGS. 3A and 3B are schematic representations of a further embodiment of the invention for the creation or directed evolution of a novel hydroxylase based upon a binding interaction.
Figure 3A:
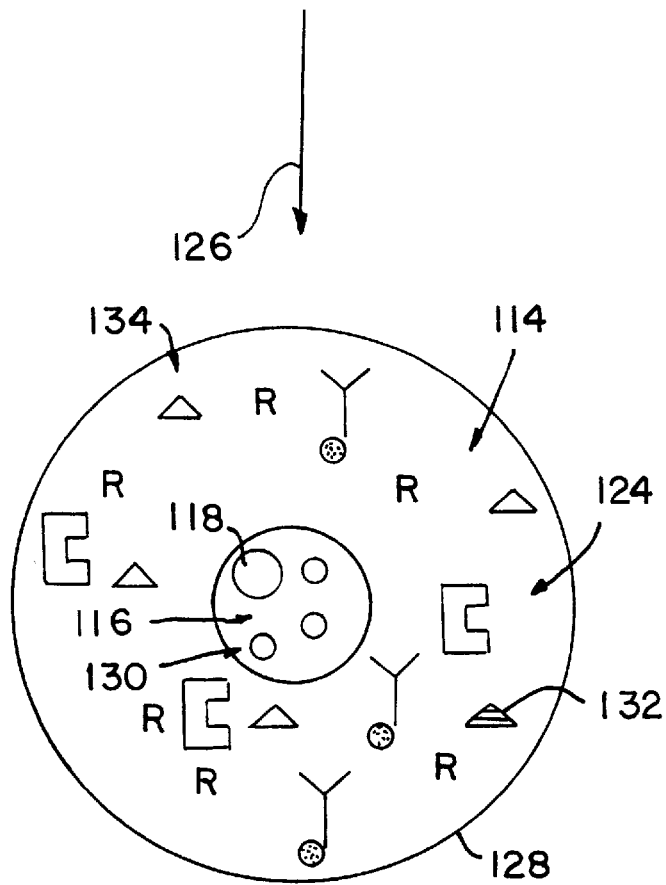
Figure 3B:
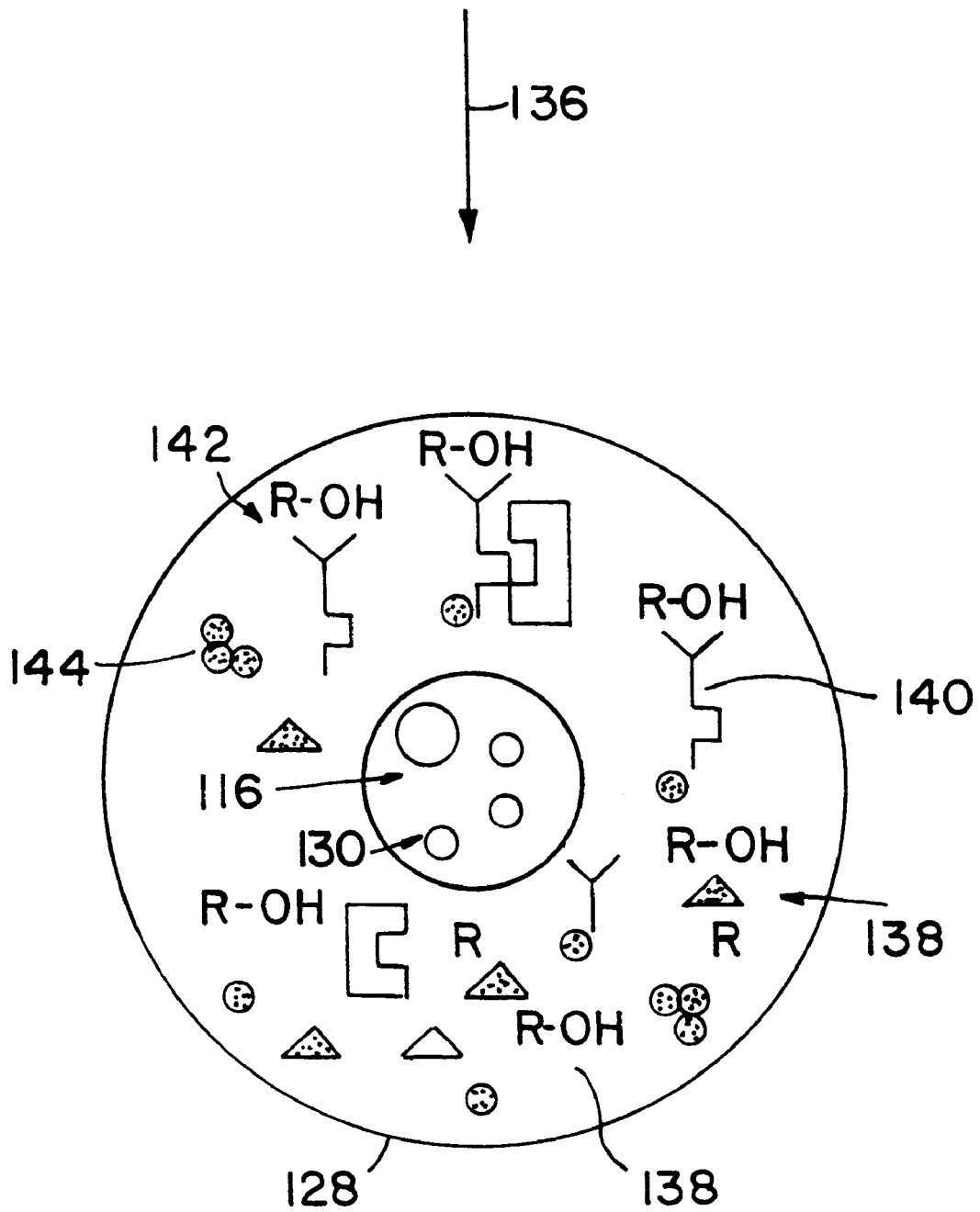

With reference to FIGS. 3A and 3B, the method depicted there is creation or directed evolution of a site-specific hydroxylase for the substrate represented by the formula R, i.e., a hydroxylase which can convert R to R—OH. Reference numeral 110 refers to a host cell (*E. coli*) having cell wall 112, periplasmic space 114, cytoplasm 116 and bacterial chromosome 118. Cell 110 contains substrate R in its periplasmic space as well as an antibody specific to the compound R—OH identified by reference numeral 120 to which is bound a modulated growth factor 122. Also in periplasmic space 114 is a protease 124 which is specific for the bound conformation of antibody 122.

The population of host cells 110 is transformed with plasmids which encode a heterogeneous population of hydroxylases which is replicated with low fidelity replication machinery. The step of infection is shown generally at reference numeral 126. The infected host cells, shown at reference numeral 128 contain multiple plasmids 130 in cytoplasm 116. These plasmids express a heterogeneous population of hydroxylases into periplasmic space 114. Those hydroxylases having the desired site-specific hydroxylase activity with respect to substrate R are shown at reference numeral 132 and non-desired hydroxylases are shown at reference numeral 134.

The population of transformed host cells are then incubated under selection conditions to select for and/or direct the evolution of the desired hydroxylase. This step is shown generally at reference numeral 136. The selected population of transformed host cells contains the hydroxylated substrate R, i.e., the compound R—OH as shown at reference numeral 138. In turn, antibody 120 binds the compound R—OH as shown at reference numeral 140. Protease 124, which is specific for the bound conformation of antibody 140, cleaves the modulated growth factor 122 from antibody 140 leaving the cleaved antibody 142 and the up-modulated growth factor 144 which confers a growth advantage on transformed host cell 128.

The selected population of transformed host cells 128 is then cultivated and the DNA isolated/purified. The DNA for the desired hydroxylase is cloned and the desired hydroxylase expressed and characterized.

DETAILED DESCRIPTION

The preferred embodiments of the invention are further described below with respect to the several particular features of the invention.

I. The Selection Molecule and its Component Parts

Selection molecules are used to direct selection pressure so as to obtain a desired gene. Selection molecules include growth factors and recognition sequences, and optionally modulation moieties. Some are capable of being used to select multiple different novel genes by utilizing the recognition sequence in a cassette-like fashion. Once a rational configuration of the desired components is established, steps are taken to prevent the mutation of the selection molecule. This provides a constant target for the population of novel molecules and serves to direct the selection or evolutionary process.

A. The Growth Factor

Growth factors are any factors capable of conferring a growth advantage or disadvantage upon a cell or replicator. Growth factors include nutrients such as carbon sources, nitrogen sources, energy sources, phosphate sources, inorganic ions, nucleic acids, amino acids, etc.; toxins such as antibiotics, inhibitors of enzymes critical for replication, detergents, etc.; enzymes which are essential for cell or replicator growth or which confer an advantage or disadvantage upon cellular growth, such as polymerases, ligases, topoisomerases, enzymes catalyzing reactions in the biosynthesis of proteins, etc.; molecules whose function is not catalytic but rather is structural or based on the binding capabilities of the molecule, such as actin, lipids, nucleosomes, receptors, hormones, cyclic AMP, etc.; and coenzymes or cofactors such as water, inorganic ions, NADPH, coenzyme A, etc.

B. The Recognition Sequence

The recognition sequence is a molecule or a portion of a molecule which interacts with the novel molecule. As such, recognition sequences may be a variety of different structures such as a sequence of amino acids or nucleic acids. This sequence may represent a unique sequence or it may represent a class of related sequences. The recognition sequence may also be a particular conformation or class of conformations of various molecules, e.g., a particular three dimensional structure of a protein, inorganic molecule, lipid, oligosaccharide, etc. In addition the recognition sequence may be an analog of any of the foregoing.

In addition, depending upon the selection system, the potential recognition sequences may be limited to a very specific region, conformation, sequence, etc., or may be a broad set of potential recognition sequences. For example, by using specific, multiple, redundant sequences in common to a plurality of selection molecules, with which the desired novel molecule may interact so as to modulate growth, the true recognition sequence is limited to that specific sequence common to all of the selection molecules. On the other hand, by using only one selection molecule or by using multiple selection molecules with large regions common to all, the potential recognition sequence may be a variety of regions, conformations, sequences, etc., within the one selection molecule or within the large regions common to multiple selection molecules. Recognition sequences thus may be highly specific to a region, conformation, sequence, etc., or be specific to a broader, yet defined set of regions, conformations, sequences, etc.

C. The Modulation Moiety

Central to the invention is the concept of modulation of the activity of the growth factor. There are many ways to modulate biological activity and nature has provided a number of precedents. Modulation of activity may be carried out through mechanisms as complicated and intricate as allosteric induced quaternary change to simple presence/absence, e.g., expression/degradation, systems. Indeed, the repression/activation of expression of many biological molecules is itself mediated by molecules whose activities are capable of being modulated through a variety of mechanisms.

A table of chemical modifications to bacterial proteins appears in (2), p. 73. As is noted in the table, some modifications are involved in proper assembly and other modifications are not, but in either case such modifications are capable of causing modulation of function.

In some instances modulation of functional usefulness may be mediated simply through the proper/improper localization of the molecule. Molecules may function to provide a growth advantage or disadvantage only if they are targeted to a particular location. For example, starch is a macromolecule which is typically not taken up by bacteria, so it is necessary to secrete enzymes responsible for its degradation, e.g., amylases, so that it may be converted into useable energy forms. Thus, production and retention of amylases within the bacteria down-modulates its functional usefulness when the bacteria is grown in a starch limiting media. It is only when the amylases are excreted that they are capable of conferring a growth advantage to the bacteria. The inherent enzymatic capabilities of the amylase may be the same inside or outside of the bacteria, but its functional usefulness is drastically down-modulated when it is targeted intra-cellularly relative to being targeted extra-cellularly.

Localization targeting of proteins carried out through cleavage of signal peptides is one way in which modulation of functional usefulness through molecular targeting is used within the invention. In this case, selection for a specific endoprotease catalytic activity is selected.

The functional usefulness of enzymes may also be modulated by altering their capability of catalyzing a reaction. Such a modulation may be carried out by differential localization (i.e., permissive local environment vs. non-permissive), but this need not be the mechanism. Illustrative examples of modulated molecules are zymogens, formation/disassociation of multi-subunit functional complexes, RNA virus poly-protein chains, allosteric interactions, general steric hindrance (covalent and non-covalent) and a variety of chemical modifications such as phosphorylation, methylation, acetylation, adenylation, and uridenylation ((2), p. 73, 315).

Zymogens are examples of naturally occurring protein fusions which cause modulation of enzymatic activity. Zymogens are one class of proteins which are converted into their active state through limited proteolysis ((3) p. 54). Nature has developed a mechanism of down-modulating the activity of certain enzymes, such as trypsin, by expressing these enzymes with additional "leader" peptide sequences at their amino termini. With the extra peptide sequence the enzyme is in the inactive zymogen state. Upon cleavage of this sequence the zymogen is converted to its enzymatically active state. The overall reaction rates of the zymogen are "about $10^5$–$10^6$ times lower than those of the corresponding enzyme" ((3) p. 54).

It is therefore possible to down-modulate the function of certain enzymes simply by the addition of a peptide sequence to one of its termini. For example, this property may be used within the invention to select for endoproteases with desired characteristics.

The formation or disassociation of multi-subunit enzymes is another way through which modulation may occur. Different mechanisms may be responsible for the modulation of activity upon formation or disassociation of multi-subunit enzymes. Two mechanisms are illustrative.

Tryptophan synthetase is composed of two different subunits, alpha and beta, in an alpha-beta-alpha-beta tetramer. The tetramer can disassociate into two alpha subunits and a beta-beta subunit each of which exhibit catalytic activity, however, the independent subunits are substantially less efficient than the tetrameric holoenzyme. The efficiency increase of the holoenzyme is thought to be due in part to the formation of a tunnel between the alpha and beta active sites (4). Through the determination of the three dimensional crystal structure of this enzyme it appears that the tunnel prevents the loss of the intermediate product of the alpha catalyzed reaction to the solvent by channelling it directly to the beta subunit active site thus increasing efficiency.

Modulation of activity upon formation of the holoenzyme for aspartate transcarbamoylase occurs through a different mechanism. In the aspartate transcarbamoylase holoenzyme the active sites are formed at the interface of catalytic subunits. In both aspartate transcarbamoylase and tryptophan synthetase the proper specific interaction of different subunits is critical for efficient activity of the holoenzyme. Therefore, sterically hindering the proper specific subunit interactions will down-modulate the catalytic activity. Such complexes could be used within the invention for the selection of a variety of molecules.

Other examples of mechanisms through which modulation of function may occur are RNA virus poly-proteins, allosteric effects, and general covalent and non-covalent steric hindrance. The HIV virus is a well studied example of an RNA virus which expresses non-functional poly-protein constructs. In the HIV virus "the gag, pol, and env poly-proteins are processed to yield, respectively, the viral structural proteins p17, p24, and p15—reverse transcriptase and integrase—and the two envelope proteins gp41 and gp120" (5). The proper cleavage of the poly-proteins is crucial for replication of the virus, and virions carrying inactive mutant HIV protease are non-infectious (5). This is another example of the fusion of proteins down-modulating their activity. Thus, it is possible to construct recombinant viruses which require sequence dependent endoproteases for proper replication.

Certain enzyme inhibitors afford good examples of functional down-modulation through covalent steric hindrance or modification. Suicide substrates which irreversibly bind to the active site of an enzyme at a catalytically important amino acid in the active site are examples of covalent modifications which sterically block the enzymatic active site. An example of a suicide substrate is TPCK for chymotrypsin (6). This type of modulation may be used in embodiments of the invention to select for compounds capable of covalently binding to catalytically active sites or cleaving moieties from a non-active catalytic site thereby converting it into a catalytically active one.

There are also examples of non-covalent steric hindrance including many repressor molecules. Lambda repressor is of interest since it simultaneously down-modulates the expression of other phage genes such as cro while up-modulating its own expression. It accomplishes this by non-covalently binding to DNA sequences and sterically hindering the interaction of these sequences with RNA polymerase thereby preventing RNA polymerase from transcribing towards the cro genes while simultaneously stimulating the RNA polymerase to transcribe in the opposite direction. Thus the repressor molecules are capable of sterically hindering and thus down-modulating the function of the DNA sequences by preventing particular DNA-RNA polymerase interactions.

The selection of non-covalent binding compounds offers possibilities and advantages because binding molecules can be created based on their ability to modify the activities of various substrates of interest.

Allosteric effects are another way through which modulation is carried out in some biological systems. Aspartate transcarbamoylase is a well characterized allosteric enzyme. Interacting with the catalytic subunits are regulatory domains. Upon binding to CTP or UTP the regulatory subunits are capable of inducing a quaternary structural change in the holoenzyme causing down-modulation of catalytic activity. In contrast, binding of ATP to the regulatory subunits is capable of causing up-modulation of catalytic activity (7). Using methods of the invention, molecules are selected which are capable of binding and causing modulatory quaternary or tertiary changes.

In addition, a variety of chemical modifications, e.g., phosphorylation, methylation, acetylation, adenylation, and uridenylation may be carried out so as to modulate function. It is known that modifications such as these play important roles in the regulation of many important cellular components. Reference ((2) p. 73) lists different bacterial enzymes which undergo such modifications. In addition, many proteins which are implicated in human disease also undergo such chemical modifications. For example, many oncogenes have been found to be modified by phosphorylation or to modify other proteins through phosphorylation or dephosphorylation. The ability to select for molecules based on their capability of altering the activity of a growth factor, e.g., by phosphorylation, is of importance.

D. Preferred Selection Molecules (1) Fusion or Deletion Molecules

Fusion proteins which incorporate the growth factor, the selection moiety and the recognition sequence are preferred selection molecules. Fusions may be between virtually any molecules, and may include the fusion of two molecules or multiple molecules. Fusions may include protein-protein fusions and protein-biomolecule fusions. The molecule may be a biological or chemical molecule or an ion. Sugars, nucleotides, nucleosides, fatty acids, small organic molecules and metal ions, e.g., Mg, and various derivatives and precursors of the foregoing may be considered. Other fusions may include protein-nucleic acid, protein-ribonucleic acid, protein-lipid, protein-oligosaccharide, nucleic acid-small molecule, small molecule-protein-lipid, nucleic acid-small molecule-lipid, among others.

If a protease is the molecule to be obtained a fusion construct of a metabolically important enzyme, i.e., the growth factor, with the desired peptide recognition sequence and with a bulky protein, i.e., the modulation moiety, may be made. Because of the steric hindrance and/or conformational changes caused by the peptide recognition sequence in conjunction with the bulky protein, the metabolically important enzyme is inactivated or functionally impaired. However, in the presence of the protease to be obtained the recognition sequence is cleaved and the enzyme's function is up-modulated.

The subunit embodiment and the alpha-beta type complementation embodiment are further variations of fusion constructs. The subunit embodiment exploits the complex multi-subunit nature of certain molecules. In some instances molecules are non-functional as monomers, but gain function in multi-subunit complexes comprising homogeneous or heterogeneous groups of molecules. One may fuse another molecule to any number of different subunits. Due to the often delicate and complex interactions of the subunits within the active multi-subunit form, modulation in function induced by constructing the fusion is likely to be quite strong.

The alpha-beta type complementation embodiment is conceptually similar. It is known that certain functional molecules may be fragmented and that the fragments alone do not function. The fragments may, however, re-associate and regain function. If the fragments are incorporated into fusions, these associations are prevented and accordingly these fusions are useful in the methods of the invention.

A 'reverse' subunit embodiment may also be used to create the fusion construct. In this case, the multi-subunit complexes lack function and the subunits themselves are functional. For example, by using a protein whose function is impaired by the addition of an extra sequence at one of its termini, it is possible to create a multi-subunit string of such proteins which are non-functional. By properly designing a linker sequence between the proteins, proteases of desired specificity can be obtained.

Under stringent selection conditions very slight advantages in the efficient use of resources can cause differential selection. If one member of the host cell population produces superfluous proteins, thus drawing on the amino acid pool unnecessarily, its growth will be disadvantaged. The reverse subunit methods may be efficient because wasted protein synthesis in the host cells producing the novel protease is eliminated since each subunit portion of the reverse subunit fusion molecule is utilized.

These fusion proteins may take on many different configurations and may be active or inactive, up-modulated or down-modulated. They may have protein groups or other groups such as phosphates or methyl groups added or deleted internally or at both termini. For example, protein sequences may be added to one or both or the termini or internally to a protein growth factor to modulate its function up or down and/or confer upon the selection molecule a particular desired recognition sequence.

A multiplicity of different groups may be added. For example a multi-protein fusion which consists of a large sterically hindering modulatory group linked to a recognition sequence linked to a growth factor linked to a recognition sequence linked to a large sterically hindering modulatory group may be used.

Alternatively, deletions may be utilized to construct modulated growth factors. For example, a protein growth factor which has a region whose presence is important to the proper function of the growth factor, may be used in a truncated or deleted form lacking this region, as a modulated growth factor. In another example a protein which is phosphorylated in its active form may be utilized in its unphosphorylated state as a modulated growth factor. In both cases normal molecules may be selected which introduce moiety (s) to the modulated growth factor.

(2) Allosteric Platforms

Selection molecules used to obtain novel molecules based on their binding capabilities may be designed in a multitude of ways. A simple binding based selection molecule may have its function modulated based on the binding of the novel molecule to a recognition sequence on the selection molecule. For example, a novel molecule may bind and or sterically inhibit the active site of an enzyme based selection molecule.

A selection molecule which when bound undergoes a conformational change may be referred to as an allosteric platform. The function of the growth factor may be modulated in an allosteric fashion. Thus, if the recognition sequence becomes bound either covalently or non-covalently, the function of the growth moiety is altered. The binding domain on the recognition sequence can be varied to accommodate the selection of a wide array of different ligands. The allosteric platform can be one molecule or many molecules, and can be used with any of the methods of the invention.

By way of example, one portion of the allosteric platform may serve as a receptor for binding a novel molecule and another portion may serve to link the allosteric platform to a growth factor. Upon binding of a novel molecule to the first portion, an allosteric change in the growth factor will result in up-modulations or down-modulations in function. The change in function can then be used to obtain the novel molecule by methods described elsewhere.

The novel molecule to be obtained need not actually bind the selection molecule nor is it necessary that the function of the novel molecule to be selected be binding. By way of example, a binding based selection molecule may be used to select for a novel molecule with virtually any catalytic activity. By having the binding based selection molecule recognize the product of the reaction catalyzed by the desired novel molecule, that novel molecule may be selected without itself interacting with the selection molecule.

II. Selection Methods

A. In General

The selection techniques used in the isolation, creation and directed evolution methods of the invention may be any of those heretofore employed in the art or may involve novel environments, conditions, procedures and selection pressures. Efforts should be made to limit the mutations of the genes which express the growth factor, the recognition sequence, the modulation moiety or the selection molecule so that a gene which encodes a novel molecule specific to the original and desired recognition sequence is obtained.

This is true in isolation, creation and directed evolution methods of the invention. In directed evolution it is desirable to mutate the genes having the evolutionary potential to encode novel molecules by exposure to external influences such as radiation or mutagenizing chemicals, or by the imposition of rationally designed selection conditions which impose an evolutionary direction on the putative novel molecule population. These methods are more fully described elsewhere.

Negative or positive selection methods may be employed. In positive selection, those members of the host or replicator population with the desired function have a selectable growth advantage. In negative selection, the reverse is true. Those members of the host or replicator population with the desired function have a selectable growth disadvantage. In negative selection, the gene of interest expresses a molecule which interacts with the selection molecule or recognition sequence to inhibit growth. Compounds, e.g., certain antibiotics can be administered to the population that kill or otherwise compromise members of the population if they are capable of growing. These techniques can be repeated in known cyclical fashion to enrich for the desired, non-growing members of the population.

It is important that selection conditions be directed at the specific selection characteristic of interest and it is important that the selection procedure be optimized. For example, it may be beneficial to apply selection pressure in a cyclical fashion, cycling between high and low selection pressure or to use different conditions to select for the same characteristic.

Different selection molecules and selection methods are used in different circumstances. For example, in gene isolation methods where it is thought that the gene which encodes the novel molecule having the desired properties exists within an existing gene pool, one time selection or repeated one time selection (batch selection) is appropriate to achieve isolation. In such circumstances it is desirable to use a growth factor that is absolutely essential for growth and which substantially or completely loses its function (maximal modulation of function) when incorporated in the selection construct. Since the desired novel molecule or a novel molecule very closely related to it, is thought to exist in the existing heterogeneous population and since only one or a very small number of related clones is selected, very stringent selection pressure is applied to the system.

Many generation selection techniques are used where the desired novel molecule is not thought to exist in the population and needs to be evolved. In certain instances, it is desirable to use a growth factor which is absolutely essential for growth, but whose function is only partly modulated, or a growth factor that is not absolutely essential, but which confers a growth advantage and can be fully modulated. This allows growth while the gene which expresses the novel molecule is evolved and then as molecules are produced with properties closely related to those of the desired novel molecule, a selective growth advantage is conferred.

These differences in the stringency of selection pressure through alternate selection molecule design for different novel molecule starting populations, are also created by altering environmental conditions. For example, using the same selection molecule, different levels of selection pressure are created simply by altering media, temperature, pH, etc. In some such examples, the effect of environmental conditions complements the selection molecule function and by changing these environmental conditions, differential selection pressures are established.

An alternative method, through which the selection molecules are used as the 'rheostat' of selection, includes altering the expression levels of the selection molecules. Simply increasing the expression levels of the selection molecules through an inducible promoter, may increase background in certain cases and thus decrease the selection pressure.

Two important techniques of the invention common to isolation, creation and directed evolution embodiments, are control of host cell mutations, and use of redundant selection molecules.

(1) Limitation of Undesired Mutations

It is important to control host cell mutations which affect the fidelity of expression of the growth factor and/or recognition sequence and/or modulation moiety and/or a selection molecule in order to maintain a constant target for interaction with a novel molecule. It is also important to limit background mutations, e.g., mutations in DNA within the entire selection system which may complicate selection for the desired novel molecule. Non-useful mutations of the genes which express the selection molecule or components thereof include those that confer the function of the growth factor through means other than the desired interaction of the novel molecules, e.g., proteolytic cleavage by a novel protease. Such mutations also include, among others, mutations of the growth factor portion of the fusion which negate the effects of the bulky group, mutations of the bulky group such that it becomes ineffective to modulate the function of the growth factor, transposition or recombination of the gene coding sequence for the growth factor which allows for the expression of an undesirably modulated growth factor, mutations (point mutations and insertions) that create promoters in front of the growth factor, development of the capability of post-translational or post-transcriptional modifications of the selection molecule so as to separate the component parts in a non-usable way thereby liberating the growth factor, and mutations that create alternate pathways or mutant molecules which carry out the same function as the growth factor.

Important considerations are the number and rate of specific mutations and the number and rate of gross mutations leading to specific insertions or deletions which give rise to non-useful species compared with the number of and rate specific and gross mutations necessary to generate a desired novel molecule. In directed evolution it is important that the number of specific mutations necessary to generate a gene which expresses a useful novel molecule be as low as possible and that the mutation rate be reasonably high relative to the number of mutations and the rate of mutation which give rise to non-useful mutants. If the probability of generating a non-useful gene mutation is 100 times that of generating a useful gene mutation, it is still possible, by running the experiment 100 times, to obtain a gene which expresses a useful novel molecule. This, however, is far from ideal.

For some genes, deletion rates may be as high as $10^{-4}$. This is dependent, among other considerations, on the particular gene sequence and surrounding sequences and the resulting secondary structure. The potential high probability of deletion mutations requires careful design to prevent occurrences giving rise to non-useful mutants. These occurrences may be minimized by proper selection of the gene sequence and secondary structure (both within the construct and locally) or by Rec A– and similar mutations which can reduce homologous recombination frequencies 1000 fold.

In addition high fidelity anti-mutator replication machinery may be used to reduce the frequency of mutation. It is known that certain polymerases may be mutated so they replicate with higher fidelity than the wild type polymerase. Such polymerases could be used so as to reduce the error rate during replication. Mutations may also be controlled by keeping the number of replications low or alternatively, if the cell cycle is arrested, to prevent further replication.

By segregating the genes which encode the selection molecule in certain embodiments it becomes simple to evolutionarily reset the selection molecules. For example, if the selection molecules are encoded in a host cell and the novel molecules are encoded by a replicator, it is possible to allow the selection procedure to evolve the genes encoded in the replicators. This evolved population may then be used in a selection procedure with a fresh population of host cells from an original starting culture. The components of the selection system encoded by the host cell for which mutations are undesirable are evolutionarily reset while the evolutionary progress of the novel molecule population is maintained and allowed to continue in a static selection environment.

(2) Use of Multiple Redundant Selection Molecules

Another method to enhance the selection of genes which express novel molecules over non-desirable mutants is through simultaneous use of multiple redundant selection molecules. In such systems a single non-desired mutant does not cause non-desirable selections because of the presence of the other selection molecules. Expression of the proper novel molecule affects all of the selection molecules and allows a useful selection to take place.

For example, a series of different protein-protein-protein fusions is produced, each with the same proteolytic cleavage site and different but essential growth factors. A mutation liberating one growth factor from its fusion and altering its function, will not cause a non-desirable selection or will result in marginal selection since the other selection molecules are not affected. If a novel molecule with the appropriate proteolytic properties is produced, each of the proteolytic cleavage sites is cut and each of the growth factors is liberated from its respective fusion and selection occurs.

The level of redundancy is also used to modulate selection pressure. Through different levels of redundancy, it is possible to change the total number of cleavages necessary for the production of a given species. For example, if seven different growth factors are complexed in seven different redundant selection molecules, more cleavages are necessary than if just three of those seven components were used.

Even more important is the type of component. For example, some components in the replication process of bacteriophage are catalytic and need relatively few total copies to accomplish their task. Other components are non-catalytic and require many more cleavages. Examples of such components are head and tail proteins, structural proteins involved in the function of virions. If the head and tail proteins are complexed in a selection molecule, huge numbers of cleavages would be necessary since each protein of the assembled viral coat would have to be cleaved. This type of selection construct would place a higher burden on the novel molecules because higher turnover would be necessary to produce significant quantities of viral progeny.

Two important aspects of the invention common to the creation and in particular to the directed evolution embodiments are segregation of the genes which encode the selection molecules and which encode the putative novel molecules and effecting controlled mutation of the latter, and using several evolutionary starting points for the genes which express putative novel molecules.

(3) Segregation of the Genes which Encode the Selection Molecule and which Encode the Putative Novel Molecules and Effecting Controlled Mutation of the Genes which Encode Putative Novel Molecules It is desirable to bias the selection methods by segregating, e.g., in time or space or by different recognition sequences, the genes which encode putative novel molecules and the selection molecule, respectively, in such a way as to allow each to be replicated by different replication systems which have different mutation rates. This allows the gene pool for potential novel molecules to develop or evolve at an increased rate. The stability of the selection molecule is maintained while allowing the genes which may encode novel molecules to evolve.

The genes which encode putative novel molecules may initially consist of one gene to be mutated and evolved into a gene which expresses a novel molecule with the desired function, or, a population of genes can be mutated and evolved so as to obtain a gene which expresses a molecule with the desired function. The starting molecular population may or may not be structurally or otherwise related to the novel molecule ultimately sought.

The methods of the invention may be carried out by using low fidelity replication machinery and by using different types of coding materials and by employing various process conditions which control the mutation rates. Sequence repair mechanisms which differentially affect the genes which express putative novel molecules and selection molecules or their components can also be used. Applying different environmental conditions such as temperature, pressure, pH, ion and substrate concentration effects, etc., can also be used to achieve these objectives. The controlled mutation rate may also be created by using certain coding materials, e.g., known 'hot spots' within chromosomes where mutation rates are higher than in other locations.

Physically separate coding sequences with distinct mutation rates and/or distinct replication machinery likewise, are used. These include, among others, host chromosomal DNA, plasmid DNA (circular or self replicating short sequence), viruses (both DNA and RNA), short self replicating RNA sequences or plasmids and mitochondrial DNA. These and other coding sequences can be used in any combination to code for the selection molecules and the putative novel molecules. These different coding vehicles can be replicated at different mutation rates by using different replication machinery with different specific origins of replication.

Another way in which differential mutation rates may be created is through replication timing and turnover. If, for instance, replication occurs at a faster rate for the sequence encoding the novel molecule than for the selection molecule, both using replication machinery of the same fidelity, the novel molecule population will develop higher numbers of mutations. In addition, timing of the synthesis of different components to different replication machineries may be used to create different mutation rates. For example, it is known that the E. coli chromosome is replicated in a controlled fashion and certain proteins such as DnaA are needed to initiate replication. Therefore, it may be possible to have a system in which two DNA polymerases, with different mutation rates, are controlled by inducible or cyclically activated promoters. The synthesis of the polymerases and the DnaA type proteins can be timed so that a high fidelity polymerase replicates the selection molecule on the host chromosome, for example, and a low fidelity polymerase replicates the novel molecule on a viral chromosome. In certain embodiments such a system may have identical origins of replication.

(4) Number of Evolutionary Starting Points and Mutation of Gene Populations

Several different methods may be used to develop a population of genes which express novel molecules. No evolutionary starting points, one evolutionary starting point or multiple evolutionary starting points may be used.

Selection systems designed with no evolutionary starting points may be used to select for the desired gene of interest based simply on the selection molecules introduced into the host. Such methods select for naturally occurring genes within the components of the selection system, e.g., genes from the host cell or replicator. In this method, one draws upon the evolutionary potential inherent within the host or replicator rather than introducing specific molecule(s) to be used as evolutionary starting points. Another method using no evolutionary starting point comprises introducing a population of molecules which are wholly or partially stochastically generated and are thus previously unknown. In this case the evolutionary potential of these stochastically generated molecules is exploited in the production of genes which express a novel molecule.

Two examples of methods which employ one evolutionary starting point are where a foreign gene is chosen and introduced into the host or replicator based on the evolutionary potential of that gene, and where a gene is chosen together with members of the gene's sub-species, e.g., closely related variants thereof.

Lastly, multiple evolutionary starting points may be utilized. In this case multiple genes are chosen based on their evolutionary potential. The genes may be mutagenized so as to diversify its sub-species. This allows for the creation of a novel gene population which is heterogeneous but is, at the same time, a highly focused rationally designed population based on desired evolutionary potentials.

By way of example, in the development of a catalyst with a particular reaction type and specificity, one chooses evolutionary starting points which are most likely to have the highest evolutionary potential of giving rise to the desired catalyst. One chooses genes which express molecules which already possess characteristics similar to those of the desired catalyst, e.g., molecule(s) with similar specificity for recognition sequences to that of the desired catalyst. Alternatively, one chooses a molecule(s) of the same or similar reaction type (e.g., proteolysis, hydroxylation, etc.) as that of the desired catalyst. By making rational choices of the types of evolutionary starting points a greater evolutionary potential for the gene population and therefore shorter evolutionary distance to reach the desired gene is achieved, i.e., less mutations are required to arrive at the desired gene. Suitable evolutionary starting points are enzymes, antibodies, catalytic antibodies, T-cell receptors and MHC molecules.

Different methods of mutation exist and may be used alone or in conjunction with one another. One method is the use of mutagenizing compounds or conditions such as chemical mutagens or UV irradiation. Alternatively, site directed mutagenesis techniques may be used. Methods of site directed mutagenesis are described in (1). Other methods to increase the number of mutations within the population include the use of low fidelity replication machinery and high rates of replication.

In another technique, short stochastic sequences of DNA can be introduced around the coding region of the active site of an enzyme and the population subjected to chemical and/or UOS irradiation. This population may then be replicated by low fidelity replication machinery at a high frequency to rapidly create a highly heterogeneous population.

In another example, the new molecules are coded on a viral genome and a large population of such viruses is subjected to a mutagen(s) or to mutagenizing conditions, including, but not limited to, in vitro chemical mutagenesis, site directed mutagenesis, recombination, transposition, UV or light induced mutation, PCR mediated mutation, stochastically generated mutation (as described in U.K. Specification No. GB 2183661A) low-fidelity replication and high replication frequency. The viral population then codes for a multiplicity of different new molecules.

In another example, a non-lytic phage, e.g., M13, encoding the new molecule is allowed to replicate with a low fidelity polymerase, while DnaA is not produced. Expression of the low fidelity polymerase is turned off and expression of a high fidelity polymerase and DnaA is turned on and the E. coli chromosome encoding the fusion is replicated as well. This process is repeated in a cyclical fashion so as to continually promote a higher mutation rate in the novel molecule population.

(5) Other Methods for Control of Selection Pressure to Promote Directed Evolution It is also beneficial to cycle the genes encoding the novel molecule population between high and low selection conditions or even between selection conditions and permissive conditions to promote evolution of the genes. For example, modified viruses are incubated cyclically between two strains of E. coli, a high selection pressure strain, and a low selection pressure strain, so that if marginal growth occurs in the high selection pressure strain through the production of a low specificity or low turnover novel molecule, the population is expanded in the low selection pressure strain, mutagenized and then again subjected to high selection pressure. This cycle is repeated to help promote the evolution of the novel molecule population towards the desired specificity.

Depending on the stability of the high selection pressure strain and the mutation rate of the selection molecules, a continuous or semi-continuous system is developed. In a continuous system, modified viruses are continuously produced in the low selection pressure strain. Free virions are collected, mutagenized and a portion reintroduced into the low selection pressure incubation chamber so as to increase the heterogeneity of the novel molecule population beyond the level of what might arise through low fidelity replication alone. The remainder is incubated with the high selection pressure strain. The low selection pressure strain incubation chamber is reinoculated with fresh bacteria periodically or the conditions are controlled to be such that the replication rate of that strain relative to that of the virus is sufficient to maintain the bacterial population.

In certain embodiments in which growth factors essential for the replication of the virus are down-modulated, the high selection pressure bacteria in a continuous system will not need to be replenished until a novel molecule with some degree of the desired specificity is produced. This is because the infection of a modified virus with a gene which encodes a novel molecule not having the ability to cleave the selection molecule is abortive. It is only when the selection constructs are cleaved and function is regained in the virus replication machinery that infection progresses through the lytic cycle. Once a novel molecule with some capabilities of the desired molecule is produced, viral growth is promoted. Selection is continued toward the desired specificity, reaction type and turnover rate by continuously adding fresh high selection pressure bacteria to the incubation chamber. The high selection pressure bacteria added is grown directly from aliquots of the original high selection pressure bacteria so that the bacterial population is evolutionarily reset. Alternatively, selection methods may use non-lytic phage.

For directed evolution, the novel molecule population is based on the sequence for a molecule, e.g., protease that has characteristics most similar to those of the desired novel molecule, e.g., activity, specificity, turnover, etc. since in certain embodiments the gene population encoding the novel molecule may be derived from a single source, mutagenesis and low fidelity replication is important in developing a suitably heterogeneous population. In addition, selection pressure may be adjustable and/or cyclical to aid in the evolution of genes which encode the desired novel molecule. Other important techniques for promoting directed evolution are increasing the heterogeneity of the novel molecule population by increasing the total number of replications of genes encoding the population and use of mutator low-fidelity polymerases.

By way of example, the evolutionary starting point for the novel molecule may be a particular protease which recognizes a specific sequence which is not deleterious to the system. However, in certain embodiments it is advantageous to have multiple novel molecule starting points. Thus, several different proteases, of the same or different families, may be initially encoded in the modified viruses. If multiple novel molecule starting points are used, then starting points which are close to the desired catalytic activity or specificity, or both, may be incorporated.

B. Host Selection Methods (1) Positive Selection

Positive cellular selection may occur in a variety of ways. In one example a cellular growth factor which confers a growth advantage to the cell is functionally down-modulated. The down-modulated cellular growth factor is complexed in a selection molecule so that upon production of the desired novel molecule the growth factor is functionally up-modulated. Thus selection of the desired novel molecule occurs through positive cellular selection.

Alternatively, a toxin is incorporated into a selection molecule so that its function is maintained or up-modulated. The functionally maintained or up-modulated toxin is complexed in a selection molecule so that upon production of the desired novel molecule the growth factor is functionally down-modulated. Selection of the desired novel molecule again occurs through positive cellular selection.

Such positive cellular growth selection techniques may be carried out in a variety of different apparatuses including chemostats, turbidostats, in simple incubation chambers with appropriate media and under correct conditions, etc.

(2) Negative Selection

Negative cellular selection may occur in a variety of ways. A cellular growth factor which confers a growth advantage on the cell has its function maintained or up-modulated when complexed in a selection molecule. Upon production of the desired novel molecule and the interaction of same with the selection molecule, the growth factor is functionally down-modulated. Thus selection of the desired novel molecule occurs through negative cellular selection.

In another example, a toxin is incorporated into a selection molecule so that its function is down-modulated. Upon production of the desired novel molecule, however, the toxin is functionally up-modulated. Again, selection of the desired novel molecule occurs through negative cellular selection.

Negative cellular selection is carried out using methods such as growth in the presence of a molecule such as an antibiotic which preferentially kills growing cells. By cyclically passing the cells from antibiotic containing media to non-antibiotic containing growth media, cells which are incapable of growing may be selected.

C. Replicator Selection Methods (1) Positive Replicator Selection

In embodiments of the invention which exploit positive selection for replicators, e.g., viruses, the gene to be isolated, created or evolved and its gene pool or its mutations are encoded within the population of replicators. The viral population is allowed to infect host cells. Those virus particles with the gene which expresses the novel molecule are given a preferential growth advantage (lytic pathway) or integration advantage (lysogenic pathway). If viral replication is the selectable characteristic, a selection molecule may be made using essential proteins involved in viral replication which are functionally down-modulated in the selection molecule. A gene which encodes a novel molecule is then obtained based on its interaction with a recognition sequence and the resultant up-modulation of the growth factor and consequent viral replication.

Positive viral selection offers a number of inherent advantages. Viruses are highly efficient carriers of vast numbers of coding sequences and provide a convenient way to physically segregate coding material. In addition, because some viruses encode their own replication machineries and origins of replication, high and low fidelity replication systems may operate simultaneously (one for the virus and one for the host). Viruses also replicate at rates faster than bacteria. This allows for large differentials in the number of replications per unit time between the host and the virus which may cause a difference in the total number of mutations. It is therefore possible to promote positive selection and variability, i.e., high mutation rate in the population encoding the novel molecule, and homogeneity, i.e., low mutation rate in the population encoding the selection molecules, thereby minimizing selection of non-useful mutants.

A method of the invention which exploits viral positive selection and host cell negative selection may be performed by creating a modified bacteriophage which encodes the novel molecule and a first modified strain of *E. coli* which encodes the selection molecule. The modified phage does not encode all of the necessary components for its replication. Those replication components not encoded in the modified phage are encoded in the first modified *E. coli* strain in selection molecules which modulate their function.

The modified phage encoding the putative novel molecules are produced in a second modified strain of *E. coli* before selection with first strain. A modified bacteriophage, lacking a crucial component(s) for its replication will not replicate in a typical host cell and therefore the second strain, which encodes and produces the component(s) lacking in the modified phage is created to produce a large population of modified phage for selection with the first strain Selection pressure may be placed on the viruses in a continuous or semi-continuous flow cell culture or alternatively standard viral assays may be performed. If the conditions and/or the dilutions are correct, cell negative selection may also be used. In this case the viruses which carry the gene which expresses the molecule to be isolated, created or evolved have a selective advantage within the host cells which may confer a selective disadvantage on the host cell. The methods described for negative selection can then be used to select for the infected cells.

(2) Negative Replicator Selection With Host Positive Selection

Selection of the gene of interest may be carried out by negative selection for replicator growth and/or replication and/or positive selection for host cell growth. Lytic viruses may be used with host cells which encode a viral growth factor which confers a growth advantage on the virus when complexed in a selection molecule but which confers a selective disadvantage upon the virus when the desired novel molecule is expressed and interacts with the selection molecule to release the growth factor. Such a selection molecule can be an enzyme essential to viral replication with a recognition sequence inserted within the enzyme which does not down-modulate the activity of the enzyme. Upon interaction with the desired novel molecule and cleavage of the recognition sequence the viral replication enzyme becomes functionally down-modulated. The viruses are negatively selected and the host cells undergo positive selection.

D. Multiple-Replicator Methods

Multiple replicators may also be used within the same host, i.e. the different components of the selection method may be encoded by different populations of replicators. For example different replicators may encode one or more of: the putative novel molecule population, the recognition sequence, the modulation moiety, the selection molecule, etc. Different viruses and plasmids may be used in conjunction with one another to create a heterogeneous population of genes which encode novel molecules.

Such methods for the isolation, creation or directed evolution of a gene which encodes a novel molecule capable of a desired interaction with a substrate of interest comprises expressing in one or more populations of replicators within a population of host cells multiple copies of a putative novel molecule or a multiplicity of putative novel molecules, a growth factor for one or more of said populations of replicators which express said novel molecules, and a substrate of interest or analog thereof functionally associated with said growth factor, and, optionally, a modulation moiety for said replicator growth factor, and imposing selection conditions, e.g., incubating the population of host cells under selection conditions, to select for replicators which express a novel molecule which interacts with said analog to alter the activity of said growth factor.

The order of expression of the several components is a matter of choice as is the relative timing of expression and the imposition of selection conditions. It is also possible, as in other embodiments of the invention to exogenously add one or more of said growth factor, recognition sequence or modulation moiety.

E. Disease Cell Based Selection

Selection methods may also be carried out directly in disease state cells. For example, cancer cells may be used as hosts which encode a selection molecule which in turn permits selection for novel molecules which retard cancer cell growth. By way of illustration, a cancerous cell which improperly phosphorylates an important cellular enzyme in cell cycle control thus giving rise to the cancerous phenotype may be used as a host. Selection may be carried out for novel molecules which are capable of reverting the cancerous phenotype. The novel molecules thus selected may then be assayed in normal cells of the same type as the cancerous cells for toxicity or deleterious side effects. The methods of the invention may be used within disease state cells so as to select for molecules which revert the disease state to normal phenotypes.

F. Selection Based on the Recognition of the Products Formed Through the Interaction of a Novel Molecule Antibodies (or fragments thereof) are capable of exquisite specificity and are capable of resolving very slight differences in molecular structure, allowing them to recognize virtually any molecule specifically. Other binding molecules include T-cell receptors, MHC molecules and lectins.

The ability of antibodies to bind to virtually any antigen in an exquisitely specific manner has been well documented and can be used to advantage in carrying out the methods of the invention, e.g., for the isolation, creation or directed evolution of a site specific hydroxylase for the conversion of a drug RH to ROH (8). An advantageous method is described in FIG. 3 and is further described below.

It is first necessary to obtain small amounts of the desired product or an analog of this product through isolation/purification or chemical synthesis so that monoclonal antibodies specific for, in this example, the hydroxylated drug ROH, can be produced through protocols such as those in (9). The antibody can then be expressed in its functional conformation in *E. coli* by extension of the techniques of (10), (11), and (12). This recombinant antibody is further developed as described later to link its binding of ROH to cellular growth.

An important attribute of some classes of antibodies is that the constant region of the antibody undergoes conformational change upon binding. This conformational change is evident, for example, in the IgM class of antibodies. Frank et al., in their chapter on complement in (13) state "binding [of antigen] facilitates a conformational change in the antibody". Such conformational changes are further described in (14), (15), and sub-referenced in (15), are (16) and (17). In addition it is known that conformational changes may contribute to antibody binding (18). These conformational changes can be used to link product formation and subsequent antibody binding to growth modulation.

This tie in to growth rate modulation may be elaborated in a variety of different ways. A protein whose function is highly modulated based on the conformation of the attached constant region (i.e., bound or unbound) may be used. Or, in a preferred example, the tie in to cellular growth is through the attachment of a protein whose function is modulated based on whether or not it is covalently attached to the constant region. Such a protein might be a protein which is active only in a multi-subunit holoenzyme, or a peptide sequence which is active only when not sterically hindered, or a sequence which is active in areas not accessible to a large antibody. An example is the multi-subunit aspartate transcarbamoylase, an essential gene for pyrimidine nucleotide synthesis. This enzyme is composed of twelve polypeptide chains and its catalytic activity is modulated by conformational change (19). Enzymes such as aspartate transcarbamoylase, which are highly complex and whose catalytic activity is highly sensitive to conformation are good candidates since their function can be modulated when their subunits are complexed to a large antibody molecule. In addition, in aspartate transcarbamoylase an active site is formed at the interface of two subunits. Methods for the ligation of the aspartate transcarbamoylase subunit genes to the recombinant antibody constant regions are referenced in Example I.

To obtain the novel molecule capable of producing the desired specifically hydroxylated drug ROH, cell selection in pyrimidine nucleotide limiting conditions is carried out in a host strain which requires aspartate transcarbamoylase function for efficient growth and is deficient for non-specific proteases. Cleavage of the aspartate transcarbamoylase from the antibody constant region occurs when the antibody binds ROH. This is accomplished through the use of a protease specific for the conformation of the antibody constant region when the antibody is bound to its antigen. The specific protease is developed using techniques of the invention. The aspartate transcarbamoylase is cleaved from the selection molecule and allowed to form its active multi-subunit form when the antibody is bound to its antigen, i.e., the drug, ROH, catalyzed by the desired hydroxylase.

The conformational change induced by binding may be approached in different ways. The close packing of antibodies upon cross-linking through antigen grouping or linking can also give rise to conformational changes. One might target closely packed antibodies' quaternary or tertiary structure. In a related method in which close packing of antibodies would not normally occur dummy antibodies may be used which bind to epitopes other than the desired one but which are spatially close to the desired epitope. Thus, upon binding of antibodies to the desired epitope antibody close packing conformational changes will occur.

Embodiments of the invention based on the recognition of products formed through the interaction of a novel molecule include the selection of novel kinases, phosphatases and methylases or a molecule capable of uridenylation, adenylation, hydroxylation or glycosylation, among others.

G. Control of the Activity Level of Novel Molecules by Control of the Expression Levels of Putative Novel Molecules Novel molecule selection pressure can be controlled by setting the level of expression of the putative novel molecules. If an enzyme of desired function is to be developed, one may use the level of expression of the putative novel molecules to direct the desired turnover rate of the novel molecule. If high turnover rate is to be selected, the expression of putative novel molecules is controlled at a low level. Alternatively, if low turnover rate is desired, the expression of putative novel molecules is controlled at a high level. Even more specifically, if high turnover rate is desired, a selection molecule may be used which ensures that a high number of novel molecule reaction events, relative to the number of novel molecules present in the system at any one time (considering also their rate of synthesis and rate of degradation) are required per unit time to confer selectability. Thus, selection pressure may be exerted by appropriately setting the number of putative novel molecules present at any given time.

H. Selection of Certain Proteases

The host cell or replicator selection methods of the invention can be carried out to isolate, create or direct the evolution of novel proteases which are capable of cleaving certain substrates of therapeutic interest.

Examples of such recognition sequences are epitopes of influenza haemagglutinin. The following sequences, among others can be incorporated in a selection molecule.

Site A amino acids 140–146, Lys-Arg-Gly-Pro-Gly-Ser-Gly (SEQ ID NO:1) or Lys-Arg-Gly-Pro-Asp-Ser-Gly (SEQ ID NO:2) or Lys-Arg-Gly-Pro-Asp-Asn-Gly (SEQ ID NO:3), or Site B amino acids 187–196 Thr-Asp-Gln-Glu-Gln-Thr-Ser-Leu-Tyr-Val (SEQ ID NO:4) or Thr-Asn-Gln-Glu-Gln-Thr-Ser-Leu-Tyr-Val (SEQ ID NO:5) or Thr-Asn-Lys-Glu-Gln-Thr-Asn-Leu-Tyr-Val (SEQ ID NO:6), or Site C amino acids 273–279 Pro-Ile-Asp-Thr-Cys-Ile-Ser (SEQ ID NO:7) or Pro-Ile-Gly-Thr-Cys-Ile-Ser (SEQ ID NO:8) or Pro-Ile-Asp-Thr-Cys-Ser-Ser (SEQ ID NO:9), or amino acids 52–54 Cys-Asn-Asn (SEQ ID NO:10) or Cys-Asp-Asn (SEQ ID NO:11) or Cys-Asn-Lys (SEQ ID NO:12)

Other examples of such recognition sequences are the following sites of HIV gp120

(a) variable region 3, amino acids 271–295 N-N-T-R-K-S-I-R-I-Q-R-G-P-G-R-A-F-V-T-I-G-K-I-G-N (SEQ ID NO:13)

(b) conserved domain 4, amino acids 392–402 Q-F-I-N-M-W-Q-E-V-G-K (SEQ ID NO:14)

(c) conserved domain 5, amino acids 452–474 E-L-Y-K-Y-K-V-V-K-I-E-P-L-G-V-A-P-T-K-A-K-R-R (SEQ ID NO:15)

Proteases to variants of such sequences can be produced. Alternatively, redundant selection molecules with the same basic conformation of such sequences can be used to select for proteases which are generally specific to their overall conformation.

I. Use of Combinations of Recognition Sequences and Genes Which Express Putative Novel Molecules Combinations of recognition sequences and genes which express putative novel molecules may be used. Two different recognition sequences can be used in each of two redundant sets of selection molecules together with genes which express two putative novel molecule populations which are differentiated by their evolutionary starting points. A novel molecule is obtained from the first population which reacts with one of the recognition sequences, and a novel molecule is obtained from the other population which reacts with the other recognition sequence.

In anther example a selection molecule which incorporates two closely related recognition sequences, A and A' is used. Interaction with both of the recognition sequences by the desired novel molecule is required to confer some degree of selectability. Selection may be carried out for reactivity to both recognition sequences simultaneously. This may occur by selection of one molecule with broad specificity for A and A', or of two molecules, one with specificity for A and the other for A'. In either case reactivity to both A and A' is simultaneously selected. In a similar method, multiple selection molecules may be used in which one set of selection molecules contain A and another contains A' in multiple redundant selection molecules.

J. Cell-Free Methods

The invention may also be carried out in cell-free methods. A preferred embodiment of a cell-free method is disclosed in FIGS. 4A and 4B.

Figure 4A:
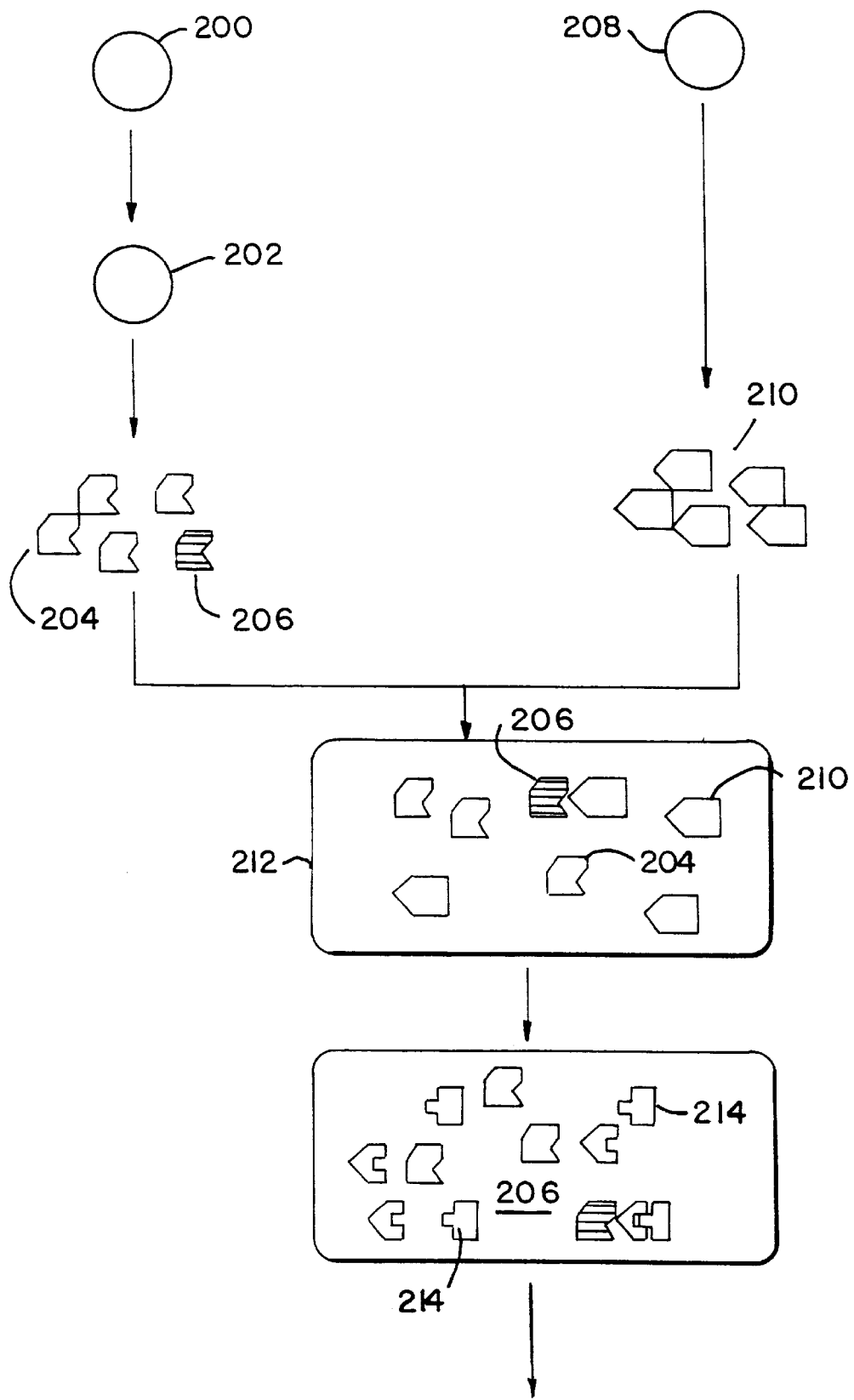
FIGS. 4A and 4B are schematic representations of a cell-free embodiment of the invention.
Figure 4B:
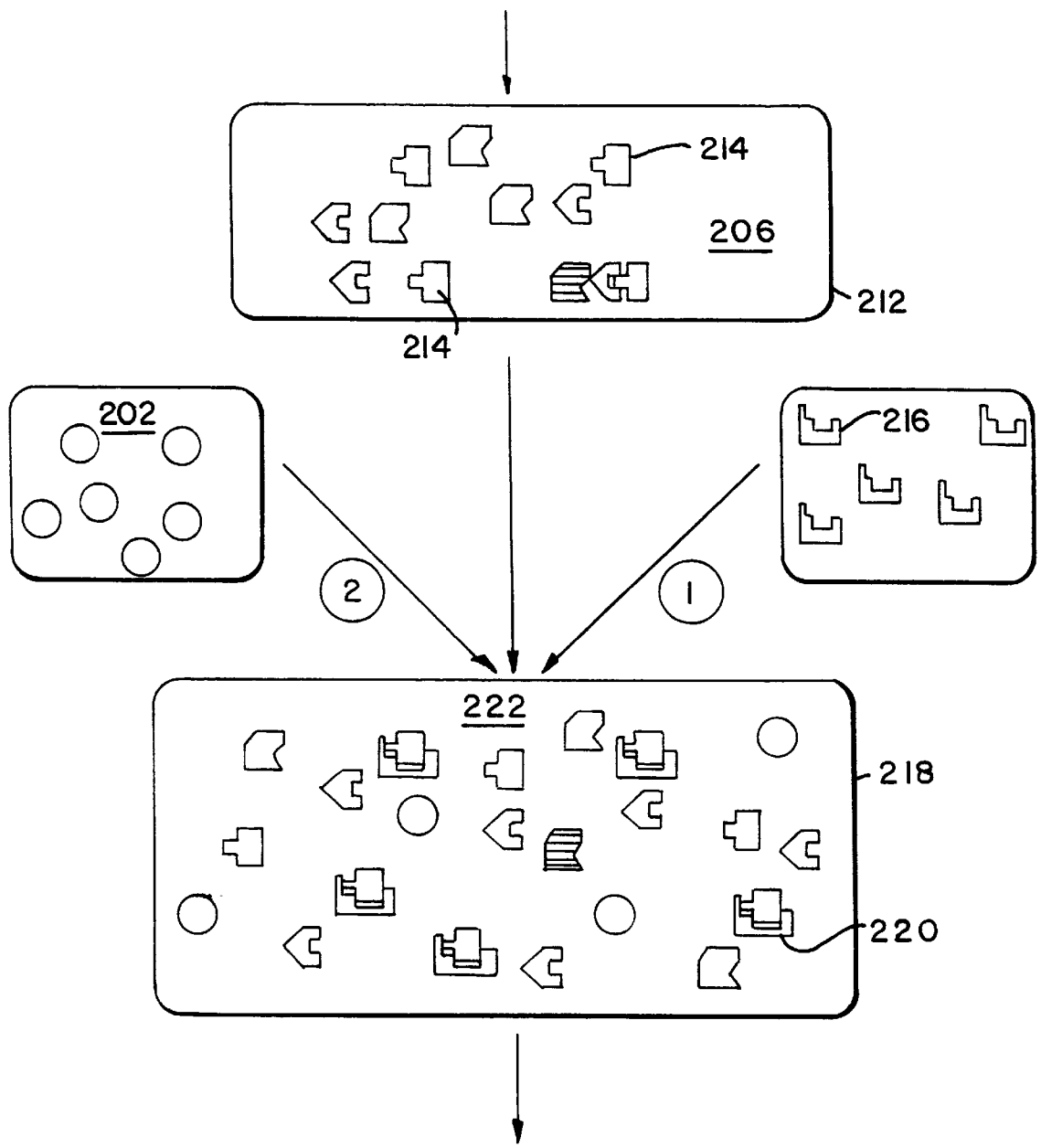

Referring to FIGS. 4A and 4B, reference numeral 200 identifies DNA which encodes multiple copies of putative novel molecules or a multiplicity of different putative novel molecules. DNA 200 is subjected to mutagenesis thereby forming a heterogeneous population of DNA encoding a multiplicity of different putative novel molecules 202. Population 202 is transcribed and translated to express a multiplicity of different putative novel molecules 204. Reference numeral 206 identifies a novel molecule of interest within that population.

Reference numeral 208 refers to DNA which encodes a selection molecule which includes actin as a growth modulation moiety and a recognition sequence which is or represents the substrate of interest. DNA population 208 is transcribed and translated to express a population of selection molecules 210.

The population 204 of putative novel molecules is then incubated with the population of selection molecules 210 in an incubator 212. Incubation of the putative novel molecules and the selection molecules results in enzymatic cleavage of the recognition site within the selection molecules by the desired novel molecule 206 thereby releasing actin monomer 214 from the selection molecule. After that reaction has gone to completion, DNase 216 is added to the reaction mixture and the mixture is incubated in incubator 218 for a time sufficient to permit the liberated actin, if any, to inhibit the DNase. An excess of the incubated mixture from incubator 212 is used with respect to DNase 216, to ensure that all of the DNase is inhibited. The actin monomers inhibit the DNase as shown at reference numeral 220. Then, after the actin has been inhibited, the heterogeneous population of mutated DNA encoding a population of different putative novel molecules 202 is added to the incubated mixture of the multiplicity of different putative novel molecules, the actin-based selection molecule and Dnase and that mixture is further incubated in incubator 218. The presence of the desired novel molecule is assayed by the presence of non-degraded DNA.

The DNA may be isolated/purified, partitioned, expressed and re-assayed for the desired functions of the novel molecule. In a preferred method, the isolated/purified DNA is amplified, e.g., by a polymerase chain reaction (PCR) and the amplified DNA subjected to one or more repetitions of the method to select for the desired DNA.

The invention is further described in the following examples.

EXAMPLE I

Creation of Novel Protease(s) for a Decapeptide Sequence from HIV gp120 through the use of Artificial Zymogens and Viral Positive Selection Example I describes a method to create endopeptidase(s) specific for a decapeptide recognition sequence from gp120. The method uses gene fusions which encode protein based selection molecules. Novel proteases encoded in a viral population cleave the decapeptide recognition sequence thereby releasing proteins necessary for viral replication. This example is representative of viral positive selection. A simplified representation is set forth in FIGS. 2A, 2B and 2C.

*E. coli* B, a host strain for bacteriophage T7, is transformed by the introduction of a plasmid so as to complement T7 deletion mutants. Two different deletion mutant T7 strains are made and so two corresponding *E. coli* complementary transformants are produced as listed below:

1) *E. coli* Transformant 1 (ET1) is transformed with *E. coli* plasmid pKK177-3 carrying the sequence for the inducible expression of T7 genes gpl (RNA polymerase), gp 4 (primase/helicase), and mutant gp 5 (DNA polymerase) with low fidelity and reduced 3'-5' exonuclease activity. This transformed host, upon induced expression of these genes, allows for the growth of a T7 deletion mutant (T7A) for genes gp 1, 4, and 5.

2) *E. coli* Transformant 2 (ET2) is transformed with *E. coli* plasmid pKK177-3 carrying the sequence for the inducible expression of T7 genes gp1, gp 4, mutant gp 5 with low fidelity and reduced 3'-5' exonuclease activity, and in addition gene 10A (major head protein), 13 (internal virion protein), and 18 (DNA maturation protein). This transformed host upon induced expression of these genes allows for the growth of a T7 deletion mutant (T7B) for genes 1, 4, 5, 10A, 13, and 18.

In addition two *E. coli* Selection Transformants (EST1 and EST2) are produced. These transformed cell lines differ from ET1 and ET2 in that the T7 genes encoded in these cells are complexed as gene fusions. In addition, these strains are selected for protease deficiency (e.g., strains such as lon, hfl, or htpR) (1) and (20). These two transformants are described below:

1) *E. coli* Selection Transformant 1 (EST1) is transformed with *E. coli* plasmid pKK177-3 carrying the sequence for the expression of T7 genes gp1, gp 4, and mutant gp 5 with low fidelity and reduced 3'-5' exonuclease activity all of whose sequences have modulation moieties (virion structural coat proteins from T4) fused to both their amino and carboxy termini as outlined in the table below connected through a gp120 protease recognition sequence.

2) *E. coli* Selection Transformant 2 (EST2) is transformed with *E. coli* plasmid pKK177-3 carrying the sequence for the inducible expression of T7 genes gp1, gp 4, mutant gp 5 with low fidelity and reduced 3'-5' exonuclease activity, and in addition genes 10A (major head protein), 13 (internal virion protein), and 18 (DNA maturation protein), all of whose sequences have modulation moieties (virion structural coat proteins from T4) fused to both their amino and carboxy termini as outlined in the table below connected through a gp120 protease recognition sequence.

| T7 gene | amino terminal T4 gene | carboxy terminal T4 gene |
| --- | --- | --- |
| 1 | 7 | 20 |
| 4 | 27 | 23 |
| 5 | 14 | 15 |
| 10A | 18 | 12 |
| 13 | 17 | 24 |
| 18 | 3 | hoc |

The complete sequence of T7 is elucidated in (21). Using the information from the T7 sequence, primers are chemically synthesized for the PCR mediated amplification of the genes to be inserted into the plasmids. Example PCR primers for each gene are listed below with the numbers corresponding to the T7 DNA sequence given in (21),

| gene | Primer A | Primer B |
|------|----------|----------|
| 1 | 3171–3185 | 5806–5820 |
| 4 | 11565–11579 | 13249–13263 |
| 5 | 14353–14367 | 16451–16465 |
| 10A | 22966–22980 | 23987–24001 |
| 13 | 27306–27320 | 27706–27720 |
| 18 | 36552–36566 | 36805–36819 |

PCR amplification of each of these genes is carried out through standard techniques such as those described in (1). T7 wild type phage and their DNA which are used as a template are isolated/purified by the following method as described by (22) and (23).

The T7 genes once amplified, are ligated into plasmid vectors with inducible promoters such as p-KK177-3, a vector which utilizes the tac promoter. The tac promoter is turned off in E. coli strains which express high levels of the lac repressor. The promoter is induced through the addition of isopropylthio-β-D-galactoside (IPTG) to a final concentration of 1 mM. p-KK177-3 as well as the tac promoter are discussed in (1). Ligation of the T7 genes amplified by PCR into a plasmid containing an inducible promoter such as p-KK177-3 can be carried out through standard ligation techniques described in (1). The recombinant plasmids are then used to transform an E. coli B strain, which expresses high levels of the lac repressor, through techniques such as electrotransformation or by using calcium chloride. Protocols for these techniques are described in (1).

Gene fusions are commonly used in molecular biology and a variety of different methods for the construction of β-galactosidase fusion proteins have been described in (24). These methods or the methods described in (1) referred to earlier are used to form a properly ligated selection molecule composed of a T7 gene with a T4 structural coat protein gene attached to both the amino and carboxy termini so that the reading frames are maintained throughout the construct. Thus each of the T7 genes in EST1 and EST2 are encoded without stop codons prematurely terminating the fusion protein or inserted or deleted bases shifting the reading frame. The T4 DNA sequences may be located and isolated/purified using the T4 genome map reproduced in (25). The needed genes are then PCR amplified for use in ligation procedures as was described for the T7 genes previously. DNA molecules encoding the fusions may then in turn be ligated into pKK177-3 plasmid DNA under the control of the tac promoter.

The protease recognition sequence is a decapeptide around Trp 397 of the fourth constant region of gp120 of the HIV virus. This amino acid is very important for the binding of gp120 to CD4 as mutants of gp120 at this position abrogate CD4 binding. From the sequence of gp120 from (26), a desired proteolytic recognition sequence can be determined such as FINMWQEVGK (SEQ ID NO:16) (Phenylalanine-Isoleucine-Asparagine-Methionine-Tryptophan-Glutamic acid-Valine-Glycine-Lysine). The nucleotide encoding sequence is obtained from (27) in which the nucleotide sequences from five different HIV clones are described each of which has Trp 397.

There are at least four different methods which can be used to generate the T7 deletion mutants. These methods include using specific restriction enzymes if appropriate, creating unique restriction sites by oligonucleotide-mediated mutagenesis, deletion by oligonucleotide-mediated "loop-out" mutagenesis, and the generation of systematic deletions. These techniques are outlined in (1). The T7 viral genome is obtained as described previously in (22) and (23). The T7 deletion mutant genomes are then properly packaged into virions in vitro following the protocols of (28).

The initial population of novel molecules is based on several known proteases. This allows for several different evolutionary starting points from which the desired novel molecule can arise. The proteases are HIV protease, polio3C protease, and subtilisin BPN'. The sequences for these proteases have been introduced into *E. coli* and expressed as functional enzymes or enzymes with functional potential in zymogen state (29) and (30).

To generate a large and heterogeneous putative novel molecule population, each protease gene is subjected to site directed mutagenesis as well as in vitro chemical mutagenesis. Methods for site directed mutagenesis are given in (1). Methods for in vitro chemical mutagenesis are also given in (1).

The mutagenized novel molecules are then ligated to a promoter such as bacteriophage lambda PR or PL promoters (for use in hosts which do not express lambda repressor to down-regulate novel molecule production) or a T7 promoter through methods discussed earlier. The promoter/novel molecule population is then ligated into the T7A deletion mutant population grown in ET1 host cells following the procedures above. Once this procedure is complete a heterogeneous T7A deletion mutant population is produced which is highly heterogeneous by virtue of the fact that it encodes a heterogeneous mutagenized pool of novel molecules. This population is referred to below as T7A/novel molecule.

The T7A/novel molecule population is then grown up on ET1 host cells and transferred to EST1 host cells. The EST1 host cells for the T7A/novel molecule population are kept in stationary non-replicating growth phase. Only those T7A/novel molecule virions which are capable of producing a novel molecule which restores gp1, gp 4 and gp 5 function by cleaving the gp120 decapeptide protease recognition sequence are then able to liberate the T4 virion structural coat protein groups from the selection molecule thus allowing growth in these hosts. T7A/novel molecule are added in a continuous fashion using a cellstat as described in (31), or in a semicontinuous batch process adding repeated aliquots of the T7A/novel molecule to the EST1 hosts. Once viral replication occurs the resulting virions are harvested and their DNA isolated/purified as described in (22) and (23). The novel molecule sequence is obtained either through PCR amplification if the recognition sequences of the primers have not been prohibitively mutated, through isolation/purification of fragments of the T7/novel molecule gene which are capable of hybridizing with DNA encoding wild type novel molecules, or through isolation/purification of fragments capable of expressing molecules with the desired function.

The sequence coding for the novel molecule from the T7/novel molecule virion capable of growing in EST1 is then expressed in any of a number of expression systems, (1), and the protease can then be more accurately characterized functionally. If further selection is necessary the sequence for the novel molecule from the T7A/novel molecule virion capable of growing in EST1 is ligated into T7B. Thus procedures are carried out as before except T7B is used instead of T7A, ET2 is used instead of ET1, and EST2 will be used instead of EST1.

The procedure of Example I thus permits the development of a novel proteases specific for the decapeptide sequence from gp120.

EXAMPLE II

Creation of Novel Protease(s) for β-Galactosidase Through the Use of Artificial Zymogens Example II describes a method to create endopeptidase(s) with a range of specificity for recognition sequences around the carboxy terminus of β-galactosidase. The method employs a gene fusion involving β-galactosidase and a T7 gene. The selection procedure is based on a novel molecule (protease) cleaving the β-galactosidase which up-modulates the T7 product function necessary for viral replication. Therefore this example represents a viral positive selection procedure. The procedure is generally represented in FIGS. 2A, 2B and 2C.

Specifically, β-galactosidase in the correct reading frame, is ligated to the amino terminus of each of the T7 genes that are encoded in EST1 and EST2 without stop codons prematurely terminating the fusion protein. The DNA encoding the fusions are then inserted into the pKK177-3 plasmid under the control of the tac promoter.

E. coli B, a host strain for bacteriophage T7, is transformed by the introduction of plasmids encoding T7 genes so as to complement T7 deletion mutants. This allows for the growth and amplification of these T7 deletion mutants. Two different deletion mutant T7 strains are made and so two corresponding E. coli complementary transformants are produced as described in Example I. In addition the corresponding selection strains, EST1 and EST2 but with β-galactosidase fused to the amino termini of the T7 genes used, are then utilized in the selection procedures.

There are no constraints on the proteases other than to cleave enough of the β-galactosidase so as to liberate the function of the T7 genes in constructs. In this respect the desired novel molecule is 'semi-specific'. However, the protease itself may be specific for a particular recognition sequence. One skilled in the art would realize that this technique might be used to develop proteases with specificity for recognition sequences with proteins other than β-galactosidase.

1) E. coli Transformant 1 (ET1) is transformed with E. coli plasmid PKK177-3 carrying the sequence for the inducible expression of T7 genes gp1 (RNA polymerase), gp 4 (primase/helicase), and mutant gp 5 (DNA polymerase) with low fidelity and reduced 3'-5' exonuclease activity. This transformed host, upon induced expression of these genes, allows for the growth of a T7 deletion mutant (T7A) for genes gp 1, 4 and 5.

2) E. coli Transformant 2 (ET2) is transformed with E. coli plasmid pKK177-3 carrying the sequence for the inducible expression of T7 genes gp1, gp 4, mutant gp 5 with low fidelity and reduced 3'-5' exonuclease activity, and in addition gene 10A (major head protein), 13 (internal virion protein), and 18 (DNA maturation protein). This transformed host upon induced expression of these genes allows for the growth of a T7 deletion mutant (T7B) for genes 1, 4, 5, 10A, 13 and 18.

In addition two E. coli Selection Transformants (EST1 and EST2) are produced. These transformed cell lines differ from ET1 and ET2 in that the T7 genes encoded in these cells are complexed as gene fusions. In addition, these strains are selected for protease deficiency (e.g., strains such as lon, hfl, or htpR) (1) and (20). These two transformants are described below:

1) E. coli Selection Transformant 1 (EST1) is transformed with E. coli plasmid pKK177-3 carrying the sequence for T7 genes gp1, gp 4, and mutant gp 5 with low fidelity and reduced 3'-5' exonuclease activity each of which is ligated to β-galactosidase so that upon expression the modulation moiety β-galactosidase is fused to their amino termini.

2) E. coli Selection Transformant 2 (EST2) is transformed with E. coli plasmid pKK177-3 carrying the sequence for T7 genes gp1, gp 4, mutant gp 5 with low fidelity and reduced 3'-5' exonuclease activity, and in addition genes 10A (major head protein), 13 (internal virion protein), and 18 (DNA maturation protein) each of which is ligated to β-galactosidase so that upon expression the modulation moiety β-galactosidase is fused to their amino termini.

The complete sequence of T7 is elucidated in (21). Using the information from the T7 sequence, primers can be chemically synthesized for the PCR mediated amplification of the genes to be inserted into the plasmids. Example PCR primers for each gene are listed below with the numbers corresponding to the T7 DNA sequence given in (21).

| gene | Primer A | Primer B |
| --- | --- | --- |
| 1 | 3171–3185 | 5806–5820 |
| 4 | 11565–11579 | 13249–13263 |
| 5 | 14353–14367 | 16451–16465 |
| 10A | 22966–22980 | 23987–24001 |
| 13 | 27306–27320 | 27706–27720 |
| 18 | 36552–36566 | 36805–36819 |

PCR amplification of each of these genes can be carried out through standard techniques such as those described in (1). T7 wild type phage and their DNA which will be used as a template may be isolated/purified by the following method as described by (22) and (23).

The T7 genes once amplified may be ligated into plasmid vectors with inducible promoters such as p-KK177-3, a vector which utilizes the tac promoter. The tac promoter is turned off in E. coli strains which express high levels of the lac repressor. The promoter is induced through the addition of isopropylthio-β-D-galactoside (IPTG) to a final concentration of 1 mM. p-KK177-3 as well as the tac promoter are discussed in (1). Ligation of the T7 genes amplified by PCR into a plasmid containing an inducible promnoter such as p-K-KI77-3 can be carried our through standard ligation techniques described in (1). The recombinant plasmids are then used to transform an E. coli B strain, which expresses high levels of the lac repressor, through techniques such as electrotransformation or by using calcium chloride. Protocols for these techniques are described in (1).

β-galactosidase is a commonly used gene in molecular biology and a variety of different methods for the construction of βgalactosidase fusion proteins have been described (24). These methods or the methods described in (1) referred to earlier may be used to form a properly ligated β-galactosidase, in the correct reading frame, to the amino terminus of each of the T7 genes that will be encoded in EST1 and EST2 without stop codons prematurely terminating the fusion protein. DNA molecules encoding the fusions may then in turn be ligated into pKK177-3 plasmid DNA under the control of the tac promoter.

There are at least four different methods which can be used to generate the T7 deletion mutants. These methods include using specific restriction enzymes if appropriate, creating unique restriction sites by oligonucleotide-mediated mutagenesis, deletion by oligonucleotide-mediated "loop-out" mutagenesis, and the generation of systematic deletions. These techniques are outlined in (1). The T7 viral genome is obtained as described previously in (22) and (23). The T7 deletion mutant genomes are then properly packaged into virions in vitro following the protocols of (28).

The population of novel molecules is based on several known proteases. This allows for several different evolutionary starting points from which the desired novel molecule could arise. The proteases to be used are HIV protease, polio3C protease, and subtilisin BPN'. The sequences for these proteases have been introduced into E. coli and expressed as functional enzymes or as enzymes with functional potential (29) and (30).

To generate a large and heterogeneous putative novel molecule population each protease gene is subjected to site directed mutagenesis as well as in vitro chemical mutagenesis. Methods for site directed mutagenesis and methods for in vitro chemical mutagenesis are given in (1).

The mutagenized novel molecules are then ligated to a promoter such as bacteriophage lambda PR or PL promoters (for use in hosts which do not express lambda repressor to down-regulate novel molecule production) or a T7 promoter using methods discussed earlier. The promoter/novel molecule population is then ligated into the T7A deletion mutant population grown in ET1 host cells following the procedures above. Once this procedure is complete, a heterogeneous T7A deletion mutant population ( T7A/novel molecule) is produced which is highly heterogeneous by virtue of the fact that it encodes a heterogeneous mutagenized pool of novel molecules.

The T7A/novel molecule population is then grown up on ET1 host cells and transferred to EST1 host cells. The EST1 host cells for the T7A/novel molecule population are kept in stationary non-replicating growth phase. Only those T7A/novel molecule virions which are capable of producing a novel molecule which restores gp1, gp 4 and gp 5 function by cleaving the β-galactosidase groups from the selection molecule are capable of growing in these hosts. The T7A/novel molecule virions are added in a continuous fashion using a cellstat as described by (31), or in a semicontinuous batch process adding repeated aliquots of the T7A/novel molecule virions to the EST1 hosts. Once viral replication occurs the resulting virions are harvested and their DNA isolated/purified as described by (22) and (23). The novel molecule sequence is obtained either through PCR amplification, if the recognition sequences of the primers have not been prohibitively mutated, through isolation/purification of fragments of the T7/novel molecule gene which are capable of hybridizing with DNA encoding wild type novel molecules, or through isolation/purification of fragments capable of expressing molecules with the desired function. The sequence coding the novel molecule from the T7/novel molecule virion capable of growing in EST1 is then expressed in any of a number of expression systems, (1), and the protease can then be more accurately characterized functionally. If further selection is necessary the sequence for the novel molecule from the T7A/novel molecule virion capable of growing in EST1 is ligated into T7B. Thus procedures are carried out as before except T7B is used instead of T7A, ET2 is used instead of ET1, and EST2 is used instead of EST1.

This procedure allows for the development of a protease generally specific to cleave the carboxy terminal region of βgalactosidase.

EXAMPLE III

Methods to Select Novel Protease(s) Specific for an Epitope of Influenza Haemagglutinin Example III describes a method to create an endopeptidase which cleaves specifically a heptapeptide sequence from influenza haemagglutinin (HA) site A (amino acids 140 to 146) (32) The method employs gene fusions involving T7 genes (whose function is down-modulated when complexed in the fusion) and genes from other bacteriophage. The selection procedure is based on a novel molecule (endoprotease) cleaving the influenza HA heptapeptide recognition sequence and thereby up-modulating the function of the T7 product necessary for viral replication. This example represents a viral positive selection procedure. A simplified representation of the method appears in FIGS. 2A, 2B and 2C.

The heptapeptide recognition sequence is composed of the amino acids 140 to 146 of an influenza HA, AICHI/2/68. The sequence is Lys-Arg-Gly-Pro-Gly-Ser-Gly (SEQ ID NO:17).

Two strains EST1* and EST2* and are produced which encode the heptapeptide sequence as recognition linkers used in the manner in which the factor X recognition sequence (33) and the V8 recognition sequence system (34) are used. In addition these strains are selected to be protease deficient. In these systems specific sequences for particular proteases are placed between two genes to be cleaved. The constructs for EST1* and EST2* are based on EST1 and EST2 described in Example I, but with the specific influenza HA heptapeptide sequence described above. The fusions and novel molecule populations are constructed and expressed as described earlier. Similar selection protocols are then followed.

Thus, upon production of an novel molecule capable of cleaving the influenza HA heptapeptide, the T7 genes are released from their constructs. Since the heptapeptide recognition sequence is the only common sequence between all of the fusions, novel molecule selection is directed towards proteases which are specific only for the influenza HA heptapeptide. First novel molecules are selected on EST1* followed by selection on EST2* as described in Example 1 for EST1 and EST2. The resultant novel molecules carried in T7B are isolated/purified and characterized.

One skilled in the art will realize that this technique may be used to develop proteases with specificity for recognition sequences other than the one used in this example.

EXAMPLE IV

Method of Creating a Novel Hydroxylase Based on Antibody Binding

Example IV describes a method to create a molecule capable of hydroxylating an organic molecule, R, at a specific site. The method employs the use of antibodies capable of binding specifically to R—OH. A simplified representation of the method steps appears in FIGS. 3A and 3B.

The antibodies are complexed in fusions with the catalytic subunit of aspartate transcarbamoylase attached to their constant region. Upon binding their antigens, antibodies undergo conformational change. The bound antibodies are cleaved by an endoprotease (designed using methods described elsewhere in the application) capable of recognizing the conformation of the bound antibody. The released aspartate transcarbamoylase catalytic subunits form multi-subunit complexes thus functionally up-modulating the aspartate transcarbamoylase activity, and thus conferring a selectable advantage on the cell. Therefore molecules capable of catalyzing the desired hydroxylation may be selected.

In this example the reaction of interest is the site specific hydroxylation of a drug RH to ROH as shown in (35). Small amounts of the desired product, R—OH, or an analog of this product are produced through isolation or chemical synthesis so that monoclonal antibodies specific for the hydroxylated form ROH can be produced through protocols such as those in (36). The genes for the antibody with the desired specificity are ligated to the gene for the catalytic sub-unit of aspartate transcarbamoylase at the constant region of the antibody's heavy chain gene. These constructs are then expressed in their functional conformation in E. coli by extension of the techniques of (10), (11), and (12). These E. coli are selected for the requirement of functionally active aspartate transcarbamoylase for efficient growth and they are selected to be protease deficient.

The novel molecule population is based on a hydroxylase cytochrome p-450. The gene is mutated so as to create a heterogeneous population of mutant hydroxylases through a variety of techniques described earlier. The genes are then inserted into a plasmid under the control of low fidelity T7 replication machinery. The plasmids are transfected into the cells expressing the antibody fusion protein. The resultant cells are grown in a chemostat in pyrimidine limiting media. The genes for the hydroxylases encoded in the selected cells are isolated/purified, cloned and the functional characteristics of the relevant hydroxylase is determined.

One skilled in the art will realize that this technique may be used to develop molecules with a variety of functional characteristics other than the ability to act as a hydroxylase. In addition, one skilled in the art will realize that molecules other than antibodies which undergo conformational change upon binding might be tied in through a variety of mechanisms to confer a growth advantage or disadvantage.

EXAMPLE V

A Method for Creating a Novel Endopentidase Using Cellular Positive Selection

Example V describes a method to create an endopeptidase which cleaves specifically a decapeptide sequence from gp120. A simplified representation appears in FIGS. 1A and 1B.

The method employs gene fusions involving three cellular genes, aspartate transcarbamoylase, glutamine synthetase, and tryptophan synthetase (whose functions are downmodulated when complexed in the fusion) in selection molecules with various genes from other bacteriophage. The selection procedure is based on a novel molecule (endoprotease) cleaving the gp120 decapeptide recognition sequence and thus up-modulating the three cellular genes' functions and therefore giving the cells containing the endopeptidase with the desired function a growth advantage under selection conditions. This example represents a positive cellular selection procedure.

The genes for virion coat proteins 24 and 18 of bacteriophage T4 are fused to the amino and carboxy termini respectively of glutamine synthetase through a protease peptide recognition sequence from gp120 used in Example I. Similarly virion coat proteins 27 and 20 are fused with the gp120 linker to the amino and carboxy termini respectively of the alpha subunit of tryptophan synthetase and gene 12 of T7 and gene F from phiX174 are fused with the gp120 linker to the amino and carboxy termini respectively of the beta subunit of tryptophan synthetase. Lastly proteins from gene 23 and 15 of bacteriophage T4 are fused with the gp120 linker to the amino and carboxy termini respectively of the catalytic subunit of aspartate transcarbamoylase, and proteins from gene 27 of bacteriophage T4 and gene 16 of bacteriophage T7 are fused with the gp120 linker to the amino and carboxy termini respectively of the regulatory subunit of aspartate transcarbamoylase. Aspartate transcarbamoylase catalyzes the formation of N-carbamoyl-aspartate from carbamoyl phosphate and aspartate.

These constructs can be fabricated with appropriate promoters and expressed using ligation techniques described in Example I, and then incorporated into the *E. coli* chromosome of a strain of *E. coli* which is a deletion mutant for the aspartate transcarbamoylase, glutamine synthetase, and tryptophan synthetase genes. These *E. coli* are additionally selected for the requirement of functionally active aspartate transcarbamoylase, glutamine synthetase, and tryptophan synthetase for efficient growth and are also selected for protease deficiency.

These *E. coli* are then grown in glutamine, tryptophan and pyrimidine rich medium. The novel molecule genes based on the three proteases from Example I are mutated as before. In this example, however, the resulting heterogeneous population of genes which express putative novel molecules is ligated into a high copy plasmid such as the PUC vectors (e.g., pUC18, pUC19, pUC118, and pUC119) described in (1), which is under the control of mutant low fidelity T7 replication machinery. Plasmids whose replication is under the control of T7 replication machinery are described in (37).

In this example the plasmid encodes multiple novel molecule genes per plasmid as well as the required genes for T7 replication (38) with mutant gene 5 DNA polymerase. This allows for a differential mutation rate to exist between the population of DNA encoding the constructs on the *E. coli* chromosome and the putative novel molecule population encoded on the plasmid. Selection is then carried out in glutamine, tryptophan, and pyrimidine limiting media in a chemostat as described in (39) and (40). The selection pressure is then cycled between high and low selection pressure environments in the chemostat (e.g., low levels of glutamine, tryptophan and pyrimidines in the media for high selection pressure and high levels of glutamine, tryptophan and pyrimidines in the media for low selection pressure) as has been described in (41), so as to select for different subspecies of the genes which encode putative novel molecules which in turn aids in obtaining mutants with higher activity for a desired reaction.

Finally evolutionary resetting may be used to further stabilize the selection molecule constructs over time. Periodically during the incubation cells are assayed for their ability to grow in three different media, pyrimidine limiting media containing glutamine and tryptophan (assay for mutation giving rise to aspartate transcarbamoylase function), glutamine limiting media containing pyrimidines and tryptophan (assay for mutation giving rise to glutamine synthetase function), and tryptophan limiting media containing pyrimidines and glutamine (assay for mutation giving rise to tryptophan synthetase function). Using such methods the generation of non-useful mutants may be assayed.

Each time a selection molecule mutant is found to occur, the plasmids are isolated/purified as described in previous examples and then used to transform an aliquot of the original selection molecule encoding *E. coli*. This allows the selection molecule constructs to be evolutionarily reset while maintaining the evolutionary progress of the novel molecule population. The reset population can then be reintroduced into the chemostat. When the novel molecule of the desired specificity is expressed those cells carrying the gene encoding the desired novel molecule are selected in the chemostat and the plasmid carrying the novel molecule may be isolated/purified as described earlier.

Other enzymes or pathways capable of synthesizing or abrogating the need for the compounds synthesized by aspartate transcarbamoylase, glutamine synthetase, and tryptophan synthetase should be made non-functional, preferably by deletion. For example, deletion mutants of glutamine-keto acid transaminase should be used since the enzyme catalyses the synthesis glutamine from 2-ketoglutaramate. Also there should be no mechanism for the synthesis of tryptophan from indole pyruvate or serine. The desired host cell for selection will only grow efficiently when glutamine, tryptophan and pyrimidines are added in the medium. After selection the genes for the endoprotease of interest are isolated/purified, cloned and their expression products characterized.

One skilled in the art will realize that this technique may be used to develop proteases with specificity for recognition sequences other than the one used in the example.

EXAMPLE VI

A Method for Creating a Novel Endopeptidase Using Negative Cellular Selection

Example VI describes a method to create an endopeptidase which cleaves specifically a decapeptide sequence from gp120 with a lower turnover rate than wild type HIV protease. The method employs a recombinant β-galactosidase with a decapeptide recognition sequence. The selection procedure is based on a novel molecule (endoprotease) cleaving a gp120 decapeptide recognition sequence and thus down-modulating the β-galactosidase activity and therefore giving the cells containing the endopeptidase with the desired HIV protease activity a growth disadvantage under selection conditions. The example represents a negative cellular selection procedure.

There are many known single amino acid changes to HIV protease which are capable of rendering the protease enzymatically inactive (5) and (42). One of these inactive missense HIV proteases or a cocktail of them are mutagenized. This example utilizes enzymatically active β-galactosidase containing an HIV protease decapeptide recognition sequence which upon cleavage renders the β-galactosidase molecule inactive (29).

Strains are developed following the protocols from (29), for the production of the *E. coli* MC1061 strain which contain plasmids carrying the β-galactosidase construct and a mutant inactive HIV protease (for example Asp-29→Gly). First, using these methods strains are produced which contain one of the HIV protease inactive mutants described in (5) or (42) or combinations of more than one of them. These cell lines are then grown to allow the isolation/purification of the plasmids, (1) The plasmid DNA is then subjected to mutagenesis as described earlier (1) or by transfecting the plasmids into strains such as *E. coli* strain LE30 mutD which have high rates of mutation (42).

Then the mutagenized plasmids are transfected into *E. coli* strain MC1061, (1), which carry the desired β-galactosidase construct (29). These cells are then selected for negative cellular growth as described in (43).

One skilled in the art will realize that this technique may be used to develop proteases with specificity for recognition sequences other than the one used in the example.

EXAMPLE VII

A Method for Creating a Novel Endopeptidase Using Positive Cellular Selection Example VII describes a method to obtain an endopeptidase which cleaves specifically a decapeptide sequence from gp120 with a lower turnover rate than wild type HIV protease. The method employs a fusion protein of the catalytic subunit of aspartate transcarbamoylase. The selection procedure is based on a novel molecule (endoprotease) cleaving a gp120 decapeptide recognition sequence and up-modulating the aspartate transcarbamoylase activity and therefore giving the cells containing the endopeptidase with the desired HIV protease activity a growth advantage under selection conditions. The example represents a positive cellular selection procedure.

As in the previous example, molecules with HIV protease function are obtained from one or a combination of single amino acid HIV protease mutants which are enzymatically inactive and have been subjected to mutagenesis (as described above). However, in this example a fusion is created of the catalytic subunit of aspartate transcarbamoylase with β-galactosidase attached to its amino terminus through the HIV protease recognition decapeptide from (29) and gene 10 (capsid protein) from bacteriophage T7 attached to its carboxy terminus through the HIV protease recognition decapeptide (1).

The mutagenized population of HIV missense mutants are transfected into modified MC1061 cells which are deletion mutants for the aspartate transcarbamoylase catalytic subunit and contain the aspartate transcarbamoylase fusion properly promoted on the host chromosome using techniques as described in previous examples. Additionally, these host cells are selected for the requirement of functional aspartate transcarbamoylase for efficient growth and are selected for protease deficiency. Selection for the expression of molecules capable of cleaving the fusion and liberating the aspartate transcarbamoylase enzymatic activity is then carried out in a chemostat (39). One skilled in the art will realize that this technique may be used to develop proteases with specificity for recognition sequences other than the one used in the example.

EXAMPLE VIII

A Method for Creating a Novel HIV Protease Using Negative Cellular Selection This example is similar to Example VI. In this example, however, wild type HIV protease is used as a starting point instead of enzymatically inactive missense mutants. Additionally, the HIV decapeptide recognition sequence is changed to one of the following sequences, each of which is to be used in a separate selection run in parallel:

TABLE 1

Relative cleavage of HIV peptide substrates

| Cleavage site* | | | | | | | | | | | | | Code | $(V_{max}/K_m)$rel. † |
|---|---|---|---|---|---|---|---|---|---|---|---|---|---|---|
| | Sequence | | | | | | | | | | | | | |
| 3 | P5 | P4 | P3 | P2 | P1 | | P1' | P2' | P3' | P4' | P5' | | | |
| p6*/PR | V | S | F | N | F | * | P | Q | I | T | L | —$NH_2$ | BI-P-136 | 1.00 |

TABLE 1-continued Relative cleavage of HIV peptide substrates

| Cleavage site* | Sequence | | | | | | | | | | | Code | $(V_{max}/K_m)$rel. † |
|---|---|---|---|---|---|---|---|---|---|---|---|---|---|
| CA⁺/NC | T | A | T | I | M | * | M | Q | R | G | N —NH₂ | BI-P-140 | 0.20 |
| MA/CA | V | S | Q | N | Y | * | P | I | V | Q | N —NH₂ | BI-P-138 | 0.07 |
| CA/CA⁺ | K | A | R | V | L | * | A | E | A | M | S —NH₂ | BI-P-144 | 0.04 |
| PR/RT | C | T | L | N | F | * | P | I | S | P | I —NH₂ | BI-P-127 | 0.03 |
| RT/IN (avian) | Ac-T | F | Q | A | Y | * | P | L | R | E | A —NH₂ | BI-P-102 | <0.005 |

IN, integrase protein.
*Cleavage sites within the HIV gag-pol polyprotein are designated according to the new nomenclature (2), except for the N-terminal product from the pol reading frame (p6*), for which there is no new name. CA⁺ specifies the C-terminally extended capsid protein p25 (24).
† Relative values of $V_{max}/K_m$ were determined by using competition experiments. Each value is an average of at least three determinations and is reproducible to ±20%.

The sequences of BI-P-140 (TATIM) (SEQ ID NO:18); (MQRGN) (SEQ ID NO:19), BI-P-138 (VSQNY) (SEQ ID NO:20); (PIVQN) (SEQ ID NO:21), BI-P-144 (KARVL) (SEQ ID NO:22); (AEAMS) (SEQ ID NO:23), BI-P-127 (CTLNF) (SEQ ID NO:24); (PISPI) (SEQ ID NO:25) and BI-P-102 (TFQAY) (SEQ ID NO:26); (PLREA) (SEQ ID NO:27) (sequence set A) have been shown to be cleaved by HIV protease at various rates, but all at much slower rates than that of the decapeptide of BI-P-136 (VSFNF) (SEQ ID NO:28); (PQITL) (SEQ ID NO:29), if the rate of cleavage is detectable at all (44). Negative cellular selection is then carried out using decapeptide recognition sequences from sequence set A. Four of the five sequences are natural substrates for HIV protease but are processed by the enzyme at a fraction of the rate of the BI-P-136 (VSFNF) (SEQ ID NO:28); (PQITL) (SEQ ID NO:29) substrate decapeptide. Cells are prepared which contain these four sequences-inserted into beta-galactosidase (in an analogous fashion to (29)) and expressed HIV proteases. These cells may be considered 'leaky' auxotrophs to various extents. As such beta-galactosidase will initially be cleaved and therefore inactivated to varying levels in the cells carrying these constructs. The fifth sequence, a recognition sequence from avian sarcoma-leukosis virus, is not specifically cleaved by HIV protease (44) and (45). In addition these strains are selected for the requirement of functional A-galactosidase for efficient growth, and for protease deficiency. HIV protease mutants are obtained with increased turnover rates for the various substrate decapeptides under negative selection conditions with varying concentrations of antibiotic and lactose.

The use of higher concentrations of lactose and antibiotic affords more stringent negative selection pressure by allowing the more leaky auxotrophs to grow using the lactose and then be killed by the penicillin. This selects for HIV protease mutants with higher turnover rates for the constructs of interest. The mutant proteases from the selected cells are then characterized in in vitro assays as described in (29). Those cellular clones with the desired specificity are then grown up and their plasmids encoding the desired function isolated/purified as described above.

One skilled in the art will realize that this technique may be used to develop proteases with specificity for recognition sequences other than the one used in the example.

EXAMPLE IX

A Method for Creating a Novel HIV Protease Using Positive Cellular Selection This example is similar to Example VII. In this example, wild type HIV protease is used as a starting point instead of enzymatically ionactive missense mutants. Additionally, the HIV decapeptide recognition sequence is changed to one of the following sequences (44), each of which is to be used in a separate selection in parallel:

TABLE 1

| Relative cleavage of HIV peptide substrates | | | | | | | | | | | | | | |
|---|---|---|---|---|---|---|---|---|---|---|---|---|---|---|
| Cleavage site* | Sequence | | | | | | | | | | | | Code | $(V_{max}/K_m)$rel. † |
| | P5 | P4 | P3 | P2 | P1 | | P1' | P2' | P3' | P4' | P5' | | | |
| p6*/PR | V | S | F | N | F | * | P | Q | I | T | L | —$NH_2$ | BI-P-136 | 1.00 |
| CA⁺/NC | T | A | T | I | M | * | M | Q | R | G | N | —$NH_2$ | BI-P-140 | 0.20 |
| MA/CA | V | S | Q | N | Y | * | P | I | V | Q | N | —$NH_2$ | BI-P-138 | 0.07 |
| CA/CA⁺ | K | A | R | V | L | * | A | E | A | M | S | —$NH_2$ | BI-P-144 | 0.04 |
| PR/RT | C | T | L | N | F | * | P | I | S | P | I | —$NH_2$ | BI-P-127 | 0.03 |
| RT/IN (avian) | Ac-T | F | Q | A | Y | * | P | L | R | E | A | —$NH_2$ | BI-P-102 | <0.005 |

IN, integrase protein.
*Cleavage sites within the HIV gag-pol polyprotein are designated according to the new nomenclature (2), except for the N-terminal product from the pol reading frame (p6*), for which there is no new name. CA⁺ specifies the C-terminally extended capsid protein p25 (24).
† Relative values of $V_{max}/K_m$ were determined by using competition experiments. Each value is an average of at least three determinations and is reproducible to ±20%.

The sequences of BI-P-140 (TATIM) (SEQ ID NO:18); (MQRGN) (SEQ ID NO:19), BI-P-138 (VSQNY) (SEQ ID NO:20); (PIVQN) (SEQ ID NO:21), BI-P-144 (KARVL) (SEQ ID NO:22); (AEAMS) (SEQ ID NO:23), BI-P-127 (CTLNF) (SEQ ID NO:24); (PISPI) (SEQ ID NO:25) and BI-P-102 (TFQAY) (SEQ ID NO:26); (PLREA) (SEQ ID NO:27) (sequence set A) have been shown to be cleaved by HIV protease at various rates, but all at much slower rates than that of the decapeptide of BI-P-136 (VSFNF) (SEQ ID NO:28); (PQITL) (SEQ ID NO:29), if the rate of cleavage is detectable at all (44). Positive cellular selection is then carried out in a chemostat (described previously) under various dilution rates and selection pressures to select cells that express proteases that are capable of liberating aspartate transcarbamoylase enzymatic activity through cleavage of the fusion construct at desired turnover rates. The mutant HIV proteases in the selected cellular clones may then be further characterized using the in vitro assays as described in (29). Those cellular clones with the desired specificity are then grown up and their plasmids encoding the desired function isolated/purified as described previously.

One skilled in the art will realize that this technique may be used to develop proteases with specificity for recognition sequences other than the one used in the example.

EXAMPLE X

Cell-Free Selection

This example illustrates how various steps are carried out in controlled cell-free environments.

The endopeptidase used is a missense mutant of HIV protease such as Asn-25 (5) and (42). The genes for these enzymes are encoded on plasmids and mutagenized using any of the methods described in earlier examples including chemical mutagenesis, site directed mutagenesis, and low fidelity replication (e.g., growing in MutD strain).

The mutagenized population of enzymes is produced in $E.$ $coli$ as before, and then isolated/purified (using techniques such as are described in (1)). The plasmids containing the endopeptidase population are isolated/purified (1). Similar protocols are used to express a fusion protein of actin linked at its amino terminus to β-galactosidase with a HIV protease recognition sequence (29) and to gene 10 of T7 at its carboxy terminus through the same HIV protease recognition sequence. The expressed fusion construct is isolated/purified as described before. Alternatively, the putative novel molecule and actin fusion genes may be amplified and expressed using expression PCR as described in (48). This would eliminate the use of live cells in any aspect of the procedure.

The expressed putative novel molecule proteins are incubated with the isolated/purified actin fusion proteins allowing novel molecule proteases with the desired function to cleave the recognition sequence. The resulting mixture from the putative novel molecule and actin fusion incubation are then incubated together in the presence of isolated/purified Dnase I. DNase is known to be inhibited by the 1:1 complexing with actin monomers (46, 47). The actin monomer is sterically free to bind to the DNase I enzyme after proper cleavage of the HIV protease recognition sequence.

The isolated/purified plasmid (or PCR DNA) encoding the putative novel molecule population is then added to the reaction mixture and incubated. The resulting DNA is isolated/purified from the incubation mixture using methods described in (1). The DNA is then characterized using gel electrophoresis.

Upon identification of a DNA band corresponding to an undigested plasmid encoding a putative novel molecule, the DNA from this band is isolated/purified (1) and equally divided into 100 samples. Each sample is amplified and the putative novel molecules expressed and their function assayed as before to determine which sample encoded novel molecule capable of inhibiting the DNase I. Further partitioning of the samples encoding the enzymatic activity is carried out until the desired clone is obtained and optionally amplified. At this point the novel molecules are characterized for various attributes such as turnover rate.

If the novel molecules' characteristics are as desired no further development is required. If they are not, the novel molecules are further evolutionarily progressed. Using the DNA encoding these novel molecules the process is repeated by re-mutagenizing the novel molecules' gene population, amplifying, and then assaying again for the desired function in the expressed proteins. In this way the DNA encoding the novel molecule population can undergo an evolutionary progression so as to obtain a novel molecule with the preferred characteristics.

EXAMPLE XI

Directed Evolution of a Novel Protease Specific for an Epitope of Influenza Haemagglutinin (HA) Encoded in an M13 Vector Using an Aspartate-semialdehyde Dehydrogenase (ASD) Based Selection Molecule in $E.$ $coli$ in a Batch Process Conducted in a Chemostat Aspartate-semialdehyde dehydrogenase (ASD) catalyzes the production of aspartate 4-semialdehyde from aspartyl 4-phosphate in $E.$ $coli$. The reaction is NADPH dependent and liberates a phosphate group. The production of aspartate 4-semialdehyde is a branch point from which the precursors of the 4 amino acids methionine, threonine, isoleucine, and lysine are generated. Thus, if ASD is non-functional in the cell and the cells are selected such that there are no alternate pathways for the production of aspartate 4-semialdehyde or any of the other important metabolites downstream of aspartate 4-semialdehyde, the cell will not be able to grow without addition of the four amino acids in the media. In addition the cells are selected to be protease deficient.

An ASD based selection construct is produced by creating a fusion protein. β-galactosidase is encoded upstream of the ASD sequence and asparagine synthetase is encoded downstream. β-galactosidase and asparagine synthetase are linked to ASD through a decapeptide recognition sequence from influenza HA site B (32), Thr-Asp-Gln-Glu-Gln-Thr-Ser-Leu-Tyr-Val (SEQ ID NO:30). The fusion protein is encoded on the $E.$ $coli$ chromosome under the control of the strongest promoter which is shown to confer acceptable background ASD activity. With the maximal number of fusion proteins available, novel molecules with low turnover but the correct proteolytic specificity have a selective advantage.

This method permits the growth within a chemostat of cells and replicators wherein there is a separation of the coding sequences for selection molecules and putative novel molecules allowing differential mutation rates. The selection relies on the dual selection of the cells and the replicators in a symbiotic relationship.

The novel molecule evolutionary starting point is a protease which recognizes a specific sequence and which is not deleterious to the system, e.g., collagenase from Achromobacter iophagus and clostridium histolyticium which predominantly cleave at X-gly and pro-X-gly-pro, is encoded for in the genome of a phage such as M13. Large numbers of M13 phage encoding the novel molecule are subjected to strong mutagens such as ethyl methane sulfonate, nitrosoguanidine, and irradiation. Mutagenation gives rise to a heterogeneous population which is then incubated in a chemostat with $E.$ $coil$ encoding the selection construct in minimal media without the four amino acids. Random mutagenesis confers an evolutionary head start on the novel molecule population relative to the selection constructs. In addition, the M13 genome is replicated at a higher rate than the E. coli chromosome further increasing the number of mutations in the M13 genome relative to the E. coli chromosome. Those M13 molecules with the greatest activity are obtained based on their selective growth advantage. The genes which encode the most promising novel molecules are isolated/purified from the population and these can be mutagenized again and incubated with an evolutionary reset population of E. coli cells encoded for a fusion protein selection construct in a repeatable batch-type process. This allows for the maintenance of the best novel molecules while keeping the fusion protein stable by refreshing its population many times.

EXAMPLE XII

Directed Evolution Of A Novel Protease Specific for A Recognition Sequence from HIV gp120 Encoded In An M13 Vector Using Selection Constructs Containing Enzymes Important In The Synthesis of Chorismate In E. coli* Using Differential Mutation Rate, Redundancy and a Heterogeneous Initial Ponulation Chorismate is a branch point in the biosynthesis of phenylalanine, tyrosine and tryptophan. Its production is catalyzed by the enzymatic action of chorismate synthase on 3-enolpyruvyl-shikimate 5-phosphate. Production of chorismate follows a linear unbranched pathway from 3-deoxy-7-phospho-D-arabinoheptulosonate. The pathway including chorismate and 3-deoxy-7-phospho-D-arabinoheptulosonate contains seven members and is catalyzed by six different enzymes of which one is chorismate synthase.

Each of the six enzymes is used in a different protein fusion selection construct encoded on the *E. coli* chromosome of a strain selected to require chorismate for efficient growth and selected to be protease deficient. The coding sequence for each enzyme, flanked on both sides with the proteolytic recognition sequence of interest, amino acids 271–295 of variable region 3 from HIV gp120 (N-N-T-R-K-S-I-R-I-Q-R-G-P-G-R-A-F-V-T-I-G-K-I-G-N) (SEQ ID NO:31), is sandwiched between appropriate bulky groups such as β-galactosidase, one of the three phospho-2-3-deoxyheptonate aldolases and proteins from bacteriophage, as described in other examples. The fusion proteins are encoded on the *E. coli* chromosome under the control of the strongest promoter which is shown to confer acceptable background activity. It is preferred to use modulation moieties each of which is non-homologous and which have no homology to genes within the *E. coli* chromosome. Modulation molecules are chosen which effectively down-modulate the six enzymes including chorismate synthase. These redundant selection molecules channel the development of a protease specific for the recognition sequence from gp120 which is the only common sequence to all of the fusions.

The *E. coli* cell line produced encodes all six of the fusion based selection constructs thereby creating a redundant system. In this system, the biosynthesis of chorismate is blocked even if five of the six protein fusions undergo non-useful deletions. In addition, the redundant system works even if down-modulation of the enzymatic functions in the several proteins is not complete. Since each of the enzymes catalyzes a reaction in the same pathway, the down-modulation of each within their fusions has a cumulative effect on the production of chorismate.

The putative novel molecule population is encoded in an M13 phage. The evolutionary starting points for the novel molecule include HIV protease subtilisin BPN, polio 3C protease and collagenases from Achromobacter iophagus and clostridium histolyticium. A large population of such phage are mutagenized so as to confer an evolutionary head start to the putative novel molecule population.

Differential mutation rates for the selection constructs and the novel molecules are created by using different origins of replication and their corresponding replication machinery. The selection constructs are replicated solely by the natural *E. coli* holoenzyme complex while the novel molecules may be replicated by the T7 DNA replication machinery.

To create an M13 phage in which replication of the putative novel molecule population is directed by T7 machinery, a dual replication mechanism is introduced. M13 is encoded on a circular single stranded DNA genome. T7 is a linear double stranded DNA phage. During its replication, however, M13 is produced in a double stranded form. The normal M13 origin is kept intact so as to get the phage to its double stranded form, and then a T7 replication system can be targeted to replicate genes on the M13 genome.

To do this T7 genes required for replication including mutant low fidelity T7 DNA polymerase are expressed from either the M13 genome, the bacterial chromosome, or a plasmid. These genes include a modified T7 DNA polymerase (gene 5) of low fidelity, the T7 RNA polymerase, and the T7 gyrase (gene 4) (38). The T7 replication machinery is under the control of a strong promoter so that a high copy number is achieved. The M13 genome contains a number of T7 origins of replication so that once the M13 is double stranded, the large copy number of T7 replication machinery successfully competes with the *E. coli* holoenzyme (which is present in very low copy numbers within a cell) for the replication of the M13 genome. The putative novel molecule or molecules are located near the T7 origin of replication so as to increase the likelihood that if both a bacterial holoenzyme and a T7 DNA polymerase are actively replicating the same M13 genome, the modified T7 polymerase with low fidelity will replicate the novel molecule.

The differential mutation rate is also enhanced by increasing the copy number of putative novel molecule sequences on the M13 genome. These sequences may or may not be complete. For example, multiple copies of the complete putative novel molecule may lead to beneficial homologous recombinations. In addition, small stretches of DNA, especially those encoding important portions of the novel molecule such as the catalytic site, may be randomly incorporated into the M13 genome so that increased numbers of small recombinations around important sites will occur. These small sequences will also be likely to bring in random flanking sequences (since they are randomly distributed in the genome) in some fraction of the recombinations.

The *E. coli* containing the redundant system and the heterogeneous starting population of M13s described above encoding the novel molecules is grown in a chemostat. The selection pressure is modulated, kept constant, or regularly cycled by adjusting the chemostat environment, in particular the concentration of the amino acids phenylalanine, tyrosine, and tryptophan and the flow rate. Samples of the M13 bacteriophage are taken regularly and assayed for the ability to produce novel molecules with the desired proteolytic activity.

EXAMPLE XIII

Directed Evolution of a Novel Kinase for $NR_I$ from *E. coli*

Example XIII describes a method for the directed evolution of a kinase capable of phosphorylating and thereby modulating the function of NR, from *E. coli* (2). Evolutionary starting points are encoded on a plasmid replicated by low-fidelity T7 replication machinery. The phosphorylated $NR_I$ allows for cell growth within the selection system, and therefore this is an example of positive cellular selection.

An *E. coli* strain, selected for the requirement of glutamine synthetase for efficient growth is constructed with the following modifications. In this strain the glnA-glnL-glnG operon is substantially altered. The promoters recognized by $\sigma^{70}$ are deleted. The glnL and glnG genes are deleted and replaced by the gene for DNaA. All other copies of the DNaA gene are deleted. The glnG gene, which encodes NRI, is placed under the control of a promoter recognized by a factor such as $\sigma^{70}$ and not $\sigma^{54}$. The required genes for T7 replication (38) with a T7 DNA polymerase of low fidelity are inserted and properly promoted and expressed. A plasmid is constructed and introduced into the strain which is replicated by the low-fidelity T7 replication machinery. Thus the plasmid, based on pUC118, is a deletant for origins of replication functionally recognized by cellular replication machinery and instead contains the major origin of T7 replication which contains promoters ø1.1A and ø1.1B. A heterogeneous set of evolutionary starting points based on bacterial kinases, CheA, SpoIIJ, FrzE, DctB, and AprZ are mutated and inserted into the plasmid so as to allow their proper expression.

The cells are then incubated in glutamine and nitrogen limiting media. Cells capable of growth are selected. In this example selection occurs through a cascade. A properly phosphorylated NRI is capable of acting as an enhancer to the promoter glnApZ recognized by $\sigma^{54}$ by binding an upstream DNA sequence. The enhanced glnApZ promoter then allows for the high level expression of glnA (glutamine synthetase) and DNaA. These proteins then in turn activate cascades which allow for cellular growth and replication.

After selection the genes for the kinase of interest are isolated/purified, cloned and their expression products characterized.

One skilled in the art will realize that this technique may be used to develop kinases with specificity for recognition sequences other than the one used in the example.

CITATIONS

1. Sambrook et al., *Molecular Cloning a Laboratory Manual* 2ed., (Cold Spring Harbor Laboratory), (1989).
2. Neidhardt et al., *Physiology of the Bacterial Cell* (Sinauer Associates Inc. Publishers), (1990).
3. Reich, *Proteases and Biological Control*, Vol. 2, pp. 1–64 (1975).
4. Hyde et al., *J. of Biol. Chem.*, Vol. 263, No. 33, pp. 17857–17871 (1988).
5. Kohl et al., *Proc. Natl. Acad. Sci. USA*, Vol. 85, pp. 4686–4690 (1988).
6. Fritsch, *Enzyme Structure and Mechanism*, 2ed., (Freeman & Co. Publishers, (1984).
7. Kantrowitz et al., *TIBS* 15, pp. 55–59 (1990).
8. Lehninger, *Principles of Biochemistry*, (Worth Publishers) p. 504 (1982).
9. Harlow et al., *Antibodies, a Laboratory Manual*, (Cold Spring Harbor Laboratory) pp. 139–281, (1988).
10. Skerra et al., *Science*, Vol. 240, pp. 1041–1043 (1988).
11. Pluckthun et al., *Methods in Enzymology*, Vol. 178, pp. 497–515 (1989).
12. Better et al., *Science*, Vol. 240, pp. 1041–1043 (1988).
13. W. Paul, *Fundamental Immunology* 2ed., (Raven Press) (1989).
14. Schlessinger et al., *Proc. Nat. Acad. Sci. USA*, Vol. 72, No. 7, pp. 2775–2779 (1975).
15. Jaton et al., *J. of Immunology*, Vol. 116, No. 5, pp. 1363–1366 (1976).
16. Givol et al., Conformational changes in the Fab and Fc of the antibody as a consequence of antigen binding. *Proceedings of the Second International Congress of Immunology*, Vol. 1, Edited by Brent and Holbrow. North Holland Publishers, Amsterdam, p. 39 (1974).
17. Jaton et al., Conformational changes induced in a homogeneous anti-type III pneumococcal antibody by oligosaccharides of increasing size, *Biochemistry*, 14:5312 (1975).
18. Rini et al., *Science*, Vol. 255, pp. 959–965 (1992).
19. Cantor et al., *Biophysical Chemistry Part I: The Conformation of Biological Molecules*, pp. 127–145 (1990).
20. Buell et al., Optimizing the expression in E. coli of a synthetic gene encoding somatomedin-C (IGF-I). *Nucleic Acids Res.* 13:1923 (1985).
21. Dunn et al., *J. Mol. Biol.*, Vol. 166, pp. 477–535 (1983).
22. Studier, F. W., *Virology*, 39, 562–568 (1969).
23. Studier, F. W., *Virology*, 95, 70–84 (1979).
24. Silhavy et al., *Microbiol. Rev.*, Vol. 49, pp. 400–405 (1985).
25. Kutter et al., *Bacteriophage* T4, Structure, organization, and Manipulation of the Genome, pp. 277–290 (1983).
26. Leonard et al., *J. of Biol. Chem.*, Vol. 265, No. 18, pp. 14017–10382 (1990).
27. Starcich, et al., *Cell*, Vol. 45, pp. 637–648 (1986).
28. Masker et al., *J. of Virology*, Vol. 27, No. 1, pp. 149–163 (1978).
29. Baum et al., *Proc. Natl. Acad. Sci. USA*, Vol. 87, pp. 10023–10027 (1990).
30. Carter et al., *Science*, Vol. 237, pp. 394–398 (1987).
31. Husimi, *Advances in Biophysics*, 25:1–43 (1989).
32. Wiley et al., *Nature*, Vol. 289, No. 29, pp. 373–378 (1981).
33. Nagai et al., *Nature*, Vol. 309, No. 28, pp. 810–812 (1984).
34. Jia et al., *Gene*, 60, pp. 197–204 (1987).
35. Lehninger, *Principles of Biochemistry*, (Worth Publishers) p. 504 (1982).
36. Harlow et al., *Antibodies, a Laboratory Manual*, (Cold Spring Harbor Laboratory) pp. 139–281 (1988).
37. Rabkin et al., *J. Mol. Biol.*, Vol. 204, pp. 903–916 (1988).
38. Kornberg et al., Bacterial DNA Viruses, Chapter 17, from *DNA Replication*, pp. 586–597 (Freeman & Co. Publishers), (1992).
39. Stafford, K., Continuous Fermentation, Chapter 11, from *Manual of Industrial Microbiology*, Edited by Demain and Solomon, pp. 137–151 (1986).
40. Dykhuizen et al., *Microbiology Reviews*, Vol. 47, No. 2, pp. 150–168 (1983).
41. Tsen, S., *Biochem. and Biophys. Res. Comm.*, Vol. 166, No. 3, pp. 1245–1250 (1990).
42. Baum et al., *Proc. Natl. Acad. Sci. USA*, Vol. 87, pp. 5573–5577 (1990).
43. Queener et al., Screening and Selection for Strain Improvement, Chapter 12, from *Manual of Industrial Microbiology*, Edited by Demain & Solomon, pp. 155–169 (1986).
44. Krausslich et al., *Proc. Natl. Acad. Sci. USA*, Vol. 86, pp. 807–811 (1989).
45. Kotler et al., *Proc. Natl . Acad. Sci . USA*, Vol. 85, pp. 4185–4189 (1988).
46. Laskowski, Deoxyribonuclease I, from *The Enzymes*, Third Edition, Vol. 4, pp. 289–311, edited by Boyer (1971).
47. Moore, Pancreatic DNase, from *The Enzymes*, Third Edition, Vol. 14, pp. 281–296, edited by Boyer (1981).
48. Kain, *Biotechnicues*, Vol. 10, No. 3, pp. 366–73 (1991)

I claim:

1. A selected population of host cells and/or replicators which express a molecule that undergoes a desired interaction with a recognition sequence, said population of host cells being produced by a method comprising the steps of:
   (a) expressing multiple copies of a putative molecule or a multiplicity of different putative molecules in a population of host cells containing a growth factor, a modulation moiety and said recognition sequence; and
   (b) subjecting said population of host cells to mutagenizing conditions and imposing selection conditions to select for those host cells and/or replicators having modified growth as a result of an interaction between said molecule that undergoes a desired interaction with said recognition sequence, said modulation moiety and said recognition sequence, such that at least one replicator and/or cell in said population undergoes at least one cycle of division and/or replication under said conditions;
   wherein said putative molecule or multiplicity of different putative molecules evolve into said molecule that undergoes a desired interaction with said recognition sequence.

2. A population of host cells as claimed in claim 1 wherein said growth factor is selected from the group consisting of a cell growth factor and a replicator growth factor.

3. A population of host cells as claimed in claim 1 wherein said growth factor, recognition sequence and modulation moiety are contained in a single polypeptide.

4. A population of host cells as claimed in claim 1 wherein said mutagenizing conditions and selection conditions are imposed on the host cell population sequentially.

5. A population of host cells as claimed in claim 1 wherein said recognition sequence is said modulation moiety.

6. A population of host cells as claimed in claim 1 wherein said putative molecules are homogeneous and/or said putative molecules are lacking the activity of said molecule that undergoes a desired interaction with said recognition sequence.

7. A selected population of host cells and/or replicators which express a molecule that undergoes a desired interaction with a recognition sequence, said population of host cells being produced by a method comprising the steps of:
(a) expressing multiple copies of a putative molecule or a multiplicity of different putative molecules in a population of host cells containing a growth factor, a modulation moiety and said recognition sequence, said putative molecule or multiplicity of different putative molecules having a substrate specificity and/or catalytic activity less than that of said molecule that undergoes a desired interaction with said recognition sequence; and
(b) subjecting said population of host cells to mutagenizing conditions and imposing selection conditions to select for those host cells and/or replicators having modified growth as a result of an interaction between said molecule that undergoes a desired interaction with said recognition sequence, said modulation moiety and said recognition sequence, such that at least one replicator and/or cell in said population undergoes at least one cycle of division and/or replication under said conditions;
wherein said putative molecule or multiplicity of different putative molecules evolve into said molecule that undergoes a desired interaction with said recognition sequence.

8. A population of host cells as claimed in claim 7 wherein said growth factor is selected from the group consisting of a cell growth factor and a replicator growth factor.

9. A population of host cells as claimed in claim 7 wherein said growth factor, recognition sequence and modulation moiety are contained in a single polypeptide.

10. A population of host cells as claimed in claim 7 wherein said mutagenizing conditions and selection conditions are imposed on the host cell population sequentially.

11. A population of host cells as claimed in claim 7 wherein said recognition sequence is said modulation moiety.

12. A population of host cells as claimed in claim 7 wherein said putative molecules are homogeneous and/or said putative molecules are lacking the activity of said molecule that undergoes a desired interaction with said recognition sequence.

13. A selected population of host cells and/or replicators comprising a nucleic acid which encodes a putative molecule has evolved into a molecule that undergoes a desired interaction with a recognition sequence, said population of host cells being produced by a method comprising the steps of:
(a) introducing multiple copies of a nucleic acid which encodes a putative molecule or a multiplicity of different putative molecules in a population of host cells containing a growth factor, a modulation moiety and said recognition sequence; and
(b) subjecting said population of host cells to mutagenizing conditions and imposing selection conditions to select for those host cells and/or replicators having modified growth as a result of an interaction between said molecule that undergoes a desired interaction with said recognition sequence, said at least one replicator and/or cell in said population undergoes at least one cycle of division and/or replication under said conditions;
wherein said putative molecule or multiplicity of different putative molecules evolve into said molecule that undergoes a desired interaction with said recognition sequence.

14. A population of host cells as claimed in claim 13 wherein said growth factor is selected from the group consisting of a cell growth factor and a replicator growth factor.

15. A population of host cells as claimed in claim 13 wherein said growth factor, recognition sequence and modulation moiety are contained in a single polypeptide.

16. A population of host cells as claimed in claim 13 wherein said mutagenizing conditions and selection conditions are imposed on the host cell population sequentially.

17. A population of host cells as claimed in claim 13 wherein said recognition sequence is said modulation moiety.

18. A population of host cells as claimed in claim 13 wherein said putative molecule or multiplicity of different putative molecules have a substrate specificity and/or catalytic activity less than that of said molecule that undergoes a desired interaction with said recognition sequence.

19. A population of host cells as claimed in claim 13 wherein said putative molecules are homogeneous and/or said putative molecules are lacking the activity of said molecule that undergoes a desired interaction with said recognition sequence.

20. A population of host cells as claimed in claim 13 wherein said putative molecule or multiplicity of different putative molecules have a substrate specificity and/or catalytic activity greater than that of said molecule that undergoes a desired interaction with said recognition sequence.

21. A selected population of host cells and/or replicators which express a catalyst that undergoes a desired interaction with a recognition sequence, said population of host cells being produced by a method comprising the steps of:
(a) expressing multiple copies of a putative molecule or a multiplicity of different putative molecules in a population of host cells containing a growth factor, a modulation moiety and said recognition sequence, and
(b) subjecting said population of host cells to mutagenizing conditions to select for those host cells and/or replicators having modified growth as a result of an interaction between said catalyst, said modulation moiety and said recognition sequence, such that at least one replicator and/or cell in said population undergoes at least one cycle of division and/or replication under said conditions,
wherein said putative molecule or multiplicity of different putative molecules evolve into said catalyst and said evolved catalyst undergoes a desired interaction with said recognition sequence.

22. A population of host cells as claimed in claim 21 wherein said growth factor is selected from the group consisting of a cell growth factor and a replicator growth factor.

23. A population of host cells as claimed in claim 21 wherein said growth factor, recognition sequence and modulation moiety are contained in a single polypeptide.

24. A population of host cells as claimed in claim 21 wherein said mutagenizing conditions and selection conditions are imposed on the host cell population sequentially.

25. A population of host cells as claimed in claim 21 wherein said recognition sequence is said modulation moiety.

26. A population of host cells as claimed in claim 21 wherein said putative molecule or multiplicity of different putative molecules have a substrate specificity and/or catalytic activity less than that of said catalyst.

27. A population of host cells as claimed in claim 21 wherein said putative molecule or multiplicity of different putative molecules are homogeneous and/or said putative molecule are lacking the activity of said catalyst.

28. A population of host cells as claimed in claim 21 wherein said putative molecule or multiplicity of different putative molecules have a substrate specificity and/or catalytic activity greater than that of said catalyst.

29. A selected population of host cells which express a protease that undergoes a desired interaction with a recognition sequence, said population of host cells being produced by a method comprising the steps of:

(a) expressing multiple copies of a putative molecule or a multiplicity of different putative molecules in a population of host cells containing a growth factor, a modulation moiety and said recognition sequence; and (b) subjecting said population of host cells to mutagenizing conditions and imposing selection conditions to select for those host cells and/or replicators having modified growth as a result of an interaction between said protease, said modulation moiety and said recognition sequence, such that at least one replicator and/or cell in said population undergoes at least one cycle of division and/or replication under said conditions;

wherein said putative molecule or multiplicity of different putative molecules evolve into said protease and said evolved protease undergoes a desired interaction with said recognition sequence.

30. A population of host cells as claimed in claim 29 wherein said growth factor is selected from the group consisting of a cell growth factor and a replicator growth factor.

31. A population of host cells as claimed in claim 29 wherein said growth factor, recognition sequence and modulation moiety are contained in a single polypeptide.

32. A population of host cells as claimed in claim 29 wherein said mutagenizing conditions and selection conditions are imposed on the host cell population sequentially.

33. A population of host cells as claimed in claim 29 wherein said recognition sequence is said modulation moiety.

34. A population of host cells as claimed in claim 29 wherein said putative molecule or multiplicity of different putative molecules have a substrate specificity and/or catalytic activity less than that of said protease.

35. A population of host cells as claimed in claim 29 wherein said putative molecules are homogeneous and/or said putative molecules are lacking the activity of said protease.

36. A population of host cells as claimed in claim 29 wherein said putative molecule or multiplicity of different putative molecules have a substrate specificity and/or catalytic activity greater than that of said protease.

37. A selected population of host cells and/or replicators which express a molecule that undergoes a desired interaction with a recognition sequence, said population of host cells being produced by a method comprising the steps of:

(a) expressing multiple copies of a putative molecule or a multiplicity of different putative molecules in a population of host cells containing a growth factor, a modulation moiety and said recognition sequence, said putative molecule or multiplicity of different putative molecules having a substrate specificity and/or catalytic activity greater than that of said molecule that undergoes a desired interaction with said recognition sequence; and (b) subjecting said population of host cells to mutagenizing conditions and imposing selection conditions to select for those host cells and/or replicators having modified growth as a result of an interaction between said molecule that undergoes a desired interaction with said recognition sequence, said modulation moiety and said recognition sequence, such that at least one replicator and/or cell in said population undergoes at least one cycle of division and/or replication under said conditions;

wherein said putative molecule or multiplicity of different putative molecules evolve into said molecule that undergoes a desired interaction with said recognition sequence.

38. A population of host cells as claimed in claim 37 wherein said growth factor is selected from the group consisting of a cell growth factor and a replicator growth factor.

39. A population of host cells as claimed in claim 37 wherein said growth factor, recognition sequence and modulation moiety are contained in a single polypeptide.

40. A population of host cells as claimed in claim 37 wherein said mutagenizing conditions and selection conditions are imposed on the host cell population sequentially.

41. A population of host cells as claimed in claim 37 wherein said recognition sequence is said modulation moiety.

42. A population of host cells as claimed in claim 37 wherein said putative molecules are homogeneous and/or said putative molecules are lacking the activity of said molecule that undergoes a desired interaction with said recognition sequence.

43. A selected population of host cells and/or replicators which express a molecule that undergoes a desired interaction with a recognition sequence, said population of host cells being produced by a method comprising the steps of:

(a) expressing multiple copies of a putative molecule or a multiplicity of different putative molecules in a population of host cells containing a growth factor, a modulation moiety and said recognition sequence;

(b) subjecting said population of host cells to mutagenizing conditions which preferentially mutagenize a nucleic acid encoding said putative molecule or multiplicity of different putative molecules within said host cells; and (c) imposing selection conditions to select for those host cells and/or replicators having modified growth as a result of an interaction between said molecule that undergoes a desired interaction with said recognition sequence, said modulation moiety and said recognition sequence, such that at least one replicator and/or cell in said population undergoes at least one cycle of division and/or replication under said conditions;

wherein said putative molecule or multiplicity of different putative molecules evolve into said molecule that undergoes a desired interaction with said recognition sequence.

44. A population of host cells as claimed in claim 43 wherein said growth factor is selected from the group consisting of a cell growth factor and a replicator growth factor.

45. A population of host cells as claimed in claim 43 wherein said growth factor, recognition sequence and modulation moiety are contained in a single polypeptide.

46. A population of host cells as claimed in claim 43 wherein said mutagenizing conditions and selection conditions are imposed on the host cell population sequentially.

47. A population of host cells as claimed in claim 43 wherein said recognition sequence is said modulation moiety.

48. A population of host cells as claimed in claim 43 wherein said putative molecules are homogeneous and/or said putative molecules are lacking the activity of said molecule that undergoes a desired interaction with said recognition sequence.

49. A selected population of host cells and/or replicators which express a molecule that undergoes a desired interaction with a recognition sequence, said population of host cells being produced by a method comprising the steps of:

(a) expressing multiple copies of a putative molecule or a multiplicity of different putative molecules in a population of host cells containing a growth factor, a modulation moiety and said recognition sequence, said putative molecule or multiplicity of different putative molecules having a substrate specificity and/or catalytic activity less than that of said molecule that undergoes a desired interaction with said recognition sequence;

(b) subjecting said population of host cells to mutagenizing conditions which preferentially mutagenize a nucleic acid encoding said putative molecule or multiplicity of different putative molecules within said host cells; and (c) imposing selection conditions to select for those host cells and/or replicators having modified growth as a result of an interaction between said molecule that undergoes a desired interaction with said recognition sequence, said modulation moiety and said recognition sequence, such that at least one replicator and/or cell in said population undergoes at least one cycle of division and/or replication under said conditions;

wherein said putative molecule or multiplicity of different putative molecules evolve into said molecule that undergoes a desired interaction with said recognition sequence.

50. A population of host cells as claimed in claim 49 wherein said growth factor is selected from the group consisting of a cell growth factor and a replicator growth factor.

51. A population of host cells as claimed in claim 49 wherein said growth factor, recognition sequence and modulation moiety are contained in a single polypeptide.

52. A population of host cells as claimed in claim 49 wherein said mutagenizing conditions and selection conditions are imposed on the host cell population sequentially.

53. A population of host cells as claimed in claim 49 wherein said recognition sequence is said modulation moiety.

54. A population of host cells as claimed in claim 49 wherein said putative molecules are homogeneous and/or said putative molecules are lacking the activity of said molecule that undergoes a desired interaction with said recognition sequence.

55. A selected population of host cells and/or replicators comprising a nucleic acid which encodes a putative molecule has evolved into a molecule that undergoes a desired interaction with a recognition sequence, said population of host cells being produced by a method comprising the steps of:

(a) introducing multiple copies of a nucleic acid which encodes a putative molecule or a multiplicity of different putative molecules in a population of host cells containing a growth factor, a modulation moiety and said recognition sequence;

(b) subjecting said population of host cells to mutagenizing conditions which preferentially mutagenize a nucleic acid encoding said putative molecule or multiplicity of different putative molecules within said host cells; and (c) imposing selection conditions to select for those host cells and/or replicators having modified growth as a result of an interaction between said molecule that undergoes a desired interaction with said recognition sequence, said modulation moiety and said recognition sequence, such that at least one replicator and/or cell in said population undergoes at least one cycle of division and/or replication under said conditions;

wherein said putative molecule or multiplicity of different putative molecules evolve into said molecule that undergoes a desired interaction with said recognition sequence.

56. A population of host cells as claimed in claim 55 wherein said growth factor is selected from the group consisting of a cell growth factor and a replicator growth factor.

57. A population of host cells as claimed in claim 55 wherein said growth factor, recognition sequence and modulation moiety are contained in a single polypeptide.

58. A population of host cells as claimed in claim 55 wherein said mutagenizing conditions and selection conditions are imposed on the host cell population sequentially.

59. A population of host cells as claimed in claim 55 wherein said recognition sequence is said modulation moiety.

60. A population of host cells as claimed in claim 55 wherein said putative molecule or multiplicity of different putative molecules have a substrate specificity and/or catalytic activity less than that of said molecule that undergoes a desired interaction with said recognition sequence.

61. A population of host cells as claimed in claim 55 wherein said putative molecule or multiplicity of different putative molecules have a substrate specificity and/or catalytic activity greater than that of said molecule that undergoes a desired interaction with said recognition sequence.

62. A population of host cells as claimed in claim 55 wherein said putative molecules are homogeneous and/or said putative molecules are lacking the activity of said molecule that undergoes a desired interaction with said recognition sequence.

63. A selected population of host cells and/or replicators which express a catalyst that undergoes a desired interaction with a recognition sequence, said population of host cells being produced by a method comprising the steps of:

(a) expressing multiple copies of a putative molecule or a multiplicity of different putative molecules in a population of host cells containing a growth factor, a modulation moiety and said recognition sequence;

(b) subjecting said population of host cells to mutagenizing conditions which preferentially mutagenize a nucleic acid encoding said putative molecule or multiplicity of different putative molecules within said host cells; and (c) imposing selection conditions to select for those host cells and/or replicators having modified growth as a result of an interaction between said catalyst, said modulation moiety and said recognition sequence, such that at least one replicator and/or cell in said population undergoes at least one cycle of division and/or replication under said conditions;

wherein said putative molecule or multiplicity of different putative molecules evolve into said catalyst.

64. A population of host cells as claimed in claim 63 wherein said growth factor is selected from the group consisting of a cell growth factor and a replicator growth factor.

65. A population of host cells as claimed in claim 63 wherein said growth factor, recognition sequence and modulation moiety are contained in a single polypeptide.

66. A population of host cells as claimed in claim 63 wherein said mutagenizing conditions and selection conditions are imposed on the host cell population sequentially.

67. A population of host cells as claimed in claim 63 wherein said recognition sequence is said modulation moiety.

68. A population of host cells as claimed in claim 63 wherein said putative molecule or multiplicity of different putative molecules have a substrate specificity and/or catalytic activity less than that of said catalyst.

69. A population of host cells as claimed in claim 63 wherein said putative molecules or multiplicity of different putative molecules have a substrate specificity and/or catalytic activity greater than that of said catalyst.

70. A population of host cells as claimed in claim 63 wherein said putative molecules are homogeneous and/or said putative molecules are lacking the activity of said catalyst.

71. A selected population of host cells which express a protease that undergoes a desired interaction with a recognition sequence, said population of host cells being produced by a method comprising the steps of:
 (a) expressing multiple copies of a putative molecule or a multiplicity of different putative molecules in a population of host cells containing a growth factor, a modulation moiety and said recognition sequence;
 (b) subjecting said population of host cells to mutagenizing conditions which preferentially mutagenize a nucleic acid encoding said putative molecule or multiplicity of different putative molecules within said host cells; and
 (c) imposing selection conditions to select for those host cells and/or replicators having modified growth as a result of an interaction between said protease, said modulation moiety and said recognition sequence, such that at least one replicator and/or cell in said population undergoes at least one cycle of division and/or replication under said conditions;
 wherein said putative molecule or multiplicity of different putative molecules evolve into said protease and said protease undergoes a desired interaction with said recognition sequence.

72. A population of host cells as claimed in claim 71 wherein said growth factor is selected from the group consisting of a cell growth factor and a replicator growth factor.

73. A population of host cells as claimed in claim 71 wherein said growth factor, recognition sequence and modulation moiety are contained in a single polypeptide.

74. A population of host cells as claimed in claim 71 wherein said mutagenizing conditions and selection conditions are imposed on the host cell population sequentially.

75. A population of host cells as claimed in claim 71 wherein said recognition sequence is said modulation moiety.

76. A population of host cells as claimed in claim 71 wherein said putative molecule or multiplicity of different putative molecules have a substrate specificity and/or catalytic activity less than that of said protease.

77. A population of host cells as claimed in claim 71 wherein said putative molecule or multiplicity of different putative molecules have a substrate specificity and/or catalytic activity greater than that of said protease.

78. A population of host cells as claimed in claim 71 wherein said putative molecules are homogeneous and/or said putative molecules are lacking the activity of said protease.

* * * * *

UNITED STATES PATENT AND TRADEMARK OFFICE
CERTIFICATE OF CORRECTION

PATENT NO.   : 6,162,640
DATED        : December 19, 2000
INVENTOR(S)  : Wohlstadter Page 1 of 1

It is certified that error appears in the above-identified patent and that said Letters Patent is hereby corrected as shown below:

Column 65,
Line 2, please add the phrase -- or multiplicity of different putative molecules -- after the word "molecule".

Signed and Sealed this

Twenty-first Day of May, 2002

Attest:

Attesting Officer

JAMES E. ROGAN
Director of the United States Patent and Trademark Office